United States Patent
Baum et al.

(10) Patent No.: US 7,244,822 B2
(45) Date of Patent: Jul. 17, 2007

(54) BTL-II PROTEINS

(75) Inventors: Peter R. Baum, Seattle, WA (US); Sabine S. Escobar, Issaquah, WA (US); Joanne L. Viney, Seattle, WA (US)

(73) Assignee: Immunex Corporation, Thousand Oaks, CA (US)

( * ) Notice: Subject to any disclaimer, the term of this patent is extended or adjusted under 35 U.S.C. 154(b) by 4 days.

(21) Appl. No.: 10/742,682

(22) Filed: Dec. 19, 2003

(65) Prior Publication Data

US 2004/0209289 A1    Oct. 21, 2004

Related U.S. Application Data

(60) Provisional application No. 60/525,298, filed on Nov. 26, 2003, provisional application No. 60/436,185, filed on Dec. 23, 2002.

(51) Int. Cl.
*C07K 14/435* (2006.01)
*C07K 14/705* (2006.01)
*C07K 14/725* (2006.01)
*C07K 16/46* (2006.01)

(52) U.S. Cl. .................................... 530/350; 530/387.3
(58) Field of Classification Search ................ 530/350, 530/387.3; 514/12; 424/134.1
See application file for complete search history.

(56) References Cited

U.S. PATENT DOCUMENTS

| | | | | |
|---|---|---|---|---|
| 5,580,756 | A * | 12/1996 | Linsley et al. ............. | 435/69.7 |
| 2002/0107363 | A1 * | 8/2002 | Fox et al. ................... | 530/350 |
| 2002/0156006 | A1 | 10/2002 | Ashkenazi et al. | |

FOREIGN PATENT DOCUMENTS

| | | |
|---|---|---|
| WO | WO 01/53836 | 7/2001 |
| WO | WO 02/00932 | 1/2002 |
| WO | WO 02/057414 | 7/2002 |
| WO | WO 03/070759 A3 | 8/2003 |
| WO | WO 2004/058288 A1 | 7/2004 |

OTHER PUBLICATIONS

Attwood, Science, 2000; 290:471-473.*
Skolnick et al., Trends in Biotech. 2000; 18(1):34-39.*
Metzler et al., Nature Structural Biol., 1997; 4:527-531.*
Flower, Trends in Immunology, 2003, vol. 24, pp. 667-674.*
Blazar et al., J. Immunol., 1996, 157: 3250-3259.*
Beck and Trowsdale, "Sequence organisation of the class II region of the human MHC" *J. Imm .Rev.* 167:201-210, 1999.
Horton, et al., "Large-scale sequence comparisons reveal unusually high levels of variation in the HLA-DQB1 locus in the class II region of the human MHC," *J. Mol. Biol.* 282:71-97, 1998.
Price, et al., "Two major histocompatibility complex haplotypes influence susceptibility to sporadic inclusion body myositis: critical evaluation of an association with HLA-DR3," *Tissue Antigen* 64:575-580, 2004.

Stammers, et al., "*BTL-II*: a polymorphic locus with homology to the butyrophilin gene family, located at the border of the major histocompatibility complex class II and class III regions in human and mouse," *Immunogenetics* 51:373-382, 2000.
Valentonyte, R. et al., "Sarcoidosis is associated with a truncating splice site mutation in *BTNL2*," *Nat Gene.* 37(4):357-364, 2005.
NCBI Annotation Project, Accession No. XM 111663, Nov. 2002.
NCBI Annotation Project, Accession No. AF186590, May 2000.
NCBI Annotation Project, Accession No. CAC69895, Sep. 2001.
NCBI Annotation Project, Accession No. NM_019602, Jun. 2001.
NCBI Annotation Project, Accession No. AF050157, Mar. 1998.
NCBI Annotation Project, Accession No. AF186592, May 2000.
NCBI Annotation Project, Accession No. AF186589, May 2000.
NCBI Annotation Project, Accession No. AF186593, May 2000.
NCBI Annotation Project, Accession No. AL662796, Apr. 2002.
NCBI Annotation Project, Accession No. XM_139886, May 2002.
NCBI Annotation Project, Accession No. XM_111663, Nov. 2002.
NCBI Annotation Project, Accession No. XM_113493, May 2002.
NCBI Annotation Project, Accession No. CAB38473, Sep. 2001.
NCBI Annotation Project, Accession No. AF186588, May 2000.
NCBI Annotation Project, Accession No. AF186590, May 2000.
NCBI Annotation Project, Accession No. AF186591, May 2000.
NCBI Annotation Project, Accession No. AF186592, May 2000.
NCBI Annotation Project, Accession No. AF008353, May 2000.
Bowie, J. et al., "Deciphering the message in protein sequences: Tolerance to amino acid substitutions," *Science* 247:1306-1310, 1990.
Zurawski, S. et al., "Definition and spatial location of mouse interleukin-2 residues that interact with its heterotrimeric receptor," *EMBO J.* 12(13):5113-5119, 1993.
T. Hunkapiller and L. Hood, "Diversity of the immunoglobulin gene superfamily," *Adv. Immunol.*, 44:1-63, 1989.
S. Ikemizu et al., "Structure and dimerization of a soluble form of B7-1," *Immunity*, 12:51-60, 2000.
P. Olins et al., "Saturation mutagenesis of human interleukin-3," *J. Biol. Chem.*, 270(40):23754-23760, 1995.
A. Sharpe and G. Freeman, "The B7-CD28 superfamily," *Nature Rev. Immunol.*, 2:116-126, 2002.
J. Zou et al., "Structure-function analysis of the p35 subunit of mouse interleukin 12," *J. Biol. Chem.*, 270(11):5864-5871, 1995.
Rhodes, D. A. et al., "The cluster of BTN genes in the extended major histocompatibility complex," *Genomics*, 71(3):351-362, 2001.

* cited by examiner

*Primary Examiner*—Phillip Gambel
*Assistant Examiner*—Ilia Ouspenski
(74) *Attorney, Agent, or Firm*—Rosemary Sweeney

(57) ABSTRACT

The invention provides isolated BTL-II proteins, nucleic acids, antibodies, antagonists, and agonists and methods of making and using the same. Diagnostic, screening, and therapeutic methods using the compositions of the invention are provided. For example, the compositions of the invention can be used for diagnosis and treatment of inflammatory bowel diseases and for enhancing a mucosal immune response to an antigen.

26 Claims, 23 Drawing Sheets

```
atggtggattttccaggctacaatctgtctggtgcagtcgcctccttcctattcatcctgctgacaatgaagcag
||||||||||||||||||||||||||||||||||||||||||||||||||||||||||||||||||||||||||
atggtggattttccaggctacaatctgtctggtgcagtcgcctccttcctattcatcctgctgacaatgaagcag tcagtcagaagactttagagtcattggccctgctcatcctatcctggccggggttggggaagatgccctgttaac
||||
tcag....... ........ ........ ........ ..... ........ ..... ........ .....
                        Missing Exon 2 and Exon 3 cagagaaactccagactgagctggcttctttaaaagtgaatggaccttcccagcccatcctcgtcagagtgggag
   |||||||||||||||||||||||||||||||||||||||||||||||||||||||||||||||||||||||
...agaaactccagactgagctggcttctttaaaagtgaatggaccttcccagcccatcctcgtcagagtgggag aagatatacagctaacctgttacctgtcccccaaggcgaatgcacagagcatggaggtgaggtgggaccgatccc
||||||||||||||||||||||||||||||||||||||||||||||||||||||||||||||||||||||||||
aagatatacagctaacctgttacctgtcccccaaggcgaatgcacagagcatggaggtgaggtgggaccgatccc accgttaccctgctgtgcatgtgtatatggatggggaccatgtggctggagagcagatggcagagtacagaggga
||||||||||||||||||||||||||||||||||||||||||||||||||||||||||||||||||||||||||
accgttaccctgctgtgcatgtgtatatggatggggaccatgtggctggagagcagatggcagagtacagaggga ggactgtgctggtgagtgacgccattgacgagggcagactgaccctgcagatactcagtgccagaccttcggacg
||||||||||||||||||||||||||||||||||||||||||||||||||||||||||||||||||||||||||
ggactgtgctggtgagtgacgccattgacgagggcagactgaccctgcagatactcagtgccagaccttcggacg acgggcagtaccgctgccttttgaaaaagatgatgtctaccaagaggccagtttggatctgaaggtggtaggtc
||||||||||||||||||||||||||||||||||||||||||||||||||||||||||||||||||||||||||
acgggcagtaccgctgccttttgaaaaagatgatgtctaccaagaggccagtttggatctgaaggtggtaggtc tgggttcttccccactgatcactgtggaggggcaagaagatGGAGAAATGCAGCCGATGTGCTCTTCAGATGGGT
||||||||||||||||||||||||||||||||||||||||||||||||||||||||||||||||||||||||||
tgggttcttccccactgatcactgtggaggggcaagaagatGGAGAAATGCAGCCGATGTGCTCTTCAGATGGGT GGTTCCCACAGCCCCACGTGCCATGGAGGGACATGGAAGGAAAGACGATACCATCATCTTCCCAGGCCCTGACTC
||||||||||||||||||||||||||||||||||||||||||||||||||||||||||||||||||||||||||
GGTTCCCACAGCCCCACGTGCCATGGAGGGACATGGAAGGAAAGACGATACCATCATCTTCCCAGGCCCTGACTC AAGGCAGCCACGGGCTGTTCCACGTGCAGACATTGCTAAGGGTCACAAACATCTCCGCTGTGGACGTCACTTGTT
||||||||||||||||||||||||||||||||||||||||||||||||||||||||||||||||||||||||||
AAGGCAGCCACGGGCTGTTCCACGTGCAGACATTGCTAAGGGTCACAAACATCTCCGCTGTGGACGTCACTTGTT CCATCAGCATCCCCTTTTTGGGCGAGGAGAAAATCGCAACTTTTTCTCTCTCAGAGTCCAGGATGACGTTTTTGT
||||||||||||||||||||||||||||||||||||||||||||||||||||||||||||||||||||||||||
CCATCAGCATCCCCTTTTTGGGCGAGGAGAAAATCGCAACTTTTTCTCTCTCAGAGTCCAGGATGACGTTTTTGT GGAAAACACTGCTTGTTTGGGGATTGCTTCTTGCTGTGGCTGTAGGCCTGCCCAGGAAGAGGAGCTGAAAAGAGT
||||||||||||||||||||||||||||||||||||||||||||||||||||||||||||||||||||||||||
GGAAAACACTGCTTGTTTGGGGATTGCTTCTTGCTGTGGCTGTAGGCCTGCCCAGGAAGAGGAGCTGAAAAGAGT GAATGTGACATTGGCTTCAAACACAGCTCACCTGAGACTGATTTCTTCTGAACAAAACAAGCGTGTGATCCATGG
||||||||||||||||||||||||||||||||||||||||||||||||||||||||||||||||||||||||||
GAATGTGACATTGGCTTCAAACACAGCTCACCTGAGACTGATTTCTTCTGAACAAAACAAGCGTGTGATCCATGG ACATTCAGGCAGCcAGATAtCCCACAGAGATCTGACTATCTGCTCTATGGGCCAGAGGGAACTCCTGTCAGGGAG
||||||||||||||||||||||||||||||||||||||||||||||||||||||||||||||||||||||||||
ACATTCAGGCAGCcAGATAtCCCACAGAGATCTGACTATCTGCTCTATGGGCCAGAGGGAACTCCTGTCAGGGAG CTGGTACTGAGAGGTGGAGACTGGGAACAGGGCGCG 1642
||||||||||||||||||||||||||||||||||||
CTGGTACTGAGAGGTGGAGACTGGGAACAGGGCGCG 1012
```

Figure 3b

```
ATGGTGGATTTTCCAGGCTACAATCTGTCTGGTGCAGTCGCCTCCTTCCTATTCATCCTGCTGACAATGAAGCAG
|||||||||||||||||||||||||||||||||||||||||||||||||||||||||||||||||||||||||||
ATGGTGGATTTTCCAGGCTACAATCTGTCTGGTGCAGTCGCCTCCTTCCTATTCATCCTGCTGACAATGAAGCAG

TCAGAAGACTTTAGAGTCATTGGCCCTGCTCATCCTATCCTGGCCGGGGTTGGGGAAGATGCCCTGTTAACCTGC
|||||||||||||||||||||||||||||||||||||||||||||||||||||||||||||||||||||||||||
TCAGAAGACTTTAGAGTCATTGGCCCTGCTCATCCTATCCTGGCCGGGGTTGGGGAAGATGCCCTGTTAACCTGC

CAGCTACTCCCCAAGAGGACCACAATGCACGTGGAGGTGAGGTGGTACCGCTCAGAGCCCAGCACACCTGTGTTT
|||||||||||||||||||||||||||||||||||||||||||||||||||||||||||||||||||||||||||
CAGCTACTCCCCAAGAGGACCACAATGCACGTGGAGGTGAGGTGGTACCGCTCAGAGCCCAGCACACCTGTGTTT

GTGCACAGGGATGGAGTGGAGGTGACTGAGATGCAGATGGAGGAGTACAGAGGCTGGGTAGAGTGGATAGAGAAT
|||||||||||||||||||||||||||||||||||||||||||||||||||||||||||||||||||||||||||
GTGCACAGGGATGGAGTGGAGGTGACTGAGATGCAGATGGAGGAGTACAGAGGCTGGGTAGAGTGGATAGAGAAT

GGCATTGCAAAGGGAAATGTGGCACTGAAGATACACAACATCCAGCCCTCCGACAATGGACAATACTGGTGCCAT
|||||||||||||||||||||||||||||||||||||||||||||||||||||||||||||||||||||||||||
GGCATTGCAAAGGGAAATGTGGCACTGAAGATACACAACATCCAGCCCTCCGACAATGGACAATACTGGTGCCAT

TTCCAGGATGGGAACTACTGTGGAGAAACAAGCTTGCTGCTCAAAGTAGCAGGTCTGGGGTCTGCCCCTAGCATC
||||||||||||||||||||||||||||||||||||||||||||||||||||||
TTCCAGGATGGGAACTACTGTGGAGAAACAAGCTTGCTGCTCAAAGTAGCAG........................
                                                    MISSING EXON 2
ACTGAGGAGAAGGGGTCGGTCATCAGCCTCCCAGAGAAACTCCAGACTGAGCTGGCTTCTTTAAAAGTGAATGGA
                                   |||||||||||||||||||||||||||||||||||||||
...................................AGAAACTCCAGACTGAGCTGGCTTCTTTAAAAGTGAATGGA

CCTTCCCAGCCCATCCTCGTCAGAGTGGGAGAAGATATACAGCTAACCTGTTACCTGTCCCCCAAGGCGAATGCA
|||||||||||||||||||||||||||||||||||||||||||||||||||||||||||||||||||||||||||
CCTTCCCAGCCCATCCTCGTCAGAGTGGGAGAAGATATACAGCTAACCTGTTACCTGTCCCCCAAGGCGAATGCA

CAGAGCATGGAGGTGAGGTGGGACCGATCCCACCGTTACCCTGCTGTGCATGTGTATATGGATGGGGACCATGTG
|||||||||||||||||||||||||||||||||||||||||||||||||||||||||||||||||||||||||||
CAGAGCATGGAGGTGAGGTGGGACCGATCCCACCGTTACCCTGCTGTGCATGTGTATATGGATGGGGACCATGTG

GCTGGAGAGCAGATGGCAGAGTACAGAGGGAGGACTGTGCTGGTGAGTGACGCCATTGACGAGGGCAGACTGACC
|||||||||||||||||||||||||||||||||||||||||||||||||||||||||||||||||||||||||||
GCTGGAGAGCAGATGGCAGAGTACAGAGGGAGGACTGTGCTGGTGAGTGACGCCATTGACGAGGGCAGACTGACC

CTGCAGATACTCAGTGCCAGACCTTCGGACGACGGGCAGTACCGCTGCCTTTTTGAAAAAGATGATGTCTACCAA
|||||||||||||||||||||||||||||||||||||||||||||||||||||||||||||||||||||||||||
CTGCAGATACTCAGTGCCAGACCTTCGGACGACGGGCAGTACCGCTGCCTTTTTGAAAAAGATGATGTCTACCAA

GAGGCCAGTTTGGATCTGAAGGTGGTAGGTCTGGGTTCTTCCCCACTGATCACTGTGGAGGGGCAAGAAGATGGA
|||||||||||||||||||||||||||||||||||||||||||||||||||||||||||||||||||||||||||
GAGGCCAGTTTGGATCTGAAGGTGGTAGGTCTGGGTTCTTCCCCACTGATCACTGTGGAGGGGCAAGAAGATGGA

GAAATGCAGCCGATGTGCTCTTCAGATGGGTGGTTCCCACAGCCCCACGTGCCATGGAGGGACATGGAAGGAAAG
|||||||||||||||||||||||||||||||||||||||||||||||||||||||||||||||||||||||||||
GAAATGCAGCCGATGTGCTCTTCAGATGGGTGGTTCCCACAGCCCCACGTGCCATGGAGGGACATGGAAGGAAAG

ACGATACCATCATCTTCCCAGGCCCTGACTCAAGGCAGCCACGGGCTGTTCCACGTGCAGACATTGCTAAGGGTC
|||||||||||||||||||||||||||||||||||||||||||||||||||||||||||||||||||||||||||
ACGATACCATCATCTTCCCAGGCCCTGACTCAAGGCAGCCACGGGCTGTTCCACGTGCAGACATTGCTAAGGGTC

ACAAACATCTCCGCTGTGGACGTCACTTGTTCCATCAGCATCCCCTTTTTGGGCGAGGAGAAAATCGCAACTTTT
|||||||||||||||||||||||||||||||||||||||||||||||||||||||||||||||||||||||||||
ACAAACATCTCCGCTGTGGACGTCACTTGTTCCATCAGCATCCCCTTTTTGGGCGAGGAGAAAATCGCAACTTTT

TCTCTCTCAGAGTCCAGGATGACGTTTTTGTGGAAAACACTGCTTGTTTGGGGATTGCTTCTTGCTGTGGCTGTA
|||||||||||||||||||||||||||||||||||||||||||||||||||||||||||||||||||||||||||
TCTCTCTCAGAGTCCAGGATGACGTTTTTGTGGAAAACACTGCTTGTTTGGGGATTGCTTCTTGCTGTGGCTGTA

GGCCTGCCCAGGAAGAGGAGCTGAAAAGAGTGAATGTGACATTGGCTTCAAACACAGCTCACCTGAGACTGATTT
|||||||||||||||||||||||||||||||||||||||||||||||||||||||||||||||||||||||||||
GGCCTGCCCAGGAAGAGGAGCTGAAAAGAGTGAATGTGACATTGGCTTCAAACACAGCTCACCTGAGACTGATTT

CTTCTGAACAAAACAAGCGTGTGATCCATGGACATTCAGGCAGCCAGATATCCCACAGAGATCTGACTATCTGCT
|||||||||||||||||||||||||||||||||||||||||||||||||||||||||||||||||||||||||||
CTTCTGAACAAAACAAGCGTGTGATCCATGGACATTCAGGCAGCCAGATATCCCACAGAGATCTGACTATCTGCT

CTATGGGCCAGAGGGAACTCCTGTCAGGGAGCTGGTACTGAGA 1618
|||||||||||||||||||||||||||||||||||||||||||
CTATGGGCCAGAGGGAACTCCTGTCAGGGAGCTGGTACTGAGA 1336
```

Figure 4b

```
ATGGTGGATTTTCCAGGCTACAATCTGTCTGGTGCAGTCGCCTCCTTCCTATTCATCCTGCTGACAATGAAGCAG
|||||||||||||||||||||||||||||||||||||||||||||||||||||||||||||||||||||||||
ATGGTGGATTTTCCAGGCTACAATCTGTCTGGTGCAGTCGCCTCCTTCCTATTCATCCTGCTGACAATGAAGCAG

TCAGTCAGAAGACTTTAGAGTCATTGGCCCTGCTCATCCTATCCTGGCCGGGGTTGGGGAAGATGCCCTGTTAAC
||||
TCAG
```

MISSING EXON2 AND EXON 3

```
 AGAAACTCCAGACTGAGCTGGCTTCTTTAAAAGTGAATGGACCTTCCCAGCCCATCCTCGTCAGAGTGGGAG
 |||||||||||||||||||||||||||||||||||||||||||||||||||||||||||||||||||||||
 AGAAACTCCAGACTGAGCTGGCTTCTTTAAAAGTGAATGGACCTTCCCAGCCCATCCTCGTCAGAGTGGGAG

AAGATATACAGCTAACCTGTTACCTGTCCCCCAAGGCGAATGCACAGAGCATGGAGGTGAGGTGGGACCGATCCC
||||||||||||||||||||||||||||||||||||||||||||||||||||||||||||||||||||||||||
AAGATATACAGCTAACCTGTTACCTGTCCCCCAAGGCGAATGCACAGAGCATGGAGGTGAGGTGGGACCGATCCC

ACCGTTACCCTGCTGTGCATGTGTATATGGATGGGGACCATGTGGCTGGAGAGCAGATGGCAGAGTACAGAGGGA
||||||||||||||||||||||||||||||||||||||||||||||||||||||||||||||||||||||||||
ACCGTTACCCTGCTGTGCATGTGTATATGGATGGGGACCATGTGGCTGGAGAGCAGATGGCAGAGTACAGAGGGA

GGACTGTGCTGGTGAGTGACGCCATTGACGAGGGCAGACTGACCCTGCAGATACTCAGTGCCAGACCTTCGGACG
||||||||||||||||||||||||||||||||||||||||||||||||||||||||||||||||||||||||||
GGACTGTGCTGGTGAGTGACGCCATTGACGAGGGCAGACTGACCCTGCAGATACTCAGTGCCAGACCTTCGGACG

ACGGGCAGTACCGCTGCCTTTTTGAAAAAGATGATGTCTACCAAGAGGCCAGTTTGGATCTGAAGGTGGTAGGTC
||||||||||||||||||||||||||||||||||||||||| ||||||||||||||||||||||||||||||||
ACGGGCAGTACCGCTGCCTTTTTGAAAAAGATGATGTCTACCAGGAGGCCAGTTTGGATCTGAAGGTGGTAGGTC

TGGGTTCTTCCCCACTGATCACTGTGGAGGGGCAAGAAGATGGAGAAATGCAGCCGATGTGCTCTTCAGATGGGT
||||||||||||||||||||||||||||||||||||||||||||||||||||||| ||| ||||||||||||||
TGGGTTCTTCCCCACTGATCACTGTGGAGGGGCAAGAAGATGGAGAAATGCAGCTGATATGCTCTTCAGATGGGT

GGTTCCCACAGCCCCACGTGCCATGGAGGGACATGGAAGGAAAGACGATACCATCATCTTCCCAGGCCCTGACTC
|||||||||||||||||||||| |||||||||||||||||||||||||||||||| ||||||||||||||||||
GGTTCCCACAGCCCCACGTGCAGTGGAGGGACATGGAAGGAAAGACGATACCATCCTCTTCCCAGGCCCTGACTC

AAGGCAGCCACGGGCTGTTCCACGTGCAGACATTGCTAAGGGTCACAAACATCTCCGCTGTGGACGTCACTTGTT
|||||||||| |||||||||||||||||||||||||||||||||||||||||||||||||||||||||||||||
AAGGCAGCCATGGGCTGTTCCACGTGCAGACATTGCTAAGGGTCACAAACATCTCCGCTGTGGACGTCACTTGTT

CCATCAGCATCCCCTTTTTGGGCGAGGAGAAAATCGCAACTTTTTCTCTCTCAG 1360
|||||||||||||||||||||||||||||||||||||||||||||||||||||
CCATCAGCATCCCCTTTTTGGGCGAGGAGAAAATCGCAACTTTTTCTCTCTCAG 730
```

Figure 5b

```
ATGGTGGATTTTCCAGGCTACAATCTGTCTGGTGCAGTCGCCTCCTTCCTATTCATCCTGCTGACAATGAAGCAG
|||||||||||||||||||||||||||||||||||||||||||||||||||||||||||||||||||||||||||
ATGGTGGATTTTCCAGGCTACAATCTGTCTGGTGCAGTCGCCTCCTTCCTATTCATCCTGCTGACAATGAAGCAG

TCAGAAGACTTTAGAGTCATTGGCCCTGCTCATCCTATCCTGGCCGGGGTTGGGGAAGATGCCCTGTTAACCTGC
|||||||||||||||||||||||||||||||||||||||||||||||||||||||||||||||||||||||||||
TCAGAAGACTTTAGAGTCATTGGCCCTGCTCATCCTATCCTGGCCGGGGTTGGGGAAGATGCCCTGTTAACCTGC

CAGCTACTCCCCAAGAGGACCACAATGCACGTGGAGGTGAGGTGGTACCGCTCAGAGCCCAGCACACCTGTGTTT
|||||||||||||||||||||||||||||||||||||||||||||||||||||||||||||||||||||||||||
CAGCTACTCCCCAAGAGGACCACAATGCACGTGGAGGTGAGGTGGTACCGCTCAGAGCCCAGCACACCTGTGTTT

GTGCACAGGGATGGAGTGGAGGTGACTGAGATGCAGATGGAGGAGTACAGAGGCTGGGTAGAGTGGATAGAGAAT
|||||||||||||||||||||||||||||||||||||||||||||||||||||||||||||||||||||||||||
GTGCACAGGGATGGAGTGGAGGTGACTGAGATGCAGATGGAGGAGTACAGAGGCTGGGTAGAGTGGATAGAGAAT

GGCATTGCAAAGGGAAATGTGGCACTGAAGATACACAACATCCAGCCCTCCGACAATGGACAATACTGGTGCCAT
|||||||||||||||||||||||||||||||||||||||||||||||||||||||||||||||||||||||||||
GGCATTGCAAAGGGAAATGTGGCACTGAAGATACACAACATCCAGCCCTCCGACAATGGACAATACTGGTGCCAT

TTCCAGGATGGGAACTACTGTGGAGAAACAAGCTTGCTGCTCAAAGTAGCAGGTCTGGGGTCTGCCCCTAGCATC
||||||||||||||||||||||||||||||||||||||||||||||||||||
TTCCAGGATGGGAACTACTGTGGAGAAACAAGCTTGCTGCTCAAAGTAGCAG.......................
                                 .MISSING EXON 3

ACTGAGGAGAAGGGGTCGGTCATCAGCCTCCCAGAGAAACTCCAGACTGAGCTGGCTTCTTTAAAAGTGAATGGA
                                  |||||||||||||||||||||||||||||||||||||||||
..........................AGAAACTCCAGACTGAGCTGGCTTCTTTAAAAGTGAATGGA 46

CCTTCCCAGCCCATCCTCGTCAGAGTGGGAGAAGATATACAGCTAACCTGTTACCTGTCCCCCAAGGCGAATGCA
|||||||||||||||||||||||||||||||||||||||||||||||||||||||||||||||||||||||||||
CCTTCCCAGCCCATCCTCGTCAGAGTGGGAGAAGATATACAGCTAACCTGTTACCTGTCCCCCAAGGCGAATGCA

CAGAGCATGGAGGTGAGGTGGGACCGATCCCACCGTTACCCTGCTGTGCATGTGTATATGGATGGGGACCATGTG
|||||||||||||||||||||||||||||||||||||||||||||||||||||||||||||||||||||||||||
CAGAGCATGGAGGTGAGGTGGGACCGATCCCACCGTTACCCTGCTGTGCATGTGTATATGGATGGGGACCATGTG

GCTGGAGAGCAGATGGCAGAGTACAGAGGGAGGACTGTGCTGGTGAGTGACGCCATTGACGAGGGCAGACTGACC
|||||||||||||||||||||||||||||||||||||||||||||||||||||||||||||||||||||||||||
GCTGGAGAGCAGATGGCAGAGTACAGAGGGAGGACTGTGCTGGTGAGTGACGCCATTGACGAGGGCAGACTGACC

CTGCAGATACTCAGTGCCAGACCTTCGGACGACGGGCAGTACCGCTGCCTTTTTGAAAAAGATGATGTCTACCAA
||||||||||||||||||||||||||||||||||||||||||||||||||||||||||||||||||||||||||
CTGCAGATACTCAGTGCCAGACCTTCGGACGACGGGCAGTACCGCTGCCTTTTTGAAAAAGATGATGTCTACCAG

GAGGCCAGTTTGGATCTGAAGGTGGTAGGTCTGGGTTCTTCCCCACTGATCACTGTGGAGGGGCAAGAAGATGGA
|||||||||||||||||||||||||||||||||||||||||||||||||||||||||||||||||||||||||||
GAGGCCAGTTTGGATCTGAAGGTGGTAGGTCTGGGTTCTTCCCCACTGATCACTGTGGAGGGGCAAGAAGATGGA

GAAATGCAGCCGATGTGCTCTTCAGATGGGTGGTTCCCACAGCCCCACGTGCCATGGAGGGACATGGAAGGAAAG
||||||||||| ||| |||||||||||||||||||||||||||||||||||||| ||||||||||||||||||||
GAAATGCAGCTGATATGCTCTTCAGATGGGTGGTTCCCACAGCCCCACGTGCAGTGGAGGGACATGGAAGGAAAG

ACGATACCATCATCTTCCCAGGCCCTGACTCAAGGCAGCCACGGGCTGTTCCACGTGCAGACATTGCTAAGGGTC
|||||||||||  |||||||||||||||||||||||||||||| |||||||||||||||||||||||||||||||
ACGATACCATCCTCTTCCCAGGCCCTGACTCAAGGCAGCCATGGGCTGTTCCACGTGCAGACATTGCTAAGGGTC

ACAAACATCTCCGCTGTGGACGTCACTTGTTCCATCAGCATCCCCTTTTTGGGCGAGGAGAAAATCGCAACTTTT
|||||||||||||||||||||||||||||||||||||||||||||||||||||||||||||||||||||||||||
ACAAACATCTCCGCTGTGGACGTCACTTGTTCCATCAGCATCCCCTTTTTGGGCGAGGAGAAAATCGCAACTTTT

TCTCTCTCAG 1360
||||||||||
TCTCTCTCAG 1078
```

Figure 6b

```
ATGGTGGATTTTCCAGGCTACAATCTGTCTGGTGCAGTCGCCTCCTTCCTATTCATCCTGCTGACAATGAAGCAG
||||||||||||||||||||||||||||||||||||||||||||||||||||||||||||||||||||||||||
ATGGTGGATTTTCCAGGCTACAATCTGTCTGGTGCAGTCGCCTCCTTCCTATTCATCCTGCTGACAATGAAGCAG

TCAGAAGACTTTAGAGTCATTGGCCCTGCTCATCCTATCCTGGCCGGGGTTGGGGAAGATGCCCTGTTAACCTGC
||   |||||||||||||||||||||||||||||||||||||||||||||||||||||||||||||||||||||
TC...AGACTTTAGAGTCATTGGCCCTGCTCATCCTATCCTGGCCGGGGTTGGGGAAGATGCCCTGTTAACCTGC

CAGCTACTCCCCAAGAGGACCACAATGCACGTGGAGGTGAGGTGGTACCGCTCAGAGCCCAGCACACCTGTGTTT
||||||||||||||||||||||||||||||||||||||||||||||||||||||||||||||||||||||||||
CAGCTACTCCCCAAGAGGACCACAATGCACGTGGAGGTGAGGTGGTACCGCTCAGAGCCCAGCACACCTGTGTTT

GTGCACAGGGATGGAGTGGAGGTGACTGAGATGCAGATGGAGGAGTACAGAGGCTGGGTAGAGTGGATAGAGAAT
||||||||||||||||||||||||||||||||||||||||||||||||||||||||||||||||||||||||||
GTGCACAGGGATGGAGTGGAGGTGACTGAGATGCAGATGGAGGAGTACAGAGGCTGGGTAGAGTGGATAGAGAAT

GGCATTGCAAAGGGAAATGTGGCACTGAAGATACACAACATCCAGCCCTCCGACAATGGACAATACTGGTGCCAT
||||||||||||||||||||||||||||||||||||||||||||||||||||||||||||||||||||||||||
GGCATTGCAAAGGGAAATGTGGCACTGAAGATACACAACATCCAGCCCTCCGACAATGGACAATACTGGTGCCAT

TTCCAGGATGGGAACTACTGTGGAGAAACAAGCTTGCTGCTCAAAGTAGCAGGTCTGGGGTCTGCCCCTAGCATC
|||||||||||||||||||||||||||||||||||||||||||||||||
TTCCAGGATGGGAACTACTGTGGAGAAACAAGCTTGCTGCTCAAAGTAG..........................
                                                MISSING EXON 3

ACTGAGGAGAAGGGGTCGGTCATCAGCCTCCCAGAGAAACTCCAGACTGAGCTGGCTTCTTTAAAAGTGAATGGA
                               ||||||||||||||||||||||||||||||||||||||||||
...............................CAGAGAAACTCCAGACTGAGCTGGCTTCTTTAAAAGTGAATGGA

CCTTCCCAGCCCATCCTCGTCAGAGTGGGAGAAGATATACAGCTAACCTGTTACCTGTCCCCCAAGGCGAATGCA
||||||||||||||||||||||||||||||||||||||||||||||||||||||||||||||||||||||||||
CCTTCCCAGCCCATCCTCGTCAGAGTGGGAGAAGATATACAGCTAACCTGTTACCTGTCCCCCAAGGCGAATGCA

CAGAGCATGGAGGTGAGGTGGGACCGATCCCACCGTTACCCTGCTGTGCATGTGTATATGGATGGGGACCATGTG
||||||||||||||||||||||||||||||||||||||||||||||||||||||||||||||||||||||||||
CAGAGCATGGAGGTGAGGTGGGACCGATCCCACCGTTACCCTGCTGTGCATGTGTATATGGATGGGGACCATGTG

GCTGGAGAGCAGATGGCAGAGTACAGAGGGAGGACTGTGCTGGTGAGTGACGCCATTGACGAGGGCAGACTGACC
||||||||||||||||||||||||||||||||||||||||||||||||||||||||||||||||||||||||||
GCTGGAGAGCAGATGGCAGAGTACAGAGGGAGGACTGTGCTGGTGAGTGACGCCATTGACGAGGGCAGACTGACC

CTGCAGATACTCAGTGCCAGACCTTCGGACGACGGGCAGTACCGCTGCCTTTTTGAAAAAGATGATGTCTACCAA
|||||||||||||||||||||||||||||||||||||||||||||||||||||||||||||||||||||||| |
CTGCAGATACTCAGTGCCAGACCTTCGGACGACGGGCAGTACCGCTGCCTTTTTGAAAAAGATGATGTCTACCAG

GAGGCCAGTTTGGATCTGAAGGTGGTAGGTCTGGGTTCTTCCCCACTGATCACTGTGGAGGGGCAAGAAGATGGA
||||||||||||||||||||||||||||||||||||||||||||||||||||||||||||||||||||||||||
GAGGCCAGTTTGGATCTGAAGGTGGTAGGTCTGGGTTCTTCCCCACTGATCACTGTGGAGGGGCAAGAAGATGGA

GAAATGCAGCCGATGTGCTCTTCAGATGGGTGGTTCCCACAGCCCCACGTGCCATGGAGGGACATGGAAGGAAAG
|||||||||| ||| |||||||||||||||||||||||||||||||||||||| ||||||||||||||||||||
GAAATGCAGCTGATATGCTCTTCAGATGGGTGGTTCCCACAGCCCCACGTGCCAGTGGAGGGACATGGAAGGAAAG

ACGATACCATCATCTTCCCAGGCCCTGACTCAAGGCAGCCACGGGCTGTTCCACGTGCAGACATTGCTAAGGGTC
||||||||||| || |||||||||||||||||||||||||| ||||||||||||||||||||||||||||||||
ACGATACCATCCTCTTCCCAGGCCCTGACTCAAGGCAGCCATGGGCTGTTCCACGTGCAGACATTGCTAAGGGTC

ACAAACATCTCCGCTGTGGACGTCACTTGTTCCATCAGCATCCCCTTTTTGGGCGAGGAGAAAATCGCAACTTTT
||||||||||||||||||||||||||||||||||||||||||||||||||||||||||||||||||||||||||
ACAAACATCTCCGCTGTGGACGTCACTTGTTCCATCAGCATCCCCTTTTTGGGCGAGGAGAAAATCGCAACTTTT

TCTCTCTCAG 1360
||||||||||
TCTCTCTCAG 1075
```

Figure 7b

```
ATGGTGGATTGCCCACGGTATAGTCTATCTGGCGTGGCTGCCTCCTTCCTCTTCGTCCTGCTGACTATAAAGCAC
|||||||||||||||||||||||||||||||||||||||||||||||||||||||||||||||||||||||||||
ATGGTGGATTGCCCACGGTATAGTCTATCTGGCGTGGCTGCCTCCTTCCTCTTCGTCCTGCTGACTATAAAGCAC

CCAGATGACTTCAGAGTGGTCGGTCCTAACCTCCCAATCCTGGCTAAAGTCGGGGAAGATGCCCTGCTAACGTGT
|||||||||||||||||||||||||||||||||||||||||||||||||||||||||||||||||||||||||||
CCAGATGACTTCAGAGTGGTCGGTCCTAACCTCCCAATCCTGGCTAAAGTCGGGGAAGATGCCCTGCTAACGTGT

CAGCTCCTCCCCAAGAGGACCACGGCACACATGGAGGTGAGGTGGTACCGCTCCGACCCTGCCATGCCAGTGATT
|||||||||||||||||||||||||||||||||||||||||||||||||||||||||||||||||||||||||||
CAGCTCCTCCCCAAGAGGACCACGGCACACATGGAGGTGAGGTGGTACCGCTCCGACCCTGCCATGCCAGTGATT

ATGTACCGGGATGGAGCTGTGGTGACTGGGCTACCGATGGAGGGGTACGGAGGCCGGGCAGAGTGGATGGAGGAC
|||||||||||||||||||||||||||||||||||||||||||||||||||||||||||||||||||||||||||
ATGTACCGGGATGGAGCTGTGGTGACTGGGCTACCGATGGAGGGGTACGGAGGCCGGGCAGAGTGGATGGAGGAC

AGCACTGAAGAGGGCAGTGTGGCTCTGAAGATTCGCCAGGTCCAGCCAAGTGACGATGGCCAGTACTGGTGCCGC
|||||||||||||||||||||||||||||||||||||||||||||||||||||||||||||||||||||||||||
AGCACTGAAGAGGGCAGTGTGGCTCTGAAGATTCGCCAGGTCCAGCCAAGTGACGATGGCCAGTACTGGTGCCGC

TTCCAGGAGGGGGACTACTGGAGAGAGACAAGCGTGCTACTCCAAGTGGCTGCTCTAGGATCTTCCCCAAATATC
||||||||||||||||||||||||||||||||||||||||||||||||||||
TTCCAGGAGGGGGACTACTGGAGAGAGACAAGCGTGCTACTCCAAGTGGCT.......................
                                                   Missing Exon 3
AGAGAGACCCAGGAGGCCACCATCGCTCTGTCAGAGAGGCTCCAGACCGAACTGGTTTCCGTTAGCGTAATCGGA
                              |||||||||||||||||||||||||||||||||||||||||||||
..............................GAGAGGCTCCAGACCGAACTGGTTTCCGTTAGCGTAATCGGA CATTCCCAGCCCAGCCCTGTTCAAGTCGGAGAGAACATAGAATTAACTTGTCACCTCTCACCTCAAACGGATGCT
|||||||||||||||||||||||||||||||||||||||||||||||||||||||||||||||||||||||||||
CATTCCCAGCCCAGCCCTGTTCAAGTCGGAGAGAACATAGAATTAACTTGTCACCTCTCACCTCAAACGGATGCT CAGAACTTAGAGGTGAGGtGGCTCCGATCCCGCTATTACCCTGCAGTCCACGTGTATGCAAATGGCACCCACGTG
|||||||||||||||||| ||||||||||||||||||||||||||||||||||||||||||||||||||||||||
CAGAACTTAGAGGTGAGGTGGCTCCGATCCCGCTATTACCCTGCAGTCCACGTGTATGCAAATGGCACCCACGTG GCTGGAGAGCAGATGGTAGAATACAAAGGGAGGACTTCATTGGTGACTGATGCCATCCACGAGGGAAAACTGACC
|||||||||||||||||||||||||||||||||||||||||||||||||||||||||||||||||||||||||||
GCTGGAGAGCAGATGGTAGAATACAAAGGGAGGACTTCATTGGTGACTGATGCCATCCACGAGGGAAAACTGACC CTGCAGATTCACAATGCCAGAACTTCGGATGAAGGGCAGTACCGGTGCCTTTTTGGAAAAGATGGTGTCTACCAG
|||||||||||||||||||||||||||||||||||||||||||||||||||||||||||||||||||||||||||
CTGCAGATTCACAATGCCAGAACTTCGGATGAAGGGCAGTACCGGTGCCTTTTTGGAAAAGATGGTGTCTACCAG GAGGCCCGTGTGGATGTGCAGGTGACGGCGGTGGGTTCCACCCCACGGATCACCAGGGAGGTCTTGAAAGATGGA
|||||||||||||||||||||||||||||||||||||||||||||||||||||||||||||||||||||||||||
GAGGCCCGTGTGGATGTGCAGGTGACGGCGGTGGGTTCCACCCCACGGATCACCAGGGAGGTCTTGAAAGATGGA GGCATGCAGCTGAGGTGTACGTCTGATGGGTGGTTCCCACGGCCCCATGTGCAGTGGAGGGACAGAGATGGAAAG
|||||||||||||||||||||||||||||||||||||||||||||||||||||||||||||||||||||||||||
GGCATGCAGCTGAGGTGTACGTCTGATGGGTGGTTCCCACGGCCCCATGTGCAGTGGAGGGACAGAGATGGAAAG ACAATGCCATCGTTTTCCGAGGCCTTTCAGCAAGGGAGCCAGGAGCTGTTCCAGGTGGAGACACTTCTGCTGGTC
|||||||||||||||||||||||||||||||||||||||||||||||||||||||||||||||||||||||||||
ACAATGCCATCGTTTTCCGAGGCCTTTCAGCAAGGGAGCCAGGAGCTGTTCCAGGTGGAGACACTTCTGCTGGTC ACAAACGGCTCCATGGTGAATGTGACCTGCTCCATCAGCCTCCCTCTGGGCCAGGAGAAAACAGCCCGTTTccct
|||||||||||||||||||||||||||||||||||||||||||||||||||||||||||||||||||||||||||
ACAAACGGCTCCATGGTGAATGTGACCTGCTCCATCAGCCTCCCTCTGGGCCAGGAGAAAACAGCCCGTTTCCCT ctctcaGACTCCAAGATAGCTtTGTTATGGATGACCCTGCCTGTTGTGGTGCTGCCTCTCGCCATGGCTATGGAC
||||||||||||||||||||| |||||||||||||||||||||||||||||||||||||||||||||||||||||
CTCTCAGACTCCAAGATAGCTTTGTTATGGATGACCCTGCCTGTTGTGGTGCTGCCTCTCGCCATGGCTATGGAC CTGATCAAGGTGAAACGGCGGCGACGGACCAATGAACAAACACACAGCAGCAATCAGGAAAATAACAAGAATGAC
|||||||||||||||||||||||||||||||||||||||||||||||||||||||||||||||||||||||||||
CTGATCAAGGTGAAACGGCGGCGACGGACCAATGAACAAACACACAGCAGCAATCAGGAAAATAACAAGAATGAC GAAAACCACAGGCGGCGACtTCCTTCTGACGAGAGGCTCAGATGAAAATGCACCCCGCAAGCCCAACGCACCCCA
||||||||||||||||||| |||||||||||||||||||||||||||||||||||||||||||||||||||||||
GAAAACCACAGGCGGCGACTTCCTTCTGACGAGAGGCTCAGATGAAAATGCACCCCGCAAGCCCAACGCACCCCA TTTCCTGAacACCCCATCCCTCCTCCCATCTTTTCCCCTCAATAAGCTGCACTGACATAGGAGTGGTTTCACTTG
|||||||| |||||||||||||||||||||||||||||||||||||||||||||||||||||||||||||||||
TTTCCTGAACACCCCATCCCTCCTCCCATCTTTTCCCCTCAATAAGCTGCACTGACATAGGAGTGGTTTCACTTG CTACTCTCCAAAGGTTCTTCATGGACCCTGTCCGTACCTGATGCAACCATCACGCACAG 1709
||||||||||||||||||||||||||||||||||||||||||||||||||||||||||
CTACTCTCCAAAGGTTCTTCATGGACCCTGTCCGTACCTGATGCAACCATCACGCACAG 1427
```

Figure 9b

ID NO:10, SEQ ID NO:14,

SEQUENCE LISTING

<160> NUMBER OF SEQ ID NOS: 20

<210> SEQ ID NO 1
<211> LENGTH: 1368
<212> TYPE: DNA
<213> ORGANISM: Homo sapiens
<220> FEATURE:
<221> NAME/KEY: CDS
<222> LOCATION: (1)..(1365)

<400> SEQUENCE: 1

```
atg gtg gat ttt cca ggc tac aat ctg tct ggt gca gtc gcc tcc ttc      48
Met Val Asp Phe Pro Gly Tyr Asn Leu Ser Gly Ala Val Ala Ser Phe
  1               5                  10                  15 cta ttc atc ctg ctg aca atg aag cag tca gaa gac ttt aga gtc att      96
Leu Phe Ile Leu Leu Thr Met Lys Gln Ser Glu Asp Phe Arg Val Ile
             20                  25                  30 ggc cct gct cat cct atc ctg gcc ggg gtt ggg gaa gat gcc ctg tta     144
Gly Pro Ala His Pro Ile Leu Ala Gly Val Gly Glu Asp Ala Leu Leu
         35                  40                  45 acc tgc cag cta ctc ccc aag agg acc aca atg cac gtg gag gtg agg     192
Thr Cys Gln Leu Leu Pro Lys Arg Thr Thr Met His Val Glu Val Arg
     50                  55                  60 tgg tac cgc tca gag ccc agc aca cct gtg ttt gtg cac agg gat gga     240
Trp Tyr Arg Ser Glu Pro Ser Thr Pro Val Phe Val His Arg Asp Gly
 65                  70                  75                  80 gtg gag gtg act gag atg cag atg gag gag tac aga ggc tgg gta gag     288
Val Glu Val Thr Glu Met Gln Met Glu Glu Tyr Arg Gly Trp Val Glu
                 85                  90                  95 tgg ata gag aat ggc att gca aag gga aat gtg gca ctg aag ata cac     336
Trp Ile Glu Asn Gly Ile Ala Lys Gly Asn Val Ala Leu Lys Ile His
            100                 105                 110 aac atc cag ccc tcc gac aat gga caa tac tgg tgc cat ttc cag gat     384
Asn Ile Gln Pro Ser Asp Asn Gly Gln Tyr Trp Cys His Phe Gln Asp
        115                 120                 125 ggg aac tac tgt gga gaa aca agc ttg ctg ctc aaa gta gca ggt ctg     432
Gly Asn Tyr Cys Gly Glu Thr Ser Leu Leu Leu Lys Val Ala Gly Leu
    130                 135                 140 ggg tct gcc cct agc atc cac atg gag gga cct ggg gag agt gga gtc     480
Gly Ser Ala Pro Ser Ile His Met Glu Gly Pro Gly Glu Ser Gly Val
145                 150                 155                 160 cag ctt gtg tgc act gca agg ggc tgg ttc cca gag ccc cag gtg tat     528
Gln Leu Val Cys Thr Ala Arg Gly Trp Phe Pro Glu Pro Gln Val Tyr
                165                 170                 175 tgg gaa gac atc cgg gga gag aag ctg ctg gcc gtg tct gag cat cgc     576
Trp Glu Asp Ile Arg Gly Glu Lys Leu Leu Ala Val Ser Glu His Arg
            180                 185                 190 atc caa gat aaa gat ggc ctg ttc tat gcg gaa gcc acc ctg gtg gtc     624
Ile Gln Asp Lys Asp Gly Leu Phe Tyr Ala Glu Ala Thr Leu Val Val
        195                 200                 205 agg aac gcc tct gca gag tct gtg tcc tgc ttg gtc cac aac ccc gtc     672
Arg Asn Ala Ser Ala Glu Ser Val Ser Cys Leu Val His Asn Pro Val
    210                 215                 220 ctc act gag gag aag ggg tcg gtc atc agc ctc cca gag aaa ctc cag     720
Leu Thr Glu Glu Lys Gly Ser Val Ile Ser Leu Pro Glu Lys Leu Gln
225                 230                 235                 240 act gag ctg gct tct tta aaa gtg aat gga cct tcc cag ccc atc ctc     768
Thr Glu Leu Ala Ser Leu Lys Val Asn Gly Pro Ser Gln Pro Ile Leu
                245                 250                 255 gtc aga gtg gga gaa gat ata cag cta acc tgt tac ctg tcc ccc aag     816
Val Arg Val Gly Glu Asp Ile Gln Leu Thr Cys Tyr Leu Ser Pro Lys
            260                 265                 270 gcg aat gca cag agc atg gag gtg agg tgg gac cga tcc cac cgt tac     864
Ala Asn Ala Gln Ser Met Glu Val Arg Trp Asp Arg Ser His Arg Tyr
        275                 280                 285 cct gct gtg cat gtg tat atg gat ggg gac cat gtg gct gga gag cag     912
Pro Ala Val His Val Tyr Met Asp Gly Asp His Val Ala Gly Glu Gln
    290                 295                 300
```

-continued

```
atg gca gag tac aga ggg agg act gta ctg gtg agt gac gcc att gac     960
Met Ala Glu Tyr Arg Gly Arg Thr Val Leu Val Ser Asp Ala Ile Asp
305                 310                 315                 320 gag ggc aga ctg acc ctg cag ata ctc agt gcc aga cct tcg gac gac    1008
Glu Gly Arg Leu Thr Leu Gln Ile Leu Ser Ala Arg Pro Ser Asp Asp
            325                 330                 335 ggg cag tac cgc tgc ctt ttt gaa aaa gat gat gtc tac cag gag gcc    1056
Gly Gln Tyr Arg Cys Leu Phe Glu Lys Asp Asp Val Tyr Gln Glu Ala
        340                 345                 350 agt ttg gat ctg aag gtg gta agt ctg ggt tct tcc cca ctg atc act    1104
Ser Leu Asp Leu Lys Val Val Ser Leu Gly Ser Ser Pro Leu Ile Thr
    355                 360                 365 gtg gag ggg caa gaa gat gga gaa atg cag ccg atg tgc tct tca gat    1152
Val Glu Gly Gln Glu Asp Gly Glu Met Gln Pro Met Cys Ser Ser Asp
370                 375                 380 ggg tgg ttc cca cag ccc cac gtg cca tgg agg gac atg gaa gga aag    1200
Gly Trp Phe Pro Gln Pro His Val Pro Trp Arg Asp Met Glu Gly Lys
385                 390                 395                 400 acg ata cca tca tct tcc cag gcc ctg act caa ggc agc cac ggg ctg    1248
Thr Ile Pro Ser Ser Ser Gln Ala Leu Thr Gln Gly Ser His Gly Leu
            405                 410                 415 ttc cac gtg cag aca ttg cta agg gtc aca aac atc tcc gct gtg gac    1296
Phe His Val Gln Thr Leu Leu Arg Val Thr Asn Ile Ser Ala Val Asp
        420                 425                 430 gtc act tgt tcc atc agc atc ccc ttt ttg ggc gag gag aaa atc gca    1344
Val Thr Cys Ser Ile Ser Ile Pro Phe Leu Gly Glu Glu Lys Ile Ala
    435                 440                 445 act ttt tct ctc tca ggt tgg tga                                    1368
Thr Phe Ser Leu Ser Gly Trp
450                 455

<210> SEQ ID NO 2
<211> LENGTH: 455
<212> TYPE: PRT
<213> ORGANISM: Homo sapiens

<400> SEQUENCE: 2

Met Val Asp Phe Pro Gly Tyr Asn Leu Ser Gly Ala Val Ala Ser Phe
1               5                   10                  15

Leu Phe Ile Leu Leu Thr Met Lys Gln Ser Glu Asp Phe Arg Val Ile
            20                  25                  30

Gly Pro Ala His Pro Ile Leu Ala Gly Val Gly Glu Asp Ala Leu Leu
        35                  40                  45

Thr Cys Gln Leu Leu Pro Lys Arg Thr Thr Met His Val Glu Val Arg
    50                  55                  60

Trp Tyr Arg Ser Glu Pro Ser Thr Pro Val Phe Val His Arg Asp Gly
65                  70                  75                  80

Val Glu Val Thr Glu Met Gln Met Glu Glu Tyr Arg Gly Trp Val Glu
                85                  90                  95

Trp Ile Glu Asn Gly Ile Ala Lys Gly Asn Val Ala Leu Lys Ile His
            100                 105                 110

Asn Ile Gln Pro Ser Asp Asn Gly Gln Tyr Trp Cys His Phe Gln Asp
        115                 120                 125

Gly Asn Tyr Cys Gly Glu Thr Ser Leu Leu Leu Lys Val Ala Gly Leu
    130                 135                 140

Gly Ser Ala Pro Ser Ile His Met Glu Gly Pro Gly Glu Ser Gly Val
145                 150                 155                 160
```

-continued

```
Gln Leu Val Cys Thr Ala Arg Gly Trp Phe Pro Glu Pro Gln Val Tyr
            165                 170                 175

Trp Glu Asp Ile Arg Gly Glu Lys Leu Leu Ala Val Ser Glu His Arg
            180                 185                 190

Ile Gln Asp Lys Asp Gly Leu Phe Tyr Ala Glu Ala Thr Leu Val Val
            195                 200                 205

Arg Asn Ala Ser Ala Glu Ser Val Ser Cys Leu Val His Asn Pro Val
210                 215                 220

Leu Thr Glu Glu Lys Gly Ser Val Ile Ser Leu Pro Glu Lys Leu Gln
225                 230                 235                 240

Thr Glu Leu Ala Ser Leu Lys Val Asn Gly Pro Ser Gln Pro Ile Leu
            245                 250                 255

Val Arg Val Gly Glu Asp Ile Gln Leu Thr Cys Tyr Leu Ser Pro Lys
            260                 265                 270

Ala Asn Ala Gln Ser Met Glu Val Arg Trp Asp Arg Ser His Arg Tyr
            275                 280                 285

Pro Ala Val His Val Tyr Met Asp Gly Asp His Val Ala Gly Glu Gln
290                 295                 300

Met Ala Glu Tyr Arg Gly Arg Thr Val Leu Val Ser Asp Ala Ile Asp
305                 310                 315                 320

Glu Gly Arg Leu Thr Leu Gln Ile Leu Ser Ala Arg Pro Ser Asp Asp
            325                 330                 335

Gly Gln Tyr Arg Cys Leu Phe Glu Lys Asp Asp Val Tyr Gln Glu Ala
            340                 345                 350

Ser Leu Asp Leu Lys Val Val Ser Leu Gly Ser Ser Pro Leu Ile Thr
            355                 360                 365

Val Glu Gly Gln Glu Asp Gly Glu Met Gln Pro Met Cys Ser Ser Asp
            370                 375                 380

Gly Trp Phe Pro Gln Pro His Val Pro Trp Arg Asp Met Glu Gly Lys
385                 390                 395                 400

Thr Ile Pro Ser Ser Gln Ala Leu Thr Gln Gly Ser His Gly Leu
            405                 410                 415

Phe His Val Gln Thr Leu Leu Arg Val Thr Asn Ile Ser Ala Val Asp
            420                 425                 430

Val Thr Cys Ser Ile Ser Ile Pro Phe Leu Gly Glu Glu Lys Ile Ala
            435                 440                 445

Thr Phe Ser Leu Ser Gly Trp
450                 455

<210> SEQ ID NO 3
<211> LENGTH: 2011
<212> TYPE: DNA
<213> ORGANISM: Homo sapiens
<220> FEATURE:
<221> NAME/KEY: CDS
<222> LOCATION: (1)..(1449)

<400> SEQUENCE: 3 atg gtg gat ttt cca ggc tac aat ctg tct ggt gca gtc gcc tcc ttc      48
Met Val Asp Phe Pro Gly Tyr Asn Leu Ser Gly Ala Val Ala Ser Phe
1               5                   10                  15 cta ttc atc ctg ctg aca atg aag cag tca gaa gac ttt aga gtc att      96
Leu Phe Ile Leu Leu Thr Met Lys Gln Ser Glu Asp Phe Arg Val Ile
                20                  25                  30 ggc cct gct cat cct atc ctg gcc ggg gtt ggg gaa gat gcc ctg tta     144
Gly Pro Ala His Pro Ile Leu Ala Gly Val Gly Glu Asp Ala Leu Leu
            35                  40                  45
```

```
acc tgc cag cta ctc ccc aag agg acc aca atg cac gtg gag gtg agg      192
Thr Cys Gln Leu Leu Pro Lys Arg Thr Thr Met His Val Glu Val Arg
 50              55                  60 tgg tac cgc tca gag ccc agc aca cct gtg ttt gtg cac agg gat gga      240
Trp Tyr Arg Ser Glu Pro Ser Thr Pro Val Phe Val His Arg Asp Gly
 65              70                  75                  80 gtg gag gtg act gag atg cag atg gag gag tac aga ggc tgg gta gag      288
Val Glu Val Thr Glu Met Gln Met Glu Glu Tyr Arg Gly Trp Val Glu
                 85                  90                  95 tgg ata gag aat ggc att gca aag gga aat gtg gca ctg aag ata cac      336
Trp Ile Glu Asn Gly Ile Ala Lys Gly Asn Val Ala Leu Lys Ile His
            100                 105                 110 aac atc cag ccc tcc gac aat gga caa tac tgg tgc cat ttc cag gat      384
Asn Ile Gln Pro Ser Asp Asn Gly Gln Tyr Trp Cys His Phe Gln Asp
            115                 120                 125 ggg aac tac tgt gga gaa aca agc ttg ctc ctc aaa gta gca ggt ctg      432
Gly Asn Tyr Cys Gly Glu Thr Ser Leu Leu Leu Lys Val Ala Gly Leu
130                 135                 140 ggg tct gcc cct agc atc cac atg gag gga cct ggg gag agt gga gtc      480
Gly Ser Ala Pro Ser Ile His Met Glu Gly Pro Gly Glu Ser Gly Val
145                 150                 155                 160 cag ctt gtg tgc act gca agg ggc tgg ttc cca gag ccc cag gtg tat      528
Gln Leu Val Cys Thr Ala Arg Gly Trp Phe Pro Glu Pro Gln Val Tyr
                165                 170                 175 tgg gaa gac atc cgg gga gag aag ctg ctg gcc gtg tct gag cat cgc      576
Trp Glu Asp Ile Arg Gly Glu Lys Leu Leu Ala Val Ser Glu His Arg
                180                 185                 190 atc caa gat aaa gat ggc ctg ttc tat gcg gaa gcc acc ctg gtg gtc      624
Ile Gln Asp Lys Asp Gly Leu Phe Tyr Ala Glu Ala Thr Leu Val Val
            195                 200                 205 agg aac gcc tct gca gag tct gtg tcc tgc ttg gtc cac aac ccc gtc      672
Arg Asn Ala Ser Ala Glu Ser Val Ser Cys Leu Val His Asn Pro Val
            210                 215                 220 ctc act gag gag aag ggg tcg gtc atc agc ctc cca gag aaa ctc cag      720
Leu Thr Glu Glu Lys Gly Ser Val Ile Ser Leu Pro Glu Lys Leu Gln
225                 230                 235                 240 act gag ctg gct tct tta aaa gtg aat gga cct tcc cag ccc atc ctc      768
Thr Glu Leu Ala Ser Leu Lys Val Asn Gly Pro Ser Gln Pro Ile Leu
                245                 250                 255 gtc aga gtg gga gaa gat ata cag cta acc tgt tac ctg tcc ccc aag      816
Val Arg Val Gly Glu Asp Ile Gln Leu Thr Cys Tyr Leu Ser Pro Lys
                260                 265                 270 gcg aat gca cag agc atg gag gtg agg tgg gac cga tcc cac cgt tac      864
Ala Asn Ala Gln Ser Met Glu Val Arg Trp Asp Arg Ser His Arg Tyr
            275                 280                 285 cct gct gtg cat gtg tat atg gat ggg gac cat gtg gct gga gag cag      912
Pro Ala Val His Val Tyr Met Asp Gly Asp His Val Ala Gly Glu Gln
            290                 295                 300 atg gca gag tac aga ggg agg act gtg ctg gtg agt gac gcc att gac      960
Met Ala Glu Tyr Arg Gly Arg Thr Val Leu Val Ser Asp Ala Ile Asp
305                 310                 315                 320 gag ggc aga ctg acc ctg cag ata ctc agt gcc aga cct tcg gac gac      1008
Glu Gly Arg Leu Thr Leu Gln Ile Leu Ser Ala Arg Pro Ser Asp Asp
                325                 330                 335 ggg cag tac cgc tgc ctt ttt gaa aaa gat gat gtc tac caa gag gcc      1056
Gly Gln Tyr Arg Cys Leu Phe Glu Lys Asp Asp Val Tyr Gln Glu Ala
                340                 345                 350 agt ttg gat ctg aag gtg gta ggt ctg ggt tct tcc cca ctg atc act      1104
Ser Leu Asp Leu Lys Val Val Gly Leu Gly Ser Ser Pro Leu Ile Thr
                355                 360                 365
```

| | | | | | | | | | | | | | | | | |
|---|---|---|---|---|---|---|---|---|---|---|---|---|---|---|---|---|
| gtg | gag | ggg | caa | gaa | gat | gga | gaa | atg | cag | ccg | atg | tgc | tct | tca | gat | 1152 |
| Val | Glu | Gly | Gln | Glu | Asp | Gly | Glu | Met | Gln | Pro | Met | Cys | Ser | Ser | Asp | |
| | 370 | | | | | 375 | | | | | 380 | | | | | |
| ggg | tgg | ttc | cca | cag | ccc | cac | gtg | cca | tgg | agg | gac | atg | gaa | gga | aag | 1200 |
| Gly | Trp | Phe | Pro | Gln | Pro | His | Val | Pro | Trp | Arg | Asp | Met | Glu | Gly | Lys | |
| 385 | | | | | 390 | | | | | 395 | | | | | 400 | |
| acg | ata | cca | tca | tct | tcc | cag | gcc | ctg | act | caa | ggc | agc | cac | ggg | ctg | 1248 |
| Thr | Ile | Pro | Ser | Ser | Ser | Gln | Ala | Leu | Thr | Gln | Gly | Ser | His | Gly | Leu | |
| | | | | 405 | | | | | 410 | | | | | 415 | | |
| ttc | cac | gtg | cag | aca | ttg | cta | agg | gtc | aca | aac | atc | tcc | gct | gtg | gac | 1296 |
| Phe | His | Val | Gln | Thr | Leu | Leu | Arg | Val | Thr | Asn | Ile | Ser | Ala | Val | Asp | |
| | | 420 | | | | | 425 | | | | | 430 | | | | |
| gtc | act | tgt | tcc | atc | agc | atc | ccc | ttt | ttg | ggc | gag | gag | aaa | atc | gca | 1344 |
| Val | Thr | Cys | Ser | Ile | Ser | Ile | Pro | Phe | Leu | Gly | Glu | Glu | Lys | Ile | Ala | |
| | | 435 | | | | | 440 | | | | | 445 | | | | |
| act | ttt | tct | ctc | tca | gag | tcc | agg | atg | acg | ttt | ttg | tgg | aaa | aca | ctg | 1392 |
| Thr | Phe | Ser | Leu | Ser | Glu | Ser | Arg | Met | Thr | Phe | Leu | Trp | Lys | Thr | Leu | |
| | 450 | | | | | 455 | | | | | 460 | | | | | |
| ctt | gtt | tgg | gga | ttg | ctt | ctt | gct | gtg | gct | gta | ggc | ctg | ccc | agg | aag | 1440 |
| Leu | Val | Trp | Gly | Leu | Leu | Leu | Ala | Val | Ala | Val | Gly | Leu | Pro | Arg | Lys | |
| 465 | | | | 470 | | | | | 475 | | | | | 480 | | |
| agg | agc | tga | aaagagtgaa | tgtgacattg | gcttcaaaca | cagctcacct | | | | | | | | | | 1489 |
| Arg | Ser | | | | | | | | | | | | | | | |

| | |
|---|---|
| gagactgatt tcttctgaac aaaacaagcg tgtgatccat ggacattcag gcagccagat | 1549 |
| atcccacaga gatctgacta tctgctctat gggccagagg gaactcctgt cagggagctg | 1609 |
| gtactgagag gtggagactg ggaacagggc gcgatgggtc ccggaggttg ccaagcacat | 1669 |
| gttgcaaaga aagagtcatc tctgtgtcac ctgacagtga gttttaggca atggattgca | 1729 |
| aaagaaatga gttctgggcc atcccctctc ttccaagccc catcccttg aaggtggccc | 1789 |
| ctgaacaagt cagaatcccc ctgaccgtgc ctctgaatac ctctcctcct ataacatgat | 1849 |
| tggcaagtgc cctatctaca ccttccccaa aacttccttc tctgggactc tgcaccccgc | 1909 |
| ttcattcttt ggttccctaa tgtaggttct ctggacattt tttctgtacc cacaagaaca | 1969 |
| tctccaacgt atcaggaaaa taacaatctg ggattctgga aa | 2011 |

<210> SEQ ID NO 4
<211> LENGTH: 482
<212> TYPE: PRT
<213> ORGANISM: Homo sapiens

<400> SEQUENCE: 4

Met Val Asp Phe Pro Gly Tyr Asn Leu Ser Gly Ala Val Ala Ser Phe
1               5                   10                  15

Leu Phe Ile Leu Leu Thr Met Lys Gln Ser Glu Asp Phe Arg Val Ile
                20                  25                  30

Gly Pro Ala His Pro Ile Leu Ala Gly Val Gly Glu Asp Ala Leu Leu
            35                  40                  45

Thr Cys Gln Leu Leu Pro Lys Arg Thr Thr Met His Val Glu Val Arg
        50                  55                  60

Trp Tyr Arg Ser Glu Pro Ser Thr Pro Val Phe Val His Arg Asp Gly
65                  70                  75                  80

Val Glu Val Thr Glu Met Gln Met Glu Glu Tyr Arg Gly Trp Val Glu
                85                  90                  95

Trp Ile Glu Asn Gly Ile Ala Lys Gly Asn Val Ala Leu Lys Ile His
                100                 105                 110

```
Asn Ile Gln Pro Ser Asp Asn Gly Gln Tyr Trp Cys His Phe Gln Asp
        115                 120                 125

Gly Asn Tyr Cys Gly Glu Thr Ser Leu Leu Lys Val Ala Gly Leu
    130                 135                 140

Gly Ser Ala Pro Ser Ile His Met Glu Gly Pro Gly Glu Ser Gly Val
145                 150                 155                 160

Gln Leu Val Cys Thr Ala Arg Gly Trp Phe Pro Glu Pro Gln Val Tyr
            165                 170                 175

Trp Glu Asp Ile Arg Gly Glu Lys Leu Leu Ala Val Ser Glu His Arg
            180                 185                 190

Ile Gln Asp Lys Asp Gly Leu Phe Tyr Ala Glu Ala Thr Leu Val Val
        195                 200                 205

Arg Asn Ala Ser Ala Glu Ser Val Ser Cys Leu Val His Asn Pro Val
    210                 215                 220

Leu Thr Glu Glu Lys Gly Ser Val Ile Ser Leu Pro Glu Lys Leu Gln
225                 230                 235                 240

Thr Glu Leu Ala Ser Leu Lys Val Asn Gly Pro Ser Gln Pro Ile Leu
            245                 250                 255

Val Arg Val Gly Glu Asp Ile Gln Leu Thr Cys Tyr Leu Ser Pro Lys
            260                 265                 270

Ala Asn Ala Gln Ser Met Glu Val Arg Trp Asp Arg Ser His Arg Tyr
        275                 280                 285

Pro Ala Val His Val Tyr Met Asp Gly Asp His Val Ala Gly Glu Gln
    290                 295                 300

Met Ala Glu Tyr Arg Gly Arg Thr Val Leu Val Ser Asp Ala Ile Asp
305                 310                 315                 320

Glu Gly Arg Leu Thr Leu Gln Ile Leu Ser Ala Arg Pro Ser Asp Asp
            325                 330                 335

Gly Gln Tyr Arg Cys Leu Phe Glu Lys Asp Asp Val Tyr Gln Glu Ala
            340                 345                 350

Ser Leu Asp Leu Lys Val Val Gly Leu Gly Ser Ser Pro Leu Ile Thr
        355                 360                 365

Val Glu Gly Gln Glu Asp Gly Glu Met Gln Pro Met Cys Ser Ser Asp
    370                 375                 380

Gly Trp Phe Pro Gln Pro His Val Pro Trp Arg Asp Met Glu Gly Lys
385                 390                 395                 400

Thr Ile Pro Ser Ser Ser Gln Ala Leu Thr Gln Gly Ser His Gly Leu
            405                 410                 415

Phe His Val Gln Thr Leu Leu Arg Val Thr Asn Ile Ser Ala Val Asp
        420                 425                 430

Val Thr Cys Ser Ile Ser Ile Pro Phe Leu Gly Glu Glu Lys Ile Ala
    435                 440                 445

Thr Phe Ser Leu Ser Glu Ser Arg Met Thr Phe Leu Trp Lys Thr Leu
450                 455                 460

Leu Val Trp Gly Leu Leu Leu Ala Val Ala Val Gly Leu Pro Arg Lys
            470                 475                 480

Arg Ser

<210> SEQ ID NO 5
<211> LENGTH: 2300
<212> TYPE: DNA
<213> ORGANISM: Mus sp.
<220> FEATURE:
<221> NAME/KEY: CDS
<222> LOCATION: (1)..(1545)
```

```
<400> SEQUENCE: 5 atg gtg gat tgc cca cgg tat agt cta tct ggc gtg gct gcc tcc ttc      48
Met Val Asp Cys Pro Arg Tyr Ser Leu Ser Gly Val Ala Ala Ser Phe
1               5                   10                  15 ctc ttc gtc ctg ctg act ata aag cac cca gat gac ttc aga gtg gtc      96
Leu Phe Val Leu Leu Thr Ile Lys His Pro Asp Asp Phe Arg Val Val
            20                  25                  30 ggt cct aac ctc cca atc ctg gct aaa gtc ggg gaa gat gcc ctg cta     144
Gly Pro Asn Leu Pro Ile Leu Ala Lys Val Gly Glu Asp Ala Leu Leu
        35                  40                  45 acg tgt cag ctc ctc ccc aag agg acc acg gca cac atg gag gtg agg     192
Thr Cys Gln Leu Leu Pro Lys Arg Thr Thr Ala His Met Glu Val Arg
    50                  55                  60 tgg tac cgc tcc gac cct gcc atg cca gtg att atg tac cgg gat gga     240
Trp Tyr Arg Ser Asp Pro Ala Met Pro Val Ile Met Tyr Arg Asp Gly
65                  70                  75                  80 gct gtg gtg act ggg cta ccg atg gag ggg tac gga ggc cgg gca gag     288
Ala Val Val Thr Gly Leu Pro Met Glu Gly Tyr Gly Gly Arg Ala Glu
                85                  90                  95 tgg atg gag gac agc act gaa gag ggc agt gtg gct ctg aag att cgc     336
Trp Met Glu Asp Ser Thr Glu Glu Gly Ser Val Ala Leu Lys Ile Arg
            100                 105                 110 cag gtc cag cca agt gac gat ggc cag tac tgg tgc cgc ttc cag gag     384
Gln Val Gln Pro Ser Asp Asp Gly Gln Tyr Trp Cys Arg Phe Gln Glu
        115                 120                 125 ggg gac tac tgg aga gag aca agc gtg cta ctc caa gtg gct gct cta     432
Gly Asp Tyr Trp Arg Glu Thr Ser Val Leu Leu Gln Val Ala Ala Leu
    130                 135                 140 gga tct tcc cca aat atc cat gtg gag gga ctt gga gaa gga gag gtc     480
Gly Ser Ser Pro Asn Ile His Val Glu Gly Leu Gly Glu Gly Glu Val
145                 150                 155                 160 caa ctt gta tgc acg tcc cga ggc tgg ttc cct gag cct gag gtg cac     528
Gln Leu Val Cys Thr Ser Arg Gly Trp Phe Pro Glu Pro Glu Val His
                165                 170                 175 tgg gaa ggc atc tgg gga gaa aag ttg atg agt ttc tct gag aat cat     576
Trp Glu Gly Ile Trp Gly Glu Lys Leu Met Ser Phe Ser Glu Asn His
            180                 185                 190 gtg cca ggt gaa gat ggg cta ttc tat gtg gaa gac aca ctg atg gtc     624
Val Pro Gly Glu Asp Gly Leu Phe Tyr Val Glu Asp Thr Leu Met Val
        195                 200                 205 agg aat gac agt gta gag acc att tcc tgc ttc atc tac agc cat ggc     672
Arg Asn Asp Ser Val Glu Thr Ile Ser Cys Phe Ile Tyr Ser His Gly
    210                 215                 220 ctc aga gag acc cag gag gcc acc atc gct ctg tca gag agg ctc cag     720
Leu Arg Glu Thr Gln Glu Ala Thr Ile Ala Leu Ser Glu Arg Leu Gln
225                 230                 235                 240 acc gaa ctg gtt tcc gtt agc gta atc gga cat tcc cag ccc agc cct     768
Thr Glu Leu Val Ser Val Ser Val Ile Gly His Ser Gln Pro Ser Pro
                245                 250                 255 gtt caa gtc gga gag aac ata gaa tta act tgt cac ctc tca cct caa     816
Val Gln Val Gly Glu Asn Ile Glu Leu Thr Cys His Leu Ser Pro Gln
            260                 265                 270 acg gat gct cag aac tta gag gtg agg tgg ctc cga tcc cgc tat tac     864
Thr Asp Ala Gln Asn Leu Glu Val Arg Trp Leu Arg Ser Arg Tyr Tyr
        275                 280                 285 cct gca gtc cac gtg tat gca aat ggc acc cac gtg gct gga gag cag     912
Pro Ala Val His Val Tyr Ala Asn Gly Thr His Val Ala Gly Glu Gln
    290                 295                 300
```

```
                                                          -continued atg gta gaa tac aaa ggg agg act tca ttg gtg act gat gcc atc cac      960
Met Val Glu Tyr Lys Gly Arg Thr Ser Leu Val Thr Asp Ala Ile His
305             310                 315                 320 gag gga aaa ctg acc ctg cag att cac aat gcc aga act tcg gat gaa     1008
Glu Gly Lys Leu Thr Leu Gln Ile His Asn Ala Arg Thr Ser Asp Glu
            325                 330                 335 ggg cag tac cgg tgc ctt ttt gga aaa gat ggt gtc tac cag gag gcc     1056
Gly Gln Tyr Arg Cys Leu Phe Gly Lys Asp Gly Val Tyr Gln Glu Ala
340                 345                 350 cgt gtg gat gtg cag gtg acg gcg gtg ggt tcc acc cca cgg atc acc     1104
Arg Val Asp Val Gln Val Thr Ala Val Gly Ser Thr Pro Arg Ile Thr
        355                 360                 365 agg gag gtc ttg aaa gat gga ggc atg cag ctg agg tgt acg tct gat     1152
Arg Glu Val Leu Lys Asp Gly Gly Met Gln Leu Arg Cys Thr Ser Asp
370                 375                 380 ggg tgg ttc cca cgg ccc cat gtg cag tgg agg gac aga gat gga aag     1200
Gly Trp Phe Pro Arg Pro His Val Gln Trp Arg Asp Arg Asp Gly Lys
385                 390                 395                 400 aca atg cca tcg ttt tcc gag gcc ttt cag caa ggg agc cag gag ctg     1248
Thr Met Pro Ser Phe Ser Glu Ala Phe Gln Gln Gly Ser Gln Glu Leu
                405                 410                 415 ttc cag gtg gag aca ctt ctg ctg gtc aca aac ggc tcc atg gtg aat     1296
Phe Gln Val Glu Thr Leu Leu Leu Val Thr Asn Gly Ser Met Val Asn
            420                 425                 430 gtg acc tgc tcc atc agc ctc cct ctg ggc cag gag aaa aca gcc cgt     1344
Val Thr Cys Ser Ile Ser Leu Pro Leu Gly Gln Glu Lys Thr Ala Arg
        435                 440                 445 ttc cct ctc tca gac tcc aag ata gct ttg tta tgg atg acc ctg cct     1392
Phe Pro Leu Ser Asp Ser Lys Ile Ala Leu Leu Trp Met Thr Leu Pro
450                 455                 460 gtt gtg gtg ctg cct ctc gcc atg gct atg gac ctg atc aag gtg aaa     1440
Val Val Val Leu Pro Leu Ala Met Ala Met Asp Leu Ile Lys Val Lys
465                 470                 475                 480 cgg cgg cga cgg acc aat gaa caa aca cac agc agc aat cag gaa aat     1488
Arg Arg Arg Arg Thr Asn Glu Gln Thr His Ser Ser Asn Gln Glu Asn
                485                 490                 495 aac aag aat gac gaa aac cac agg cgg cga ctt cct tct gac gag agg     1536
Asn Lys Asn Asp Glu Asn His Arg Arg Arg Leu Pro Ser Asp Glu Arg
            500                 505                 510 ctc aga tga aaatgcaccc cgcaagccca acgcacccca tttcctgaac              1585
Leu Arg acccatccc tcctcccatc ttttcccctc aataagctgc actgacatag gagtggtttc    1645
acttgctact ctccaaaggt tcttcatgga ccctgtccgt acctgatgca accatcacgc    1705
acagttggga gcacctcgac ctgagccaac ccacaatagt cttgatccct ccctcacagt    1765
gatggcatct tctctccctt tgtctctttc tgctgtccct caatctaggg actatccctt    1825
gcctgtgcac agcatcttta tctcatcacc ttctggaccc accatgagga tggaagaact    1885
tagacctgca gagaaatgtc acccatctga gtcctggatg ggttttctta gaaatgccca    1945
atccagtagc actagaggga caaagcaggt gggaggagag ggtttctttc ctccgtcctc    2005
aagagaaagg actaactgtg attcacagtt acaaagacc tgacacttgc tctacaaatc     2065
agaccggggg tgggggaatt gtagaaataa ctaagggggt aaaagcactt gctgttcttg    2125
cagaggacct gagtttcatt cccagcacct gtatggcagg tcataatcat ctatatctcc    2185
agttctaggg ggtcagatgc ccttttctag cctctgaggg caccaggcac acatgtggca    2245
cacagacata gatgtaggca aaacacccat acatctaaaa taaaaataat tttta         2300
```

```
<210> SEQ ID NO 6
<211> LENGTH: 514
<212> TYPE: PRT
<213> ORGANISM: Mus sp.

<400> SEQUENCE: 6
```

| | | | | | | | | | | | | | | | |
|---|---|---|---|---|---|---|---|---|---|---|---|---|---|---|---|
| Met | Val | Asp | Cys | Pro | Arg | Tyr | Ser | Leu | Ser | Gly | Val | Ala | Ala | Ser | Phe |
| 1 | | | | 5 | | | | | 10 | | | | | 15 | |
| Leu | Phe | Val | Leu | Leu | Thr | Ile | Lys | His | Pro | Asp | Asp | Phe | Arg | Val | Val |
| | | | 20 | | | | | 25 | | | | | 30 | | |
| Gly | Pro | Asn | Leu | Pro | Ile | Leu | Ala | Lys | Val | Gly | Glu | Asp | Ala | Leu | Leu |
| | | 35 | | | | | 40 | | | | | 45 | | | |
| Thr | Cys | Gln | Leu | Leu | Pro | Lys | Arg | Thr | Thr | Ala | His | Met | Glu | Val | Arg |
| 50 | | | | | 55 | | | | | 60 | | | | | |
| Trp | Tyr | Arg | Ser | Asp | Pro | Ala | Met | Pro | Val | Ile | Met | Tyr | Arg | Asp | Gly |
| 65 | | | | | 70 | | | | | 75 | | | | | 80 |
| Ala | Val | Val | Thr | Gly | Leu | Pro | Met | Glu | Gly | Tyr | Gly | Gly | Arg | Ala | Glu |
| | | | | 85 | | | | | 90 | | | | | 95 | |
| Trp | Met | Glu | Asp | Ser | Thr | Glu | Glu | Gly | Ser | Val | Ala | Leu | Lys | Ile | Arg |
| | | | 100 | | | | | 105 | | | | | 110 | | |
| Gln | Val | Gln | Pro | Ser | Asp | Asp | Gly | Gln | Tyr | Trp | Cys | Arg | Phe | Gln | Glu |
| | | 115 | | | | | 120 | | | | | 125 | | | |
| Gly | Asp | Tyr | Trp | Arg | Glu | Thr | Ser | Val | Leu | Leu | Gln | Val | Ala | Ala | Leu |
| | 130 | | | | | 135 | | | | | 140 | | | | |
| Gly | Ser | Ser | Pro | Asn | Ile | His | Val | Glu | Gly | Leu | Gly | Glu | Gly | Glu | Val |
| 145 | | | | | 150 | | | | | 155 | | | | | 160 |
| Gln | Leu | Val | Cys | Thr | Ser | Arg | Gly | Trp | Phe | Pro | Glu | Pro | Glu | Val | His |
| | | | | 165 | | | | | 170 | | | | | 175 | |
| Trp | Glu | Gly | Ile | Trp | Gly | Glu | Lys | Leu | Met | Ser | Phe | Ser | Glu | Asn | His |
| | | | 180 | | | | | 185 | | | | | 190 | | |
| Val | Pro | Gly | Glu | Asp | Gly | Leu | Phe | Tyr | Val | Glu | Asp | Thr | Leu | Met | Val |
| | | 195 | | | | | 200 | | | | | 205 | | | |
| Arg | Asn | Asp | Ser | Val | Glu | Thr | Ile | Ser | Cys | Phe | Ile | Tyr | Ser | His | Gly |
| | 210 | | | | | 215 | | | | | 220 | | | | |
| Leu | Arg | Glu | Thr | Gln | Glu | Ala | Thr | Ile | Ala | Leu | Ser | Glu | Arg | Leu | Gln |
| 225 | | | | | 230 | | | | | 235 | | | | | 240 |
| Thr | Glu | Leu | Val | Ser | Val | Ser | Val | Ile | Gly | His | Ser | Gln | Pro | Ser | Pro |
| | | | | 245 | | | | | 250 | | | | | 255 | |
| Val | Gln | Val | Gly | Glu | Asn | Ile | Glu | Leu | Thr | Cys | His | Leu | Ser | Pro | Gln |
| | | | 260 | | | | | 265 | | | | | 270 | | |
| Thr | Asp | Ala | Gln | Asn | Leu | Glu | Val | Arg | Trp | Leu | Arg | Ser | Arg | Tyr | Tyr |
| | | 275 | | | | | 280 | | | | | 285 | | | |
| Pro | Ala | Val | His | Val | Tyr | Ala | Asn | Gly | Thr | His | Val | Ala | Gly | Glu | Gln |
| | 290 | | | | | 295 | | | | | 300 | | | | |
| Met | Val | Glu | Tyr | Lys | Gly | Arg | Thr | Ser | Leu | Val | Thr | Asp | Ala | Ile | His |
| 305 | | | | | 310 | | | | | 315 | | | | | 320 |
| Glu | Gly | Lys | Leu | Thr | Leu | Gln | Ile | His | Asn | Ala | Arg | Thr | Ser | Asp | Glu |
| | | | | 325 | | | | | 330 | | | | | 335 | |
| Gly | Gln | Tyr | Arg | Cys | Leu | Phe | Gly | Lys | Asp | Gly | Val | Tyr | Gln | Glu | Ala |
| | | | 340 | | | | | 345 | | | | | 350 | | |
| Arg | Val | Asp | Val | Gln | Val | Thr | Ala | Val | Gly | Ser | Thr | Pro | Arg | Ile | Thr |
| | | 355 | | | | | 360 | | | | | 365 | | | |
| Arg | Glu | Val | Leu | Lys | Asp | Gly | Gly | Met | Gln | Leu | Arg | Cys | Thr | Ser | Asp |
| | 370 | | | | | 375 | | | | | 380 | | | | |

```
Gly Trp Phe Pro Arg Pro His Val Gln Trp Arg Asp Arg Asp Gly Lys
385                 390                 395                 400

Thr Met Pro Ser Phe Ser Glu Ala Phe Gln Gln Gly Ser Gln Glu Leu
            405                 410                 415

Phe Gln Val Glu Thr Leu Leu Val Thr Asn Gly Ser Met Val Asn
        420                 425                 430

Val Thr Cys Ser Ile Ser Leu Pro Leu Gly Gln Glu Lys Thr Ala Arg
        435                 440                 445

Phe Pro Leu Ser Asp Ser Lys Ile Ala Leu Leu Trp Met Thr Leu Pro
    450                 455                 460

Val Val Val Leu Pro Leu Ala Met Ala Met Asp Leu Ile Lys Val Lys
465                 470                 475                 480

Arg Arg Arg Arg Thr Asn Glu Gln Thr His Ser Ser Asn Gln Glu Asn
                485                 490                 495

Asn Lys Asn Asp Glu Asn His Arg Arg Arg Leu Pro Ser Asp Glu Arg
            500                 505                 510

Leu Arg

<210> SEQ ID NO 7
<211> LENGTH: 1012
<212> TYPE: DNA
<213> ORGANISM: Homo sapiens
<220> FEATURE:
<221> NAME/KEY: CDS
<222> LOCATION: (1)..(819)

<400> SEQUENCE: 7 atg gtg gat ttt cca ggc tac aat ctg tct ggt gca gtc gcc tcc ttc      48
Met Val Asp Phe Pro Gly Tyr Asn Leu Ser Gly Ala Val Ala Ser Phe
1               5                   10                  15 cta ttc atc ctg ctg aca atg aag cag tca gag aaa ctc cag act gag      96
Leu Phe Ile Leu Leu Thr Met Lys Gln Ser Glu Lys Leu Gln Thr Glu
            20                  25                  30 ctg gct tct tta aaa gtg aat gga cct tcc cag ccc atc ctc gtc aga     144
Leu Ala Ser Leu Lys Val Asn Gly Pro Ser Gln Pro Ile Leu Val Arg
        35                  40                  45 gtg gga gaa gat ata cag cta acc tgt tac ctg tcc ccc aag gcg aat     192
Val Gly Glu Asp Ile Gln Leu Thr Cys Tyr Leu Ser Pro Lys Ala Asn
    50                  55                  60 gca cag agc atg gag gtg agg tgg gac cga tcc cac cgt tac cct gct     240
Ala Gln Ser Met Glu Val Arg Trp Asp Arg Ser His Arg Tyr Pro Ala
65                  70                  75                  80 gtg cat gtg tat atg gat ggg gac cat gtg gct gga gag cag atg gca     288
Val His Val Tyr Met Asp Gly Asp His Val Ala Gly Glu Gln Met Ala
                85                  90                  95 gag tac aga ggg agg act gtg ctg gtg agt gac gcc att gac gag ggc     336
Glu Tyr Arg Gly Arg Thr Val Leu Val Ser Asp Ala Ile Asp Glu Gly
            100                 105                 110 aga ctg acc ctg cag ata ctc agt gcc aga cct tcg gac gac ggg cag     384
Arg Leu Thr Leu Gln Ile Leu Ser Ala Arg Pro Ser Asp Asp Gly Gln
        115                 120                 125 tac cgc tgc ctt ttt gaa aaa gat gat gtc tac caa gag gcc agt ttg     432
Tyr Arg Cys Leu Phe Glu Lys Asp Asp Val Tyr Gln Glu Ala Ser Leu
    130                 135                 140 gat ctg aag gtg gta ggt ctg ggt tct tcc cca ctg atc act gtg gag     480
Asp Leu Lys Val Val Gly Leu Gly Ser Ser Pro Leu Ile Thr Val Glu
145                 150                 155                 160
```

```
ggg caa gaa gat gga gaa atg cag ccg atg tgc tct tca gat ggg tgg       528
Gly Gln Glu Asp Gly Glu Met Gln Pro Met Cys Ser Ser Asp Gly Trp
                165                 170                 175 ttc cca cag ccc cac gtg cca tgg agg gac atg gaa gga aag acg ata       576
Phe Pro Gln Pro His Val Pro Trp Arg Asp Met Glu Gly Lys Thr Ile
            180                 185                 190 cca tca tct tcc cag gcc ctg act caa ggc agc cac ggg ctg ttc cac       624
Pro Ser Ser Ser Gln Ala Leu Thr Gln Gly Ser His Gly Leu Phe His
        195                 200                 205 gtg cag aca ttg cta agg gtc aca aac atc tcc gct gtg gac gtc act       672
Val Gln Thr Leu Leu Arg Val Thr Asn Ile Ser Ala Val Asp Val Thr
    210                 215                 220 tgt tcc atc agc atc ccc ttt ttg ggc gag gag aaa atc gca act ttt       720
Cys Ser Ile Ser Ile Pro Phe Leu Gly Glu Glu Lys Ile Ala Thr Phe
225                 230                 235                 240 tct ctc tca gag tcc agg atg acg ttt ttg tgg aaa aca ctg ctt gtt       768
Ser Leu Ser Glu Ser Arg Met Thr Phe Leu Trp Lys Thr Leu Leu Val
                245                 250                 255 tgg gga ttg ctt ctt gct gtg gct gta ggc ctg ccc agg aag agg agc       816
Trp Gly Leu Leu Leu Ala Val Ala Val Gly Leu Pro Arg Lys Arg Ser
            260                 265                 270 tga aaagagtgaa tgtgacattg gcttcaaaca cagctcacct gagactgatt            869
tcttctgaac aaaacaagcg tgtgatccat ggacattcag gcagccagat atcccacaga    929
gatctgacta tctgctctat gggccagagg gaactcctgt cagggagctg gtactgagag    989
gtggagactg ggaacagggc gcg                                            1012

<210> SEQ ID NO 8
<211> LENGTH: 272
<212> TYPE: PRT
<213> ORGANISM: Homo sapiens

<400> SEQUENCE: 8

Met Val Asp Phe Pro Gly Tyr Asn Leu Ser Gly Ala Val Ala Ser Phe
1               5                   10                  15

Leu Phe Ile Leu Leu Thr Met Lys Gln Ser Glu Lys Leu Gln Thr Glu
            20                  25                  30

Leu Ala Ser Leu Lys Val Asn Gly Pro Ser Gln Pro Ile Leu Val Arg
        35                  40                  45

Val Gly Glu Asp Ile Gln Leu Thr Cys Tyr Leu Ser Pro Lys Ala Asn
    50                  55                  60

Ala Gln Ser Met Glu Val Arg Trp Asp Arg Ser His Arg Tyr Pro Ala
65                  70                  75                  80

Val His Val Tyr Met Asp Gly Asp His Val Ala Gly Glu Gln Met Ala
                85                  90                  95

Glu Tyr Arg Gly Arg Thr Val Leu Val Ser Asp Ala Ile Asp Glu Gly
            100                 105                 110

Arg Leu Thr Leu Gln Ile Leu Ser Ala Arg Pro Ser Asp Asp Gly Gln
        115                 120                 125

Tyr Arg Cys Leu Phe Glu Lys Asp Asp Val Tyr Gln Glu Ala Ser Leu
    130                 135                 140

Asp Leu Lys Val Val Gly Leu Gly Ser Ser Pro Leu Ile Thr Val Glu
145                 150                 155                 160

Gly Gln Glu Asp Gly Glu Met Gln Pro Met Cys Ser Ser Asp Gly Trp
                165                 170                 175

Phe Pro Gln Pro His Val Pro Trp Arg Asp Met Glu Gly Lys Thr Ile
            180                 185                 190
```

```
                                          -continued

Pro Ser Ser Ser Gln Ala Leu Thr Gln Gly Ser His Gly Leu Phe His
            195                 200                 205

Val Gln Thr Leu Leu Arg Val Thr Asn Ile Ser Ala Val Asp Val Thr
    210                 215                 220

Cys Ser Ile Ser Ile Pro Phe Leu Gly Glu Lys Ile Ala Thr Phe
225                 230                 235                 240

Ser Leu Ser Glu Ser Arg Met Thr Phe Leu Trp Lys Thr Leu Leu Val
                245                 250                 255

Trp Gly Leu Leu Leu Ala Val Ala Val Gly Leu Pro Arg Lys Arg Ser
            260                 265                 270

<210> SEQ ID NO 9
<211> LENGTH: 1336
<212> TYPE: DNA
<213> ORGANISM: Homo sapiens
<220> FEATURE:
<221> NAME/KEY: CDS
<222> LOCATION: (1)..(1167)

<400> SEQUENCE: 9 atg gtg gat ttt cca ggc tac aat ctg tct ggt gca gtc gcc tcc ttc      48
Met Val Asp Phe Pro Gly Tyr Asn Leu Ser Gly Ala Val Ala Ser Phe
1               5                   10                  15 cta ttc atc ctg ctg aca atg aag cag tca gaa gac ttt aga gtc att      96
Leu Phe Ile Leu Leu Thr Met Lys Gln Ser Glu Asp Phe Arg Val Ile
                20                  25                  30 ggc cct gct cat cct atc ctg gcc ggg gtt ggg gaa gat gcc ctg tta     144
Gly Pro Ala His Pro Ile Leu Ala Gly Val Gly Glu Asp Ala Leu Leu
            35                  40                  45 acc tgc cag cta ctc ccc aag agg acc aca atg cac gtg gag gtg agg     192
Thr Cys Gln Leu Leu Pro Lys Arg Thr Thr Met His Val Glu Val Arg
        50                  55                  60 tgg tac cgc tca gag ccc agc aca cct gtg ttt gtg cac agg gat gga     240
Trp Tyr Arg Ser Glu Pro Ser Thr Pro Val Phe Val His Arg Asp Gly
65                  70                  75                  80 gtg gag gtg act gag atg cag atg gag gag tac aga ggc tgg gta gag     288
Val Glu Val Thr Glu Met Gln Met Glu Glu Tyr Arg Gly Trp Val Glu
                85                  90                  95 tgg ata gag aat ggc att gca aag gga aat gtg gca ctg aag ata cac     336
Trp Ile Glu Asn Gly Ile Ala Lys Gly Asn Val Ala Leu Lys Ile His
            100                 105                 110 aac atc cag ccc tcc gac aat gga caa tac tgg tgc cat ttc cag gat     384
Asn Ile Gln Pro Ser Asp Asn Gly Gln Tyr Trp Cys His Phe Gln Asp
        115                 120                 125 ggg aac tac tgt gga gaa aca agc ttg ctg ctc aaa gta gca gag aaa     432
Gly Asn Tyr Cys Gly Glu Thr Ser Leu Leu Leu Lys Val Ala Glu Lys
    130                 135                 140 ctc cag act gag ctg gct tct tta aaa gtg aat gga cct tcc cag ccc     480
Leu Gln Thr Glu Leu Ala Ser Leu Lys Val Asn Gly Pro Ser Gln Pro
145                 150                 155                 160 atc ctc gtc aga gtg gga gaa gat ata cag cta acc tgt tac ctg tcc     528
Ile Leu Val Arg Val Gly Glu Asp Ile Gln Leu Thr Cys Tyr Leu Ser
                165                 170                 175 ccc aag gcg aat gca cag agc atg gag gtg agg tgg gac cga tcc cac     576
Pro Lys Ala Asn Ala Gln Ser Met Glu Val Arg Trp Asp Arg Ser His
            180                 185                 190 cgt tac cct gct gtg cat gtg tat atg gat ggg gac cat gtg gct gga     624
Arg Tyr Pro Ala Val His Val Tyr Met Asp Gly Asp His Val Ala Gly
        195                 200                 205
```

```
gag cag atg gca gag tac aga ggg agg act gtg ctg gtg agt gac gcc      672
Glu Gln Met Ala Glu Tyr Arg Gly Arg Thr Val Leu Val Ser Asp Ala
    210                 215                 220 att gac gag ggc aga ctg acc ctg cag ata ctc agt gcc aga cct tcg      720
Ile Asp Glu Gly Arg Leu Thr Leu Gln Ile Leu Ser Ala Arg Pro Ser
225                 230                 235                 240 gac gac ggg cag tac cgc tgc ctt ttt gaa aaa gat gat gtc tac caa      768
Asp Asp Gly Gln Tyr Arg Cys Leu Phe Glu Lys Asp Asp Val Tyr Gln
                245                 250                 255 gag gcc agt ttg gat ctg aag gtg gta ggt ctg ggt tct tcc cca ctg      816
Glu Ala Ser Leu Asp Leu Lys Val Val Gly Leu Gly Ser Ser Pro Leu
            260                 265                 270 atc act gtg gag ggg caa gaa gat gga gaa atg cag ccg atg tgc tct      864
Ile Thr Val Glu Gly Gln Glu Asp Gly Glu Met Gln Pro Met Cys Ser
        275                 280                 285 tca gat ggg tgg ttc cca cag ccc cac gtg cca tgg agg gac atg gaa      912
Ser Asp Gly Trp Phe Pro Gln Pro His Val Pro Trp Arg Asp Met Glu
    290                 295                 300 gga aag acg ata cca tca tct tcc cag gcc ctg act caa ggc agc cac      960
Gly Lys Thr Ile Pro Ser Ser Ser Gln Ala Leu Thr Gln Gly Ser His
305                 310                 315                 320 ggg ctg ttc cac gtg cag aca ttg cta agg gtc aca aac atc tcc gct     1008
Gly Leu Phe His Val Gln Thr Leu Leu Arg Val Thr Asn Ile Ser Ala
                325                 330                 335 gtg gac gtc act tgt tcc atc agc atc ccc ttt ttg ggc gag gag aaa     1056
Val Asp Val Thr Cys Ser Ile Ser Ile Pro Phe Leu Gly Glu Glu Lys
            340                 345                 350 atc gca act ttt tct ctc tca gag tcc agg atg acg ttt ttg tgg aaa     1104
Ile Ala Thr Phe Ser Leu Ser Glu Ser Arg Met Thr Phe Leu Trp Lys
        355                 360                 365 aca ctg ctt gtt tgg gga ttg ctt ctt gct gtg gct gta ggc ctg ccc     1152
Thr Leu Leu Val Trp Gly Leu Leu Leu Ala Val Ala Val Gly Leu Pro
    370                 375                 380 agg aag agg agc tga aaagagtgaa tgtgacattg gcttcaaaca cagctcacct    1207
Arg Lys Arg Ser
385 gagactgatt tcttctgaac aaaacaagcg tgtgatccat ggacattcag gcagccagat  1267 atcccacaga gatctgacta tctgctctat gggccagagg gaactcctgt cagggagctg  1327 gtactgaga                                                          1336

<210> SEQ ID NO 10
<211> LENGTH: 388
<212> TYPE: PRT
<213> ORGANISM: Homo sapiens

<400> SEQUENCE: 10

Met Val Asp Phe Pro Gly Tyr Asn Leu Ser Gly Ala Val Ala Ser Phe
1               5                   10                  15

Leu Phe Ile Leu Leu Thr Met Lys Gln Ser Glu Asp Phe Arg Val Ile
                20                  25                  30

Gly Pro Ala His Pro Ile Leu Ala Gly Val Gly Glu Asp Ala Leu Leu
            35                  40                  45

Thr Cys Gln Leu Leu Pro Lys Arg Thr Thr Met His Val Glu Val Arg
        50                  55                  60

Trp Tyr Arg Ser Glu Pro Ser Thr Pro Val Phe Val His Arg Asp Gly
65                  70                  75                  80

Val Glu Val Thr Glu Met Gln Met Glu Glu Tyr Arg Gly Trp Val Glu
                85                  90                  95
```

Trp Ile Glu Asn Gly Ile Ala Lys Gly Asn Val Ala Leu Lys Ile His
            100                 105                 110

Asn Ile Gln Pro Ser Asp Asn Gly Gln Tyr Trp Cys His Phe Gln Asp
        115                 120                 125

Gly Asn Tyr Cys Gly Glu Thr Ser Leu Leu Lys Val Ala Glu Lys
    130                 135                 140

Leu Gln Thr Glu Leu Ala Ser Leu Lys Val Asn Gly Pro Ser Gln Pro
145                 150                 155                 160

Ile Leu Val Arg Val Gly Glu Asp Ile Gln Leu Thr Cys Tyr Leu Ser
                165                 170                 175

Pro Lys Ala Asn Ala Gln Ser Met Glu Val Arg Trp Asp Arg Ser His
            180                 185                 190

Arg Tyr Pro Ala Val His Val Tyr Met Asp Gly Asp His Val Ala Gly
        195                 200                 205

Glu Gln Met Ala Glu Tyr Arg Gly Arg Thr Val Leu Val Ser Asp Ala
    210                 215                 220

Ile Asp Glu Gly Arg Leu Thr Leu Gln Ile Leu Ser Ala Arg Pro Ser
225                 230                 235                 240

Asp Asp Gly Gln Tyr Arg Cys Leu Phe Glu Lys Asp Asp Val Tyr Gln
                245                 250                 255

Glu Ala Ser Leu Asp Leu Lys Val Val Gly Leu Gly Ser Ser Pro Leu
            260                 265                 270

Ile Thr Val Glu Gly Gln Glu Asp Gly Glu Met Gln Pro Met Cys Ser
        275                 280                 285

Ser Asp Gly Trp Phe Pro Gln Pro His Val Pro Trp Arg Asp Met Glu
    290                 295                 300

Gly Lys Thr Ile Pro Ser Ser Gln Ala Leu Thr Gln Gly Ser His
305                 310                 315                 320

Gly Leu Phe His Val Gln Thr Leu Leu Arg Val Thr Asn Ile Ser Ala
                325                 330                 335

Val Asp Val Thr Cys Ser Ile Ser Ile Pro Phe Leu Gly Glu Glu Lys
            340                 345                 350

Ile Ala Thr Phe Ser Leu Ser Glu Ser Arg Met Thr Phe Leu Trp Lys
        355                 360                 365

Thr Leu Leu Val Trp Gly Leu Leu Leu Ala Val Ala Val Gly Leu Pro
    370                 375                 380

Arg Lys Arg Ser
385

<210> SEQ ID NO 11
<211> LENGTH: 730
<212> TYPE: DNA
<213> ORGANISM: Homo sapiens

<400> SEQUENCE: 11
atggtggatt ttccaggcta caatctgtct ggtgcagtcg cctccttcct attcatcctg      60
ctgacaatga agcagtcaga gaaactccag actgagctgg cttctttaaa agtgaatgga     120
ccttcccagc ccatcctcgt cagagtggga gaagatatac agctaacctg ttacctgtcc     180
cccaaggcga atgcacagag catggaggtg aggtgggacc gatcccaccg ttaccctgct     240
gtgcatgtgt atatggatgg gaccatgtg gctggagagc agatggcaga gtacagaggg     300
aggactgtgc tggtgagtga cgccattgac gagggcagac tgaccctgca gatactcagt     360
gccagacctt cggacgacgg gcagtaccgc tgcctttttg aaaaagatga tgtctaccag     420

```
gaggccagtt tggatctgaa ggtggtaggt ctgggttctt ccccactgat cactgtggag    480
gggcaagaag atggagaaat gcagctgata tgctcttcag atgggtggtt cccacagccc    540
cacgtgcagt ggagggacat ggaaggaaag acgataccat cctcttccca ggccctgact    600
caaggcagcc atgggctgtt ccacgtgcag acattgctaa gggtcacaaa catctccgct    660
gtggacgtca cttgttccat cagcatcccc ttttgggcg aggagaaaat cgcaactttt    720
tctctctcag                                                          730
```

<210> SEQ ID NO 12
<211> LENGTH: 243
<212> TYPE: PRT
<213> ORGANISM: Homo sapiens

<400> SEQUENCE: 12

```
Met Val Asp Phe Pro Gly Tyr Asn Leu Ser Gly Ala Val Ala Ser Phe
1               5                   10                  15

Leu Phe Ile Leu Leu Thr Met Lys Gln Ser Glu Lys Leu Gln Thr Glu
            20                  25                  30

Leu Ala Ser Leu Lys Val Asn Gly Pro Ser Gln Pro Ile Leu Val Arg
        35                  40                  45

Val Gly Glu Asp Ile Gln Leu Thr Cys Tyr Leu Ser Pro Lys Ala Asn
    50                  55                  60

Ala Gln Ser Met Glu Val Arg Trp Asp Arg Ser His Arg Tyr Pro Ala
65                  70                  75                  80

Val His Val Tyr Met Asp Gly Asp His Val Ala Gly Glu Gln Met Ala
                85                  90                  95

Glu Tyr Arg Gly Arg Thr Val Leu Val Ser Asp Ala Ile Asp Glu Gly
            100                 105                 110

Arg Leu Thr Leu Gln Ile Leu Ser Ala Arg Pro Ser Asp Asp Gly Gln
        115                 120                 125

Tyr Arg Cys Leu Phe Glu Lys Asp Asp Val Tyr Gln Glu Ala Ser Leu
    130                 135                 140

Asp Leu Lys Val Val Gly Leu Gly Ser Ser Pro Leu Ile Thr Val Glu
145                 150                 155                 160

Gly Gln Glu Asp Gly Glu Met Gln Leu Ile Cys Ser Ser Asp Gly Trp
                165                 170                 175

Phe Pro Gln Pro His Val Gln Trp Arg Asp Met Glu Gly Lys Thr Ile
            180                 185                 190

Pro Ser Ser Ser Gln Ala Leu Thr Gln Gly Ser His Gly Leu Phe His
        195                 200                 205

Val Gln Thr Leu Leu Arg Val Thr Asn Ile Ser Ala Val Asp Val Thr
    210                 215                 220

Cys Ser Ile Ser Ile Pro Phe Leu Gly Glu Glu Lys Ile Ala Thr Phe
225                 230                 235                 240

Ser Leu Ser
```

<210> SEQ ID NO 13
<211> LENGTH: 1078
<212> TYPE: DNA
<213> ORGANISM: Homo sapiens

<400> SEQUENCE: 13

```
atggtggatt ttccaggcta caatctgtct ggtgcagtcg cctccttcct attcatcctg    60
ctgacaatga agcagtcaga agactttaga gtcattggcc ctgctcatcc tatcctggcc    120
```

```
ggggttgggg aagatgccct gttaacctgc cagctactcc ccaagaggac cacaatgcac    180
gtggaggtga ggtggtaccg ctcagagccc agcacacctg tgtttgtgca cagggatgga    240
gtggaggtga ctgagatgca gatggaggag tacagaggct gggtagagtg gatagagaat    300
ggcattgcaa agggaaatgt ggcactgaag atacacaaca tccagccctc cgacaatgga    360
caatactggt gccatttcca ggatgggaac tactgtggag aaacaagctt gctgctcaaa    420
gtagcagaga aactccagac tgagctggct tctttaaaag tgaatggacc ttcccagccc    480
atcctcgtca gagtgggaga agatatacag ctaacctgtt acctgtcccc caaggcgaat    540
gcacagagca tggaggtgag gtgggaccga tcccaccgtt accctgctgt gcatgtgtat    600
atggatgggg accatgtggc tggagagcag atggcagagt acagagggag gactgtgctg    660
gtgagtgacg ccattgacga gggcagactg accctgcaga tactcagtgc cagaccttcg    720
gacgacgggc agtaccgctg cctttttgaa aaagatgatg tctaccagga ggccagtttg    780
gatctgaagg tggtaggtct gggttcttcc ccactgatca ctgtggaggg caagaagat    840 ggagaaatgc agctgatatg ctcttcagat gggtggttcc cacagcccca cgtgcagtgg    900
agggacatgg aaggaaagac gataccatcc tcttcccagg ccctgactca aggcagccat    960
gggctgttcc acgtgcagac attgctaagg gtcacaaaca tctccgctgt ggacgtcact    1020
tgttccatca gcatcccctt tttgggcgag gagaaaatcg caacttttc tctctcag    1078
```

<210> SEQ ID NO 14
<211> LENGTH: 359
<212> TYPE: PRT
<213> ORGANISM: Homo sapiens

<400> SEQUENCE: 14

```
Met Val Asp Phe Pro Gly Tyr Asn Leu Ser Gly Ala Val Ala Ser Phe
1               5                   10                  15

Leu Phe Ile Leu Leu Thr Met Lys Gln Ser Glu Asp Phe Arg Val Ile
            20                  25                  30

Gly Pro Ala His Pro Ile Leu Ala Gly Val Gly Glu Asp Ala Leu Leu
        35                  40                  45

Thr Cys Gln Leu Leu Pro Lys Arg Thr Thr Met His Val Glu Val Arg
    50                  55                  60

Trp Tyr Arg Ser Glu Pro Ser Thr Pro Val Phe His Arg Asp Gly
65                  70                  75                  80

Val Glu Val Thr Glu Met Gln Met Glu Glu Tyr Arg Gly Trp Val Glu
                85                  90                  95

Trp Ile Glu Asn Gly Ile Ala Lys Gly Asn Val Ala Leu Lys Ile His
            100                 105                 110

Asn Ile Gln Pro Ser Asp Asn Gly Gln Tyr Trp Cys His Phe Gln Asp
        115                 120                 125

Gly Asn Tyr Cys Gly Glu Thr Ser Leu Leu Lys Val Ala Glu Lys
    130                 135                 140

Leu Gln Thr Glu Leu Ala Ser Leu Lys Val Asn Gly Pro Ser Gln Pro
145                 150                 155                 160

Ile Leu Val Arg Val Gly Glu Asp Ile Gln Leu Thr Cys Tyr Leu Ser
                165                 170                 175

Pro Lys Ala Asn Ala Gln Ser Met Glu Val Arg Trp Asp Arg Ser His
            180                 185                 190

Arg Tyr Pro Ala Val His Val Tyr Met Asp Gly Asp His Val Ala Gly
        195                 200                 205
```

```
Glu Gln Met Ala Glu Tyr Arg Gly Arg Thr Val Leu Val Ser Asp Ala
    210                 215                 220
Ile Asp Glu Gly Arg Leu Thr Leu Gln Ile Leu Ser Ala Arg Pro Ser
225                 230                 235                 240
Asp Asp Gly Gln Tyr Arg Cys Leu Phe Glu Lys Asp Asp Val Tyr Gln
                245                 250                 255
Glu Ala Ser Leu Asp Leu Lys Val Val Gly Leu Gly Ser Ser Pro Leu
                260                 265                 270
Ile Thr Val Glu Gly Gln Glu Asp Gly Glu Met Gln Leu Ile Cys Ser
            275                 280                 285
Ser Asp Gly Trp Phe Pro Gln Pro His Val Gln Trp Arg Asp Met Glu
    290                 295                 300
Gly Lys Thr Ile Pro Ser Ser Gln Ala Leu Thr Gln Gly Ser His
305                 310                 315                 320
Gly Leu Phe His Val Gln Thr Leu Leu Arg Val Thr Asn Ile Ser Ala
                325                 330                 335
Val Asp Val Thr Cys Ser Ile Ser Ile Pro Phe Leu Gly Glu Glu Lys
                340                 345                 350
Ile Ala Thr Phe Ser Leu Ser
            355

<210> SEQ ID NO 15
<211> LENGTH: 1075
<212> TYPE: DNA
<213> ORGANISM: Homo sapiens

<400> SEQUENCE: 15
atggtggatt ttccaggcta caatctgtct ggtgcagtcg cctccttcct attcatcctg      60
ctgacaatga agcagtcaga ctttagagtc attggccctg ctcatcctat cctggccggg     120
gttggggaag atgccctgtt aacctgccag ctactcccca gaggaccac aatgcacgtg      180 gaggtgaggt ggtaccgctc agagcccagc acacctgtgt tgtgcacag ggatggagtg      240 gaggtgactg agatgcagat ggaggagtac agaggctggg tagagtggat agagaatggc     300
attgcaaagg gaaatgtggc actgaagata cacaacatcc agccctccga caatggacaa     360
tactggtgcc atttccagga tgggaactac tgtggagaaa caagcttgct gctcaaagta     420
gcagagaaac tccagactga gctggcttct ttaaaagtga atggaccttc ccagcccatc     480
ctcgtcagag tgggagaaga tatacagcta acctgttacc tgtcccccaa ggcgaatgca     540
cagagcatgg aggtgaggtg ggaccgatcc caccgttacc ctgctgtgca tgtgtatatg     600 gatgggacc atgtggctgg agagcagatg gcagagtaca gagggaggac tgtgctggtg      660
agtgacgcca ttgacgaggg cagactgacc ctgcagatac tcagtgccag accttcggac     720
gacgggcagt accgctgcct ttttgaaaaa gatgatgtct accaggaggc cagtttggat     780
ctgaaggtgg taggtctggg ttcttcccca ctgatcactg tggagggca agaagatgga      840 gaaatgcagc tgatatgctc ttcagatggg tggttcccac agccccacgt gcagtggagg     900
gacatggaag aaagacgat accatcctct cccaggccc tgactcaagg cagccatggg       960
ctgttccacg tgcagacatt gctaagggtc acaaacatct ccgctgtgga cgtcacttgt    1020
tccatcagca tcccttttt gggcgaggag aaaatcgcaa cttttctct ctcag           1075

<210> SEQ ID NO 16
<211> LENGTH: 358
<212> TYPE: PRT
<213> ORGANISM: Homo sapiens
```

```
<400> SEQUENCE: 16

Met Val Asp Phe Pro Gly Tyr Asn Leu Ser Gly Ala Val Ala Ser Phe
1               5                   10                  15

Leu Phe Ile Leu Leu Thr Met Lys Gln Ser Asp Phe Arg Val Ile Gly
            20                  25                  30

Pro Ala His Pro Ile Leu Ala Gly Val Gly Glu Asp Ala Leu Leu Thr
        35                  40                  45

Cys Gln Leu Leu Pro Lys Arg Thr Thr Met His Val Glu Val Arg Trp
50                  55                  60

Tyr Arg Ser Glu Pro Ser Thr Pro Val Phe Val His Arg Asp Gly Val
65                  70                  75                  80

Glu Val Thr Glu Met Gln Met Glu Glu Tyr Arg Gly Trp Val Glu Trp
                85                  90                  95

Ile Glu Asn Gly Ile Ala Lys Gly Asn Val Ala Leu Lys Ile His Asn
            100                 105                 110

Ile Gln Pro Ser Asp Asn Gly Gln Tyr Trp Cys His Phe Gln Asp Gly
        115                 120                 125

Asn Tyr Cys Gly Glu Thr Ser Leu Leu Leu Lys Val Ala Glu Lys Leu
130                 135                 140

Gln Thr Glu Leu Ala Ser Leu Lys Val Asn Gly Pro Ser Gln Pro Ile
145                 150                 155                 160

Leu Val Arg Val Gly Glu Asp Ile Gln Leu Thr Cys Tyr Leu Ser Pro
                165                 170                 175

Lys Ala Asn Ala Gln Ser Met Glu Val Arg Trp Asp Arg Ser His Arg
            180                 185                 190

Tyr Pro Ala Val His Val Tyr Met Asp Gly Asp His Val Ala Gly Glu
        195                 200                 205

Gln Met Ala Glu Tyr Arg Gly Arg Thr Val Leu Val Ser Asp Ala Ile
210                 215                 220

Asp Glu Gly Arg Leu Thr Leu Gln Ile Leu Ser Ala Arg Pro Ser Asp
225                 230                 235                 240

Asp Gly Gln Tyr Arg Cys Leu Phe Glu Lys Asp Asp Val Tyr Gln Glu
                245                 250                 255

Ala Ser Leu Asp Leu Lys Val Val Gly Leu Gly Ser Ser Pro Leu Ile
            260                 265                 270

Thr Val Glu Gly Gln Glu Asp Gly Glu Met Gln Leu Ile Cys Ser Ser
        275                 280                 285

Asp Gly Trp Phe Pro Gln Pro His Val Gln Trp Arg Asp Met Glu Gly
290                 295                 300

Lys Thr Ile Pro Ser Ser Ser Gln Ala Leu Thr Gln Gly Ser His Gly
305                 310                 315                 320

Leu Phe His Val Gln Thr Leu Leu Arg Val Thr Asn Ile Ser Ala Val
                325                 330                 335

Asp Val Thr Cys Ser Ile Ser Ile Pro Phe Leu Gly Glu Glu Lys Ile
            340                 345                 350

Ala Thr Phe Ser Leu Ser
            355

<210> SEQ ID NO 17
<211> LENGTH: 1427
<212> TYPE: DNA
<213> ORGANISM: Mus sp.
<220> FEATURE:
<221> NAME/KEY: CDS
<222> LOCATION: (1)..(1263)
```

<400> SEQUENCE: 17

```
atg gtg gat tgc cca cgg tat agt cta tct ggc gtg gct gcc tcc ttc     48
Met Val Asp Cys Pro Arg Tyr Ser Leu Ser Gly Val Ala Ala Ser Phe
1               5                   10                  15 ctc ttc gtc ctg ctg act ata aag cac cca gat gac ttc aga gtg gtc     96
Leu Phe Val Leu Leu Thr Ile Lys His Pro Asp Asp Phe Arg Val Val
            20                  25                  30 ggt cct aac ctc cca atc ctg gct aaa gtc ggg gaa gat gcc ctg cta    144
Gly Pro Asn Leu Pro Ile Leu Ala Lys Val Gly Glu Asp Ala Leu Leu
        35                  40                  45 acg tgt cag ctc ctc ccc aag agg acc acg gca cac atg gag gtg agg    192
Thr Cys Gln Leu Leu Pro Lys Arg Thr Thr Ala His Met Glu Val Arg
50                  55                  60 tgg tac cgc tcc gac cct gcc atg cca gtg att atg tac cgg gat gga    240
Trp Tyr Arg Ser Asp Pro Ala Met Pro Val Ile Met Tyr Arg Asp Gly
65                  70                  75                  80 gct gtg gtg act ggg cta ccg atg gag ggg tac gga ggc cgg gca gag    288
Ala Val Val Thr Gly Leu Pro Met Glu Gly Tyr Gly Gly Arg Ala Glu
                85                  90                  95 tgg atg gag gac agc act gaa gag ggc agt gtg gct ctg aag att cgc    336
Trp Met Glu Asp Ser Thr Glu Glu Gly Ser Val Ala Leu Lys Ile Arg
            100                 105                 110 cag gtc cag cca agt gac gat ggc cag tac tgg tgc cgc ttc cag gag    384
Gln Val Gln Pro Ser Asp Asp Gly Gln Tyr Trp Cys Arg Phe Gln Glu
        115                 120                 125 ggg gac tac tgg aga gag aca agc gtg cta ctc caa gtg gct gag agg    432
Gly Asp Tyr Trp Arg Glu Thr Ser Val Leu Leu Gln Val Ala Glu Arg
130                 135                 140 ctc cag acc gaa ctg gtt tcc gtt agc gta atc gga cat tcc cag ccc    480
Leu Gln Thr Glu Leu Val Ser Val Ser Val Ile Gly His Ser Gln Pro
145                 150                 155                 160 agc cct gtt caa gtc gga gag aac ata gaa tta act tgt cac ctc tca    528
Ser Pro Val Gln Val Gly Glu Asn Ile Glu Leu Thr Cys His Leu Ser
                165                 170                 175 cct caa acg gat gct cag aac tta gag gtg agg tgg ctc cga tcc cgc    576
Pro Gln Thr Asp Ala Gln Asn Leu Glu Val Arg Trp Leu Arg Ser Arg
            180                 185                 190 tat tac cct gca gtc cac gtg tat gca aat ggc acc cac gtg gct gga    624
Tyr Tyr Pro Ala Val His Val Tyr Ala Asn Gly Thr His Val Ala Gly
        195                 200                 205 gag cag atg gta gaa tac aaa ggg agg act tca ttg gtg act gat gcc    672
Glu Gln Met Val Glu Tyr Lys Gly Arg Thr Ser Leu Val Thr Asp Ala
210                 215                 220 atc cac gag gga aaa ctg acc ctg cag att cac aat gcc aga act tcg    720
Ile His Glu Gly Lys Leu Thr Leu Gln Ile His Asn Ala Arg Thr Ser
225                 230                 235                 240 gat gaa ggg cag tac cgg tgc ctt ttt gga aaa gat ggt gtc tac cag    768
Asp Glu Gly Gln Tyr Arg Cys Leu Phe Gly Lys Asp Gly Val Tyr Gln
                245                 250                 255 gag gcc cgt gtg gat gtg cag gtg acg gcg gtg ggt tcc acc cca cgg    816
Glu Ala Arg Val Asp Val Gln Val Thr Ala Val Gly Ser Thr Pro Arg
            260                 265                 270 atc acc agg gag gtc ttg aaa gat gga ggc atg cag ctg agg tgt acg    864
Ile Thr Arg Glu Val Leu Lys Asp Gly Gly Met Gln Leu Arg Cys Thr
        275                 280                 285 tct gat ggg tgg ttc cca cgg ccc cat gtg cag tgg agg gac aga gat    912
Ser Asp Gly Trp Phe Pro Arg Pro His Val Gln Trp Arg Asp Arg Asp
290                 295                 300
```

```
gga aag aca atg cca tcg ttt tcc gag gcc ttt cag caa ggg agc cag      960
Gly Lys Thr Met Pro Ser Phe Ser Glu Ala Phe Gln Gln Gly Ser Gln
305                 310                 315                 320 gag ctg ttc cag gtg gag aca ctt ctg ctg gtc aca aac ggc tcc atg     1008
Glu Leu Phe Gln Val Glu Thr Leu Leu Leu Val Thr Asn Gly Ser Met
                325                 330                 335 gtg aat gtg acc tgc tcc atc agc ctc cct ctg ggc cag gag aaa aca     1056
Val Asn Val Thr Cys Ser Ile Ser Leu Pro Leu Gly Gln Glu Lys Thr
            340                 345                 350 gcc cgt ttc cct ctc tca gac tcc aag ata gct ttg tta tgg atg acc     1104
Ala Arg Phe Pro Leu Ser Asp Ser Lys Ile Ala Leu Leu Trp Met Thr
        355                 360                 365 ctg cct gtt gtg gtg ctg cct ctc gcc atg gct atg gac ctg atc aag     1152
Leu Pro Val Val Val Leu Pro Leu Ala Met Ala Met Asp Leu Ile Lys
370                 375                 380 gtg aaa cgg cgg cga cgg acc aat gaa caa aca cac agc agc aat cag     1200
Val Lys Arg Arg Arg Arg Thr Asn Glu Gln Thr His Ser Ser Asn Gln
385                 390                 395                 400 gaa aat aac aag aat gac gaa aac cac agg cgg cga ctt cct tct gac     1248
Glu Asn Asn Lys Asn Asp Glu Asn His Arg Arg Arg Leu Pro Ser Asp
                405                 410                 415 gag agg ctc aga tga aaatgcaccc cgcaagccca acgcacccca tttcctgaac     1303
Glu Arg Leu Arg
            420 accccatccc tcctcccatc ttttcccctc aataagctgc actgacatag gagtggtttc   1363 acttgctact ctccaaaggt tcttcatgga ccctgtccgt acctgatgca accatcacgc   1423 acag                                                               1427

<210> SEQ ID NO 18
<211> LENGTH: 420
<212> TYPE: PRT
<213> ORGANISM: Mus sp.

<400> SEQUENCE: 18

Met Val Asp Cys Pro Arg Tyr Ser Leu Ser Gly Val Ala Ala Ser Phe
1               5                   10                  15

Leu Phe Val Leu Leu Thr Ile Lys His Pro Asp Asp Phe Arg Val Val
            20                  25                  30

Gly Pro Asn Leu Pro Ile Leu Ala Lys Val Gly Glu Asp Ala Leu Leu
        35                  40                  45

Thr Cys Gln Leu Leu Pro Lys Arg Thr Thr Ala His Met Glu Val Arg
    50                  55                  60

Trp Tyr Arg Ser Asp Pro Ala Met Pro Val Ile Met Tyr Arg Asp Gly
65                  70                  75                  80

Ala Val Val Thr Gly Leu Pro Met Glu Gly Tyr Gly Arg Ala Glu
            85                  90                  95

Trp Met Glu Asp Ser Thr Glu Glu Gly Ser Val Ala Leu Lys Ile Arg
            100                 105                 110

Gln Val Gln Pro Ser Asp Asp Gly Gln Tyr Trp Cys Arg Phe Gln Glu
        115                 120                 125

Gly Asp Tyr Trp Arg Glu Thr Ser Val Leu Gln Val Ala Glu Arg
    130                 135                 140

Leu Gln Thr Glu Leu Val Ser Val Ser Val Ile Gly His Ser Gln Pro
145                 150                 155                 160

Ser Pro Val Gln Val Gly Glu Asn Ile Glu Leu Thr Cys His Leu Ser
                165                 170                 175
```

```
Pro Gln Thr Asp Ala Gln Asn Leu Glu Val Arg Trp Leu Arg Ser Arg
            180                 185                 190

Tyr Tyr Pro Ala Val His Val Tyr Ala Asn Gly Thr His Val Ala Gly
        195                 200                 205

Glu Gln Met Val Glu Tyr Lys Gly Arg Thr Ser Leu Val Thr Asp Ala
    210                 215                 220

Ile His Glu Gly Lys Leu Thr Leu Gln Ile His Asn Ala Arg Thr Ser
225                 230                 235                 240

Asp Glu Gly Gln Tyr Arg Cys Leu Phe Gly Lys Asp Gly Val Tyr Gln
                245                 250                 255

Glu Ala Arg Val Asp Val Gln Val Thr Ala Val Gly Ser Thr Pro Arg
            260                 265                 270

Ile Thr Arg Glu Val Leu Lys Asp Gly Gly Met Gln Leu Arg Cys Thr
        275                 280                 285

Ser Asp Gly Trp Phe Pro Arg Pro His Val Gln Trp Arg Asp Arg Asp
    290                 295                 300

Gly Lys Thr Met Pro Ser Phe Ser Glu Ala Phe Gln Gln Gly Ser Gln
305                 310                 315                 320

Glu Leu Phe Gln Val Glu Thr Leu Leu Leu Val Thr Asn Gly Ser Met
                325                 330                 335

Val Asn Val Thr Cys Ser Ile Ser Leu Pro Leu Gly Gln Glu Lys Thr
            340                 345                 350

Ala Arg Phe Pro Leu Ser Asp Ser Lys Ile Ala Leu Leu Trp Met Thr
        355                 360                 365

Leu Pro Val Val Leu Pro Leu Ala Met Ala Met Asp Leu Ile Lys
    370                 375                 380

Val Lys Arg Arg Arg Thr Asn Glu Gln Thr His Ser Ser Asn Gln
385                 390                 395                 400

Glu Asn Asn Lys Asn Asp Glu Asn His Arg Arg Leu Pro Ser Asp
                405                 410                 415

Glu Arg Leu Arg
            420

<210> SEQ ID NO 19
<211> LENGTH: 2070
<212> TYPE: DNA
<213> ORGANISM: Homo sapiens and Mus sp.
<220> FEATURE:
<221> NAME/KEY: CDS
<222> LOCATION: (1)..(2070)

<400> SEQUENCE: 19 atg gtg gat tgc cca cgg tat agt cta tct ggc gtg gct gcc tcc ttc      48
Met Val Asp Cys Pro Arg Tyr Ser Leu Ser Gly Val Ala Ala Ser Phe
 1               5                  10                  15 ctc ttc gtc ctg ctg act ata aag cac cca gat gac ttc aga gtg gtc      96
Leu Phe Val Leu Leu Thr Ile Lys His Pro Asp Asp Phe Arg Val Val
                20                  25                  30 ggt cct aac ctc cca atc ctg gct aaa gtc ggg gaa gat gcc ctg cta     144
Gly Pro Asn Leu Pro Ile Leu Ala Lys Val Gly Glu Asp Ala Leu Leu
            35                  40                  45 acg tgt cag ctc ctc ccc aag agg acc acg gca cac atg gag gtg agg     192
Thr Cys Gln Leu Leu Pro Lys Arg Thr Thr Ala His Met Glu Val Arg
        50                  55                  60 tgg tac cgc tcc gac cct gcc atg cca gtg att atg tac cgg gat gga     240
Trp Tyr Arg Ser Asp Pro Ala Met Pro Val Ile Met Tyr Arg Asp Gly
65                  70                  75                  80
```

-continued

| | |
|---|---|
| gct gtg gtg act ggg cta ccg atg gag ggg tac gga ggc cgg gca gag<br>Ala Val Val Thr Gly Leu Pro Met Glu Gly Tyr Gly Gly Arg Ala Glu<br>                  85                        90                        95 | 288 |
| tgg atg gag gac agc act gaa gag ggc agt gtg gct ctg aag att cgc<br>Trp Met Glu Asp Ser Thr Glu Glu Gly Ser Val Ala Leu Lys Ile Arg<br>             100                      105                      110 | 336 |
| cag gtc cag cca agt gac gat ggc cag tac tgg tgc cgc ttc cag gag<br>Gln Val Gln Pro Ser Asp Asp Gly Gln Tyr Trp Cys Arg Phe Gln Glu<br>115                        120                      125 | 384 |
| ggg gac tac tgg aga gag aca agc gtg cta ctc caa gtg gct gct cta<br>Gly Asp Tyr Trp Arg Glu Thr Ser Val Leu Leu Gln Val Ala Ala Leu<br>    130                      135                      140 | 432 |
| gga tct tcc cca aat atc cat gtg gag gga ctt gga gaa gga gag gtc<br>Gly Ser Ser Pro Asn Ile His Val Glu Gly Leu Gly Glu Gly Glu Val<br>145                    150                      155                  160 | 480 |
| caa ctt gta tgc acg tcc cga ggc tgg ttc cct gag cct gag gtg cac<br>Gln Leu Val Cys Thr Ser Arg Gly Trp Phe Pro Glu Pro Glu Val His<br>                  165                      170                      175 | 528 |
| tgg gaa ggc atc tgg gga gaa aag ttg atg agt ttc tct gag aat cat<br>Trp Glu Gly Ile Trp Gly Glu Lys Leu Met Ser Phe Ser Glu Asn His<br>        180                      185                      190 | 576 |
| gtg cca ggt gaa gat ggg cta ttc tat gtg gaa gac aca ctg atg gtc<br>Val Pro Gly Glu Asp Gly Leu Phe Tyr Val Glu Asp Thr Leu Met Val<br>            195                      200                      205 | 624 |
| agg aat gac agt gta gag acc att tcc tgc ttc atc tac agc cat ggc<br>Arg Asn Asp Ser Val Glu Thr Ile Ser Cys Phe Ile Tyr Ser His Gly<br>    210                      215                      220 | 672 |
| ctc aga gag acc cag gag gcc acc atc gct ctg tca gag agg ctc cag<br>Leu Arg Glu Thr Gln Glu Ala Thr Ile Ala Leu Ser Glu Arg Leu Gln<br>225                    230                      235                  240 | 720 |
| acc gaa ctg gtt tcc gtt agc gta atc gga cat tcc cag ccc agc cct<br>Thr Glu Leu Val Ser Val Ser Val Ile Gly His Ser Gln Pro Ser Pro<br>                  245                      250                      255 | 768 |
| gtt caa gtc gga gag aac ata gaa tta act tgt cac ctc tca cct caa<br>Val Gln Val Gly Glu Asn Ile Glu Leu Thr Cys His Leu Ser Pro Gln<br>        260                      265                      270 | 816 |
| acg gat gct cag aac tta gag gtg agg tgg ctc cga tcc cgc tat tac<br>Thr Asp Ala Gln Asn Leu Glu Val Arg Trp Leu Arg Ser Arg Tyr Tyr<br>            275                      280                      285 | 864 |
| cct gca gtc cac gtg tat gca aat ggc acc cac gtg gct gga gag cag<br>Pro Ala Val His Val Tyr Ala Asn Gly Thr His Val Ala Gly Glu Gln<br>    290                      295                      300 | 912 |
| atg gta gaa tac aaa ggg agg act tca ttg gtg act gat gcc atc cac<br>Met Val Glu Tyr Lys Gly Arg Thr Ser Leu Val Thr Asp Ala Ile His<br>305                    310                      315                  320 | 960 |
| gag gga aaa ctg acc ctg cag att cac aat gcc aga act tcg gat gaa<br>Glu Gly Lys Leu Thr Leu Gln Ile His Asn Ala Arg Thr Ser Asp Glu<br>                  325                      330                      335 | 1008 |
| ggg cag tac cgg tgc ctt ttt gga aaa gat ggt gtc tac cag gag gcc<br>Gly Gln Tyr Arg Cys Leu Phe Gly Lys Asp Gly Val Tyr Gln Glu Ala<br>        340                      345                      350 | 1056 |
| cgt gtg gat gtg cag gtg acg gcg gtg ggt tcc acc cca cgg atc acc<br>Arg Val Asp Val Gln Val Thr Ala Val Gly Ser Thr Pro Arg Ile Thr<br>            355                      360                      365 | 1104 |
| agg gag gtc ttg aaa gat gga ggc atg cag ctg agg tgt acg tct gat<br>Arg Glu Val Leu Lys Asp Gly Gly Met Gln Leu Arg Cys Thr Ser Asp<br>    370                      375                      380 | 1152 |
| ggg tgg ttc cca cgg ccc cat gtg cag tgg agg gac aga gat gga aag<br>Gly Trp Phe Pro Arg Pro His Val Gln Trp Arg Asp Arg Asp Gly Lys<br>385                    390                      395                  400 | 1200 |

```
aca atg cca tcg ttt tcc gag gcc ttt cag caa ggg agc cag gag ctg    1248
Thr Met Pro Ser Phe Ser Glu Ala Phe Gln Gln Gly Ser Gln Glu Leu
            405                 410                 415 ttc cag gtg gag aca ctt ctg ctg gtc aca aac ggc tcc atg gtg aat    1296
Phe Gln Val Glu Thr Leu Leu Leu Val Thr Asn Gly Ser Met Val Asn
        420                 425                 430 gtg acc tgc tcc atc agc ctc cct ctg ggc cag gag aaa aca gcc cgt    1344
Val Thr Cys Ser Ile Ser Leu Pro Leu Gly Gln Glu Lys Thr Ala Arg
                435                 440                 445 ttc cct ctc tca gac tcc aag tac gta gag ccc aga tct tgt gac aaa    1392
Phe Pro Leu Ser Asp Ser Lys Tyr Val Glu Pro Arg Ser Cys Asp Lys
450                 455                 460 act cac aca tgc cca ccg tgc cca gca cct gaa gcc gag ggc gcg ccg    1440
Thr His Thr Cys Pro Pro Cys Pro Ala Pro Glu Ala Glu Gly Ala Pro
465                 470                 475                 480 tca gtc ttc ctc ttc ccc cca aaa ccc aag gac acc ctc atg atc tcc    1488
Ser Val Phe Leu Phe Pro Pro Lys Pro Lys Asp Thr Leu Met Ile Ser
            485                 490                 495 cgg acc cct gag gtc aca tgc gtg gtg gtg gac gtg agc cac gaa gac    1536
Arg Thr Pro Glu Val Thr Cys Val Val Val Asp Val Ser His Glu Asp
        500                 505                 510 cct gag gtc aag ttc aac tgg tac gtg gac ggc gtg gag gtg cat aat    1584
Pro Glu Val Lys Phe Asn Trp Tyr Val Asp Gly Val Glu Val His Asn
    515                 520                 525 gcc aag aca aag ccg cgg gag gag cag tac aac agc acg tac cgt gtg    1632
Ala Lys Thr Lys Pro Arg Glu Glu Gln Tyr Asn Ser Thr Tyr Arg Val
530                 535                 540 gtc agc gtc ctc acc gtc ctg cac cag gac tgg ctg aat ggc aag gag    1680
Val Ser Val Leu Thr Val Leu His Gln Asp Trp Leu Asn Gly Lys Glu
545                 550                 555                 560 tac aag tgc aag gtc tcc aac aaa gcc ctc cca gcc ccc atc gag aaa    1728
Tyr Lys Cys Lys Val Ser Asn Lys Ala Leu Pro Ala Pro Ile Glu Lys
                565                 570                 575 acc atc tcc aaa gcc aaa ggg cag ccc cga gaa cca cag gtg tac acc    1776
Thr Ile Ser Lys Ala Lys Gly Gln Pro Arg Glu Pro Gln Val Tyr Thr
            580                 585                 590 ctg ccc cca tcc cgg gag gag atg acc aag aac cag gtc agc ctg acc    1824
Leu Pro Pro Ser Arg Glu Glu Met Thr Lys Asn Gln Val Ser Leu Thr
        595                 600                 605 tgc ctg gtc aaa ggc ttc tat ccc agc gac atc gcc gtg gag tgg gag    1872
Cys Leu Val Lys Gly Phe Tyr Pro Ser Asp Ile Ala Val Glu Trp Glu
610                 615                 620 agc aat ggg cag ccg gag aac aac tac aag acc acg cct ccc gtg ctg    1920
Ser Asn Gly Gln Pro Glu Asn Asn Tyr Lys Thr Thr Pro Pro Val Leu
625                 630                 635                 640 gac tcc gac ggc tcc ttc ttc ctc tat agc aag ctc acc gtg gac aag    1968
Asp Ser Asp Gly Ser Phe Phe Leu Tyr Ser Lys Leu Thr Val Asp Lys
                645                 650                 655 agc agg tgg cag cag ggg aac gtc ttc tca tgc tcc gtg atg cat gag    2016
Ser Arg Trp Gln Gln Gly Asn Val Phe Ser Cys Ser Val Met His Glu
            660                 665                 670 gct ctg cac aac cac tac acg cag aag agc ctc tcc ctg tct ccg ggt    2064
Ala Leu His Asn His Tyr Thr Gln Lys Ser Leu Ser Leu Ser Pro Gly
        675                 680                 685 aaa tga                                                            2070
Lys
```

<210> SEQ ID NO 20
<211> LENGTH: 689
<212> TYPE: PRT
<213> ORGANISM: Homo sapiens and Mus sp.

<400> SEQUENCE: 20

```
Met Val Asp Cys Pro Arg Tyr Ser Leu Ser Gly Val Ala Ala Ser Phe
1               5                   10                  15

Leu Phe Val Leu Leu Thr Ile Lys His Pro Asp Asp Phe Arg Val Val
            20                  25                  30

Gly Pro Asn Leu Pro Ile Leu Ala Lys Val Gly Glu Asp Ala Leu Leu
        35                  40                  45

Thr Cys Gln Leu Leu Pro Lys Arg Thr Thr Ala His Met Glu Val Arg
    50                  55                  60

Trp Tyr Arg Ser Asp Pro Ala Met Pro Val Met Tyr Arg Asp Gly
65                  70                  75                  80

Ala Val Val Thr Gly Leu Pro Met Glu Gly Tyr Gly Arg Ala Glu
            85                  90                  95

Trp Met Glu Asp Ser Thr Glu Glu Gly Ser Val Ala Leu Lys Ile Arg
            100                 105                 110

Gln Val Gln Pro Ser Asp Asp Gly Gln Tyr Trp Cys Arg Phe Gln Glu
        115                 120                 125

Gly Asp Tyr Trp Arg Glu Thr Ser Val Leu Leu Gln Val Ala Ala Leu
    130                 135                 140

Gly Ser Ser Pro Asn Ile His Val Glu Gly Leu Gly Glu Gly Glu Val
145                 150                 155                 160

Gln Leu Val Cys Thr Ser Arg Gly Trp Phe Pro Glu Pro Glu Val His
                165                 170                 175

Trp Glu Gly Ile Trp Gly Glu Lys Leu Met Ser Phe Ser Glu Asn His
            180                 185                 190

Val Pro Gly Glu Asp Gly Leu Phe Tyr Val Glu Asp Thr Leu Met Val
        195                 200                 205

Arg Asn Asp Ser Val Glu Thr Ile Ser Cys Phe Ile Tyr Ser His Gly
    210                 215                 220

Leu Arg Glu Thr Gln Glu Ala Thr Ile Ala Leu Ser Glu Arg Leu Gln
225                 230                 235                 240

Thr Glu Leu Val Ser Val Ser Val Ile Gly His Ser Gln Pro Ser Pro
                245                 250                 255

Val Gln Val Gly Glu Asn Ile Glu Leu Thr Cys His Leu Ser Pro Gln
            260                 265                 270

Thr Asp Ala Gln Asn Leu Glu Val Arg Trp Leu Arg Ser Arg Tyr Tyr
        275                 280                 285

Pro Ala Val His Val Tyr Ala Asn Gly Thr His Val Ala Gly Glu Gln
    290                 295                 300

Met Val Glu Tyr Lys Gly Arg Thr Ser Leu Val Thr Asp Ala Ile His
305                 310                 315                 320

Glu Gly Lys Leu Thr Leu Gln Ile His Asn Ala Arg Thr Ser Asp Glu
                325                 330                 335

Gly Gln Tyr Arg Cys Leu Phe Lys Asp Gly Val Tyr Gln Glu Ala
            340                 345                 350

Arg Val Asp Val Gln Val Thr Ala Val Gly Ser Thr Pro Arg Ile Thr
        355                 360                 365

Arg Glu Val Leu Lys Asp Gly Met Gln Leu Arg Cys Thr Ser Asp
    370                 375                 380
```

```
                                        -continued
Gly Trp Phe Pro Arg Pro His Val Gln Trp Arg Asp Arg Asp Gly Lys
385                 390                 395                 400

Thr Met Pro Ser Phe Ser Glu Ala Phe Gln Gln Gly Ser Gln Glu Leu
                405                 410                 415

Phe Gln Val Glu Thr Leu Leu Leu Val Thr Asn Gly Ser Met Val Asn
            420                 425                 430

Val Thr Cys Ser Ile Ser Leu Pro Leu Gly Gln Glu Lys Thr Ala Arg
        435                 440                 445

Phe Pro Leu Ser Asp Ser Lys Tyr Val Glu Pro Arg Ser Cys Asp Lys
    450                 455                 460

Thr His Thr Cys Pro Pro Cys Pro Ala Pro Glu Ala Glu Gly Ala Pro
465                 470                 475                 480

Ser Val Phe Leu Phe Pro Pro Lys Pro Lys Asp Thr Leu Met Ile Ser
                485                 490                 495

Arg Thr Pro Glu Val Thr Cys Val Val Val Asp Val Ser His Glu Asp
            500                 505                 510

Pro Glu Val Lys Phe Asn Trp Tyr Val Asp Gly Val Glu Val His Asn
        515                 520                 525

Ala Lys Thr Lys Pro Arg Glu Glu Gln Tyr Asn Ser Thr Tyr Arg Val
    530                 535                 540

Val Ser Val Leu Thr Val Leu His Gln Asp Trp Leu Asn Gly Lys Glu
545                 550                 555                 560

Tyr Lys Cys Lys Val Ser Asn Lys Ala Leu Pro Ala Pro Ile Glu Lys
                565                 570                 575

Thr Ile Ser Lys Ala Lys Gly Gln Pro Arg Glu Pro Gln Val Tyr Thr
            580                 585                 590

Leu Pro Pro Ser Arg Glu Glu Met Thr Lys Asn Gln Val Ser Leu Thr
        595                 600                 605

Cys Leu Val Lys Gly Phe Tyr Pro Ser Asp Ile Ala Val Glu Trp Glu
    610                 615                 620

Ser Asn Gly Gln Pro Glu Asn Asn Tyr Lys Thr Thr Pro Pro Val Leu
625                 630                 635                 640

Asp Ser Asp Gly Ser Phe Phe Leu Tyr Ser Lys Leu Thr Val Asp Lys
                645                 650                 655

Ser Arg Trp Gln Gln Gly Asn Val Phe Ser Cys Ser Val Met His Glu
            660                 665                 670

Ala Leu His Asn His Tyr Thr Gln Lys Ser Leu Ser Leu Ser Pro Gly
        675                 680                 685

Lys
```

BTL-II PROTEINS

This application claims benefit of U.S. Provisional Application No. 60/436,185, filed Dec. 23, 2002 and U.S. Provisional Application No. 60/525,298, filed Nov. 26, 2003.

FIELD OF THE INVENTION

The invention relates to butyrophilin-like proteins, specifically butyrophilin-like proteins of the B7 subfamily, which are known to modulate the function of immune effector cells such as, for example, B cells and/or T cells. Nucleic acids encoding such proteins, processes for producing such proteins, antibodies that bind to such proteins, pharmaceutical compositions containing such proteins or antibodies, methods of using such nucleic acids, proteins, and antibodies against such proteins are also included.

BACKGROUND

Modulation of an immune or inflammatory response can be a valuable tool in controlling various kinds of diseases including autoimmune diseases, diseases characterized by abnormal inflammation and/or immune response, and infections. In treating diseases characterized by abnormal inflammation and/or immune responses, such as inflammatory bowel diseases and autoimmune or inflammatory diseases, down-modulation of an immune response is desirable. In other situations, for example when vaccinating a patient to impart immunity to an infectious disease, stimulation of an immune response is desirable. In the vaccine setting, adjuvants that can heighten an immune response to a coadministered antigen can be valuable in providing long term protection against disease. Particularly lacking in the art are adjuvants capable of stimulating a mucosal immune response. A mucosal immune response, as opposed to a systemic immune response, is valuable because it can attack an infection at a very common point of entry, that is, at a mucosal surface. The present invention addresses these needs in the art by providing therapeutic agents to diagnose and treat diseases characterized by inappropriate and/or abnormal inflammation and/or immune responses and therapeutic agents that can act as adjuvants to stimulate an immune response, particularly a mucosal immune response.

SUMMARY

The invention encompasses isolated BTL-II proteins, nucleic acids, antibodies, BTL-II inhibitors and agonists, and methods for using these compositions.

An isolated BTL-II protein comprising an amino acid sequence consisting of amino acids x–y of SEQ ID NO:4, wherein x is any amino acid from position 1 to 35 of SEQ ID NO:4 and y is any amino acid from position 452–462 of SEQ ID NO:4 is provided. Such a BTL-II protein can comprise amino acids 30 to 453, 1 to 453, 29 to 457, 1 to 457, 1 to 482, and/or 29 to 482 of SEQ ID NO:4. The invention further provides an isolated BTL-II protein comprising a polypeptide consisting of an amino acid sequence at least 80%, optionally at least 85%, 90%, 92%, 94%, 96%, or 98%, identical to amino acids 127 to 157 of SEQ ID NO:10, SEQ ID NO:14, or SEQ ID NO:18 or amino acids 126 to 156 of SEQ ID NO:16, wherein the identity region of the amino acid sequence aligned with amino acids 127 to 157 of SEQ ID NO:10, SEQ ID NO:14, or SEQ ID NO:18 or amino acids 126 to 156 of SEQ ID NO:16 is at least 20, optionally at least 25, or 30, amino acids long and the polypeptide can bind to a cell surface receptor expressed on B cells or T cells and/or can inhibit the proliferation of T cells. Such an amino acid sequence can be at least 150 amino acids long and can be at least 80%, optionally at least 85%, 90%, 92%, 94%, 96%, 98%, 99%, or 99.5%, identical to amino acids 30 to 358 of SEQ ID NO:10, SEQ ID NO:14, SEQ ID NO:16, or SEQ ID NO:18, wherein the identity region of the amino acid sequence aligned with amino acids 30 to 358 of SEQ ID NO:10, SEQ ID NO:14, SEQ ID NO:16, or SEQ ID NO:18 is at least 150, optionally at least 200, 250, or 300, amino acids. Further, the amino acid sequence can be at least 90%, optionally at least 92%, 94%, 96%, 98%, 99%, or 99.5%, identical to amino acids 30 to 358 of SEQ ID NO:10, SEQ ID NO:14, SEQ ID NO:16, or SEQ ID NO:18 and/or can comprise amino acids 30 to 358 of SEQ ID NO:10, SEQ ID NO:14, SEQ ID NO:16, or SEQ ID NO:18.

In another embodiment the invention encompasses an isolated BTL-II protein comprising a first polypeptide consisting of a first amino acid sequence at least 80%, optionally at least 85%, 90%, 92%, 94%, 96%, 98%, 99%, or 99.5%, identical to amino acids 30 to 358 of SEQ ID NO:10, SEQ ID NO:14, SEQ ID NO:16, or SEQ ID NO:18, wherein the identity region of the first amino acid sequence aligned with amino acids 30 to 358 of SEQ ID NO:10, SEQ ID NO:14, SEQ ID NO:16, or SEQ ID NO:18 is at least 150 amino acids, wherein the first polypeptide comprises a second polypeptide consisting of a second amino acid sequence at least 80%, optionally at least 85%, 90%, 92%, 94%, 96%, 98%, 99%, or 99.5%, identical to amino acids 127 to 157 of SEQ ID NO:10, SEQ ID NO:14, or SEQ ID NO:18, or amino acids 126 to 156 of SEQ ID NO:16, wherein the identity region of the second amino acid sequence aligned with amino acids 127 to 157 of SEQ ID NO:10, SEQ ID NO:14, or SEQ ID NO:18 or amino acids 126 to 156 of SEQ ID NO:16 is at least 20 amino acids long, and wherein the first polypeptide can inhibit the proliferation of T cells. The first amino acid sequence can be identical to amino acids 127 to 157 of SEQ ID NO:10, SEQ ID NO:14, or SEQ ID NO:18, or amino acids 126 to 156 of SEQ ID NO:16, Alternatively, the invention provides an isolated BTL-II protein comprising a polypeptide consisting of an amino acid sequence at least 80%, optionally at least 85%, 90%, 92%, 94%, 96%, 98%, 99%, or 99.5%, identical to amino acids 30 to 457 of SEQ ID NO:4, wherein the polypeptide comprises no more or less than 2 Ig-like domains, and wherein the polypeptide can inhibit the proliferation of T cells. The amino acid sequence can be at least 80%, 85%, 90%, 92%, 94%, 96%, 98%, 99%, 99.5%, or 100% identical to amino acids 30 to 247 of SEQ ID NO:8 or to amino acids 30 to 243 of SEQ ID NO:12. The amino acid sequence can be at least 90%, optionally at least 92%, 94%, 96%, 98%, 99%, 99.5%, or 100%, identical to amino acids 30 to 457 of SEQ ID NO:4.

Alternatively, a BTL-II protein of the invention can comprise a first polypeptide consisting of a first amino acid sequence at least 80%, optionally at least 85%, 90%, 92%, 94%, 96%, 98%, 99%, or 99.5%, identical to amino acids 247 to 452 SEQ ID NO:4 or to amino acids 248 to 447 of SEQ ID NO:6, wherein the first amino acid sequence does not comprise an amino acid sequence at least 80%, optionally at least 85%, 90%, 92%, 94%, 96%, 98%, 99%, or 99.5%, identical to amino acids 32 to 232 of SEQ ID NO:4 or to amino acid 27 to 232 of SEQ ID NO:6 with an identity region of the first amino acid sequence aligned with SEQ ID NO:4 of at least 25, optionally, at least 50, 75, 100, or 150, amino acids, and wherein the protein does not comprise a second polypeptide consisting of a second amino acid sequence at least 80%, optionally at least 85%, 90%, 92%, 94%, 96%, 98%, 99%, or 99.5%, identical to amino acids 32 to 232 of SEQ ID NO:4 or to amino acid 27 to 232 of SEQ ID NO:6 with an identity region of the second amino acid sequence aligned with SEQ ID NO:4 of at least 25, optionally, at least 50, 75, 100, or 150, amino acids, and wherein the first polypeptide can inhibit the proliferation of T cells.

In another embodiment, an isolated BTL-II protein of the invention can comprise a first polypeptide consisting of a first amino acid sequence at least 80%, optionally at least 85%, 90%, 92%, 94%, 96%, 98%, 99%, or 99.5%, identical to amino acids 32 to 242 of SEQ ID NO:8 or SEQ ID NO:12, wherein the identity region of the first amino acid sequence aligned with SEQ ID NO:8 or SEQ ID NO:12 is at least about 50, optionally at least about 75, 100, 150, or 200 amino acids long, wherein the first polypeptide comprises a second polypeptide consisting of an second amino acid sequence at least 80%, optionally at least 85%, 90%, 92%, 94%, 96%, 98%, 99%, or 99.5%, identical to amino acids 10 to 40 of SEQ ID NO:8 or SEQ ID NO:12, wherein the identity region of the second amino acid sequence aligned with SEQ ID NO:8 or SEQ ID NO:12 is at least about 20, optionally at least about 25 or 30, amino acids long, and wherein the first polypeptide can inhibit the proliferation of T cells.

In still another embodiment, the invention encompasses an isolated BTL-II protein comprising a polypeptide consisting of an amino acid sequence at least 80%, optionally at least 85%, 90%, 92%, 94%, 96%, 98%, 99%, or 99.5%, identical to amino acids 30 to 358 of SEQ ID NO:10, SEQ ID NO:14, SEQ ID NO:16, or SEQ ID NO:18, wherein the identity region of the amino acid sequence aligned with amino acids 30 to 358 of SEQ ID NO:10, SEQ ID NO:14, SEQ ID NO:16, or SEQ ID NO:18 is at least 250, optionally at least 275 or 300, amino acids, and wherein the polypeptide can inhibit the proliferation of T cells.

BTL-II proteins of the invention can comprise a polypeptide that can inhibit the proliferation of T cells that may be at most about 480 amino acids, about 380 amino acids, about 270 amino acids, or about 160 amino acids in length.

The invention further encompasses an isolated BTL-II protein comprising a first polypeptide consisting of a first amino acid sequence at least 80%, optionally at least 85%, 90%, 92%, 94%, 96%, 98%, 99%, or 99.5%, identical to amino acids 32 to 358 of SEQ ID NO:10, wherein the identity region of the first amino acid sequence aligned to SEQ ID NO:10 is at least about 175, optionally about 200, 250, 275 or 300, amino acids long, wherein the first amino acid sequence is not more than about 380, optionally not more than about 390, 270, or 170, amino acids in length, wherein the first polypeptide can inhibit the proliferation of T cells, wherein the first amino acid sequence is not at least 80% identical to amino acids 148 to 232 of SEQ ID NO:4 with an identity region of the first amino acid sequence aligned to amino acids 148 to 232 of SEQ ID NO:4 of at least about 20, 30, 40, 50, 60, or 75 amino acids, and wherein the BTL-II protein does not comprise a second amino acid sequence that is at least 80% identical to amino acids 148 to 232 of SEQ ID NO:4 with an identity region of the second amino acid sequence aligned to amino acids 148 to 232 of SEQ ID NO:4 of at least about 20, 30, 40, 50, 60, or 75 amino acids. Such a BTL-II protein may comprise amino acids 32 to 242 of SEQ ID NO:8 or SEQ ID NO:12.

In another embodiment, the invention comprises a BTL-II recombinant fusion protein comprising the BTL-II protein and a heterologous polypeptide, which can be an Fc region of an antibody or a leucine zipper. The invention also encompasses an immunogenic fragment of amino acids 29 to 457 SEQ ID NO:4 that is capable of eliciting antibodies that bind specifically to the fragment, that is at least 10 amino acids long, and that spans position 360 of SEQ ID NO:4. Immunogenic fragments of SEQ ID NO:10, SEQ ID NO:14, or SEQ ID NO:16, and SEQ ID NO:18 at least 10 amino acids long are provided, wherein the immunogenic fragment spans position 141 to 143 of SEQ ID NO:10, SEQ ID NO:14, SEQ ID NO:18, or SEQ ID NO:16 and can elicit antibodies that bind specifically to the fragment. Alternatively, the immunogenic fragments can span position 142 of SEQ ID NO:10, SEQ ID NO:14, or SEQ ID NO:18 or position 141 of SEQ ID NO:16.

In alternate embodiments, murine BTL-II proteins are provided. Specifically, the invention provides an isolated BTL-II protein comprising an amino acid sequence consisting of amino acids x–y of SEQ ID NO:6, wherein x is any amino acid from position 1 to 35 of SEQ ID NO:6 and y is any amino acid from position 450–460 of SEQ ID NO:6. Such a BTL-II protein can comprise amino acids 32–450, 29 to 456, and/or 29 to 514 of SEQ ID NO:6.

Other embodiments include isolated antibodies that bind specifically to a BTL-II protein consisting of amino acids 1–457 of SEQ ID NO:4, 1–456 of SEQ ID NO:6., 1–247 of SEQ ID NO:8, 1–363 of SEQ ID NO:10, 1–243 of SEQ ID NO:12, 1–359 of SEQ ID NO:14, 1–358 of SEQ ID NO:16, or 1–362 of SEQ ID NO:18. Such antibodies can be monoclonal antibodies, humanized antibodies, or human antibodies and may inhibit the binding of BTL-II to its receptor. The invention encompasses nucleic acids that encode such antibodies and cells that can produce such antibodies, which may be hybridoma cells or cells that have been genetically engineered to produce such an antibody. The invention further encompasses methods of producing antibodies by culturing such cells, which may secrete the antibody.

Other embodiments include BTL-II nucleic acids. The invention encompasses an isolated BTL-II nucleic acid comprising a polynucleotide consisting of nucleotides x to y of SEQ ID NO:3, wherein x is from nucleotide 1 to 105 and y is from nucleotide 1345 to 1375, or comprising the complement of the polynucleotide. Such a nucleic acid can comprise nucleotides 105 to 1345 or 1 to 1371 of SEQ ID NO:3. Further, nucleic acids encoding immunogenic fragments are provided, as are BTL-II nucleic acids encoding any of the BTL-II proteins described above.

The invention further provides a vector comprising any of the BTL-II nucleic acids described above or nucleic acids encoding anti-BTL-II antibodies and a host cell containing such a vector. Alternatively, the invention provides a host cell genetically engineered to express a BTL-II protein, an immunogenic fragment of BTL-II, or an antibody against BTL-II. Such host cells can be mammalian cells, including CHO cells. A method for producing a BTL-II protein, immunogenic fragment, or an anti-BTL-II antibody comprising culturing such a host cells under conditions allowing expression of the BTL-II protein, immunogenic fragment, or antibody is also encompassed by the invention. This method may further comprise isolating the BTL-II protein, immunogenic fragment, or antibody from the host cells or the medium. BTL-II proteins, immunogenic fragments, or antibodies produced by such methods are also contemplated. The invention further encompasses mammalian cells that produce antibodies against BTL-II, including hybridoma or myeloma cells and methods for making antibodies by culturing such cells.

Various therapeutic methods employing the compositions encompassed by the invention are also contemplated. The invention provides a method for reducing inflammation in the gut in a patient suffering from an inflammatory bowel disease, optionally either Crohn's disease or ulcerative colitis, comprising administering a therapeutically effective amount of a BTL-II protein, optionally a soluble BTL-II protein. A method for inducing an immune response, including a system and/or a mucosal immune response, against an antigen comprising administering a therapeutically effective amount of a BTL-II antagonist and the antigen is also provided. The BTL-II antagonist can be an antibody or a small molecule, and the antigen can be administered directly to a mucosal surface or can be administered systemically. Further provided is a method for diagnosing an inflammatory bowel disease or predicting the onset of an inflammatory bowel disease comprising assaying a tissue sample from the bowel of a patient to determine whether BTL-II mRNA or protein is overexpressed. The tissue can be assayed for BTL-II protein expression using an anti-BTL-II antibody. The invention further provides a method for dampening an immune response to an antigen, especially an auto-antigen in a patient suffering from an autoimmune or inflammatory disease, comprising co-administering the antigen and a soluble BTL-II protein. The antigen can be administered via a mucosal surface.

In further embodiments, the invention encompasses methods for inhibiting T cell proliferation and cytokine production. In one embodiment, the invention comprises a method for inhibiting T cell proliferation comprising contacting the T cells with a BTL-II polypeptide. The T cells can be human T cells and can be contacted with the BTL-II polypeptide in vivo. As an alternative to a BTL-II polypeptide, an agonistic antibody that binds to a BTL-II receptor expressed on T cells can be used, provided that it can inhibit the proliferation of T cells. In another embodiment, the invention includes a method for suppressing cytokine production by a T cell comprising contacting the T cell with a BTL-II polypeptide. The T cells can be human T cells and can be contacted with the BTL-II polypeptide in vivo. The cytokine can be, for example, interferon gamma (IFNγ), interleukin 2 (IL2), or interleukin 5 (IL5).

BRIEF DESCRIPTION OF THE FIGURES

FIG. 3b is a representative sequence of a member of the first category of splice variants (bottom line, SEQ ID NO:7) aligned to a portion of SEQ ID NO:3 (top line). There are no mismatches other than the gap created by the missing exons 2 and 3.

FIG. 4b shows a representative sequence of a member of the second category of splice variants (bottom line, SEQ ID NO:9) aligned to a portion of SEQ ID NO:3 (top line). There are no mismatches other than the gap created by the missing exon 3.

FIG. 5b shows a representative sequence of a member of the third category of splice variants (bottom line, SEQ ID NO:11) aligned to a portion of SEQ ID NO:3 (top line). Mismatched bases are indicated in boldface.

FIG. 6a shows the structure of a fourth category of splice variants of the human BTL-II mRNA. The large X over exon 3 indicates that this exon is missing in this category of splice variants. Sequence polymorphisms are indicated as in FIG. 5a, and variations 2 to 6 are as in FIG. 5a.

FIG. 6b shows a representative sequence of a member of the fourth category of splice variants (bottom line, SEQ ID NO:7) aligned to a portion of SEQ ID NO:3 (top line). Mismatched bases are indicated in boldface.

FIG. 7b shows a representative sequence of a member of the fifth category of splice variants (bottom line, SEQ ID NO:15) aligned to a portion of SEQ ID NO:3 (top line). Mismatched bases are indicated in boldface.

FIG. 9b shows a representative sequence of a member of the first category of murine splice variants (bottom line, SEQ ID NO:17) aligned to SEQ ID NO:5 (top line). There are no mismatches other than the gap created by the missing exon 3.

FIG. 16a shows proliferation of purified human T cells in response to various combinations of proteins indicated as in FIG. 12a.

FIG. 16b shows the relative interferon gamma (IFNγ) production in response to various combinations of proteins indicated as in FIG. 12a.

FIG. 16c shows the relative interleukin 2 (IL2) production in response to various combinations of proteins indicated as in FIG. 12a.

FIG. 16d shows the relative interleukin 5 (IL5) production in response to various combinations of proteins indicated as in FIG. 12a.

FIG. 17 is a bar graph showing the total number of dead cells in cultures of purified T cells cultured with various combinations of proteins, as indicated in FIG. 12a.

BRIEF DESCRIPTION OF THE SEQUENCE LISTINGS

SEQ ID NO:1 is the nucleotide sequence of the human BTL-II cDNA from the National Center for Biotechnology Information (NCBI) entry with the accession number NM_019602.

SEQ ID NO:2 is the amino acid sequence of the of the human BTL-II protein predicted from the cDNA sequence of the NCBI entry with the accession number NM_019602.

SEQ ID NO:3 is the nucleotide sequence of a full length human BTL-II cDNA of the invention.

SEQ ID NO:4 is the amino acid sequence of the full length human BTL-II protein encoded by SEQ ID NO:3.

SEQ ID NO:5 is the nucleotide sequence of the full length murine BTL-II cDNA of the invention.

SEQ ID NO:6 is the amino acid sequence of the full length murine BTL-II protein encoded by SEQ ID NO:5.

Figure 3A:
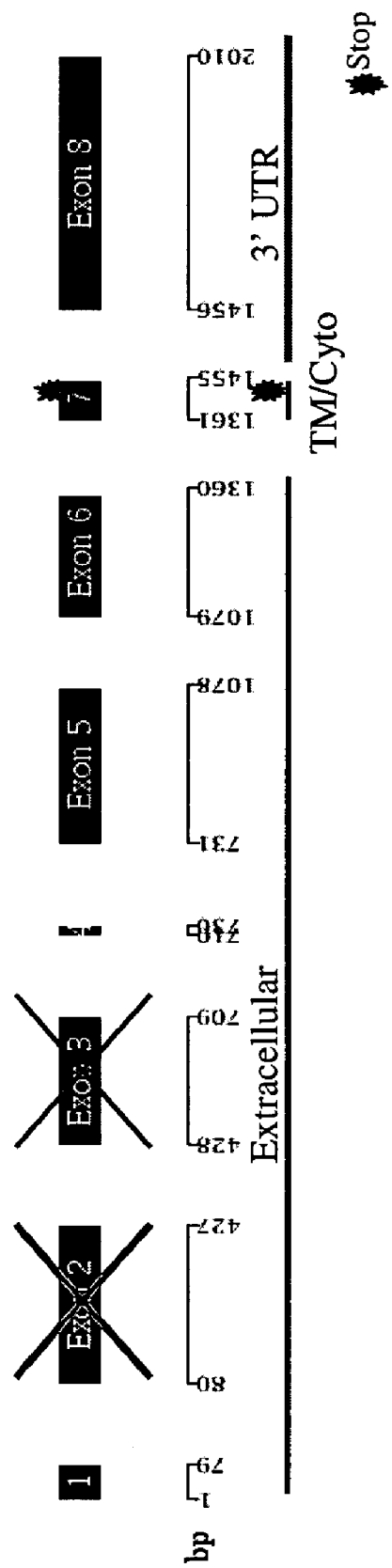
FIG. 3a is a diagram of the structure of a first category of splice variants of the human BTL-II mRNA. Symbols are the same as described for FIG. 2. The large Xs over exons 2 and 3 indicate that these exons are missing in this category of splice variants.

SEQ ID NO:7 is the nucleotide sequence of the cDNA from a representative member of the first category of human BTL-II splice variants (FIG. 3a).

SEQ ID NO:8 is the amino acid sequence encoded by SEQ ID NO:7.

Figure 4A:
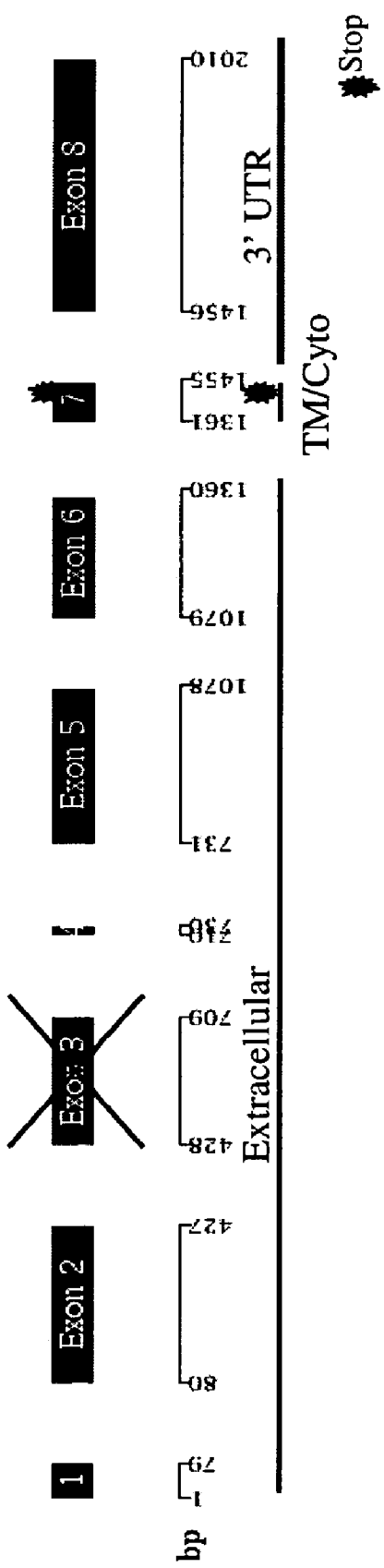
FIG. 4a shows the structure of a second category of splice variants of the human BTL-II RNA. Symbols are the same as described for FIG. 2. The large X over exon 3 indicates that this exon is missing in this category of splice variants.

SEQ ID NO:9 is the nucleotide sequence of the cDNA from a representative member of the second category of human BTL-II splice variants (FIG. 4a).

SEQ ID NO:10 is the amino acid sequence encoded by SEQ ID NO:9.

Figure 5A:
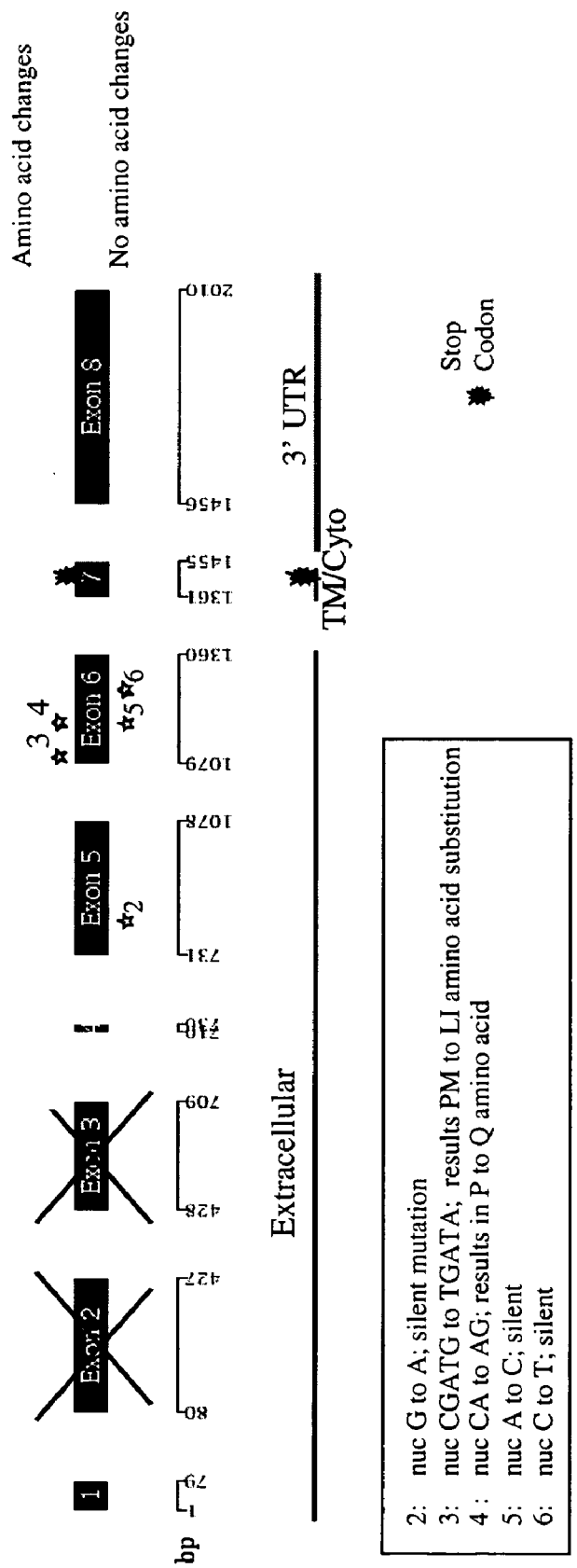
FIG. 5a shows the structure of a third category of splice variants of the human BTL-II mRNA. Symbols are the same as described for FIG. 3. The large Xs over exons 2 and 3 indicate that these exons are missing in this category of splice variants. The stars accompanied by numbers adjacent to the boxes indicate the positions of sequence polymorphisms present in this category of splice variants. The variations are present at the following positions within SEQ ID NO:3: variation 2 is at position 1050; variation 3 is at positions 1136 and 1140; variation 4 is at positions 1178 and 1179; and variation 5 is at position 1212; and variation 6 is at position 1242.

SEQ ID NO:11 is a partial nucleotide sequence of the cDNA from a representative member of the third category of human BTL-II splice variants (FIG. 5a).

SEQ ID NO:12 is the amino acid sequence encoded by SEQ ID NO:11.

Figure 6A:
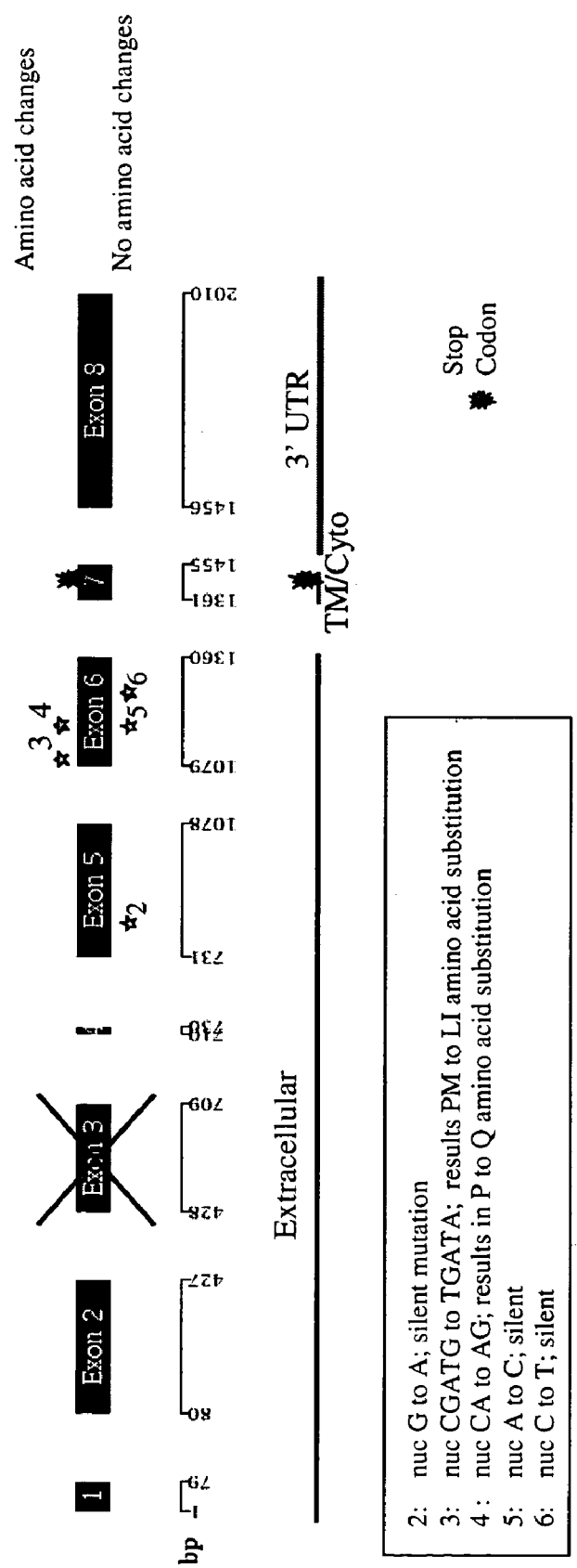

SEQ ID NO:13 is a partial nucleotide sequence of the cDNA from a representative member of the fourth category of human BTL-II splice variants (FIG. 6a).

SEQ ID NO:14 is the amino acid sequence encoded by SEQ ID NO:13.

Figure 7A:
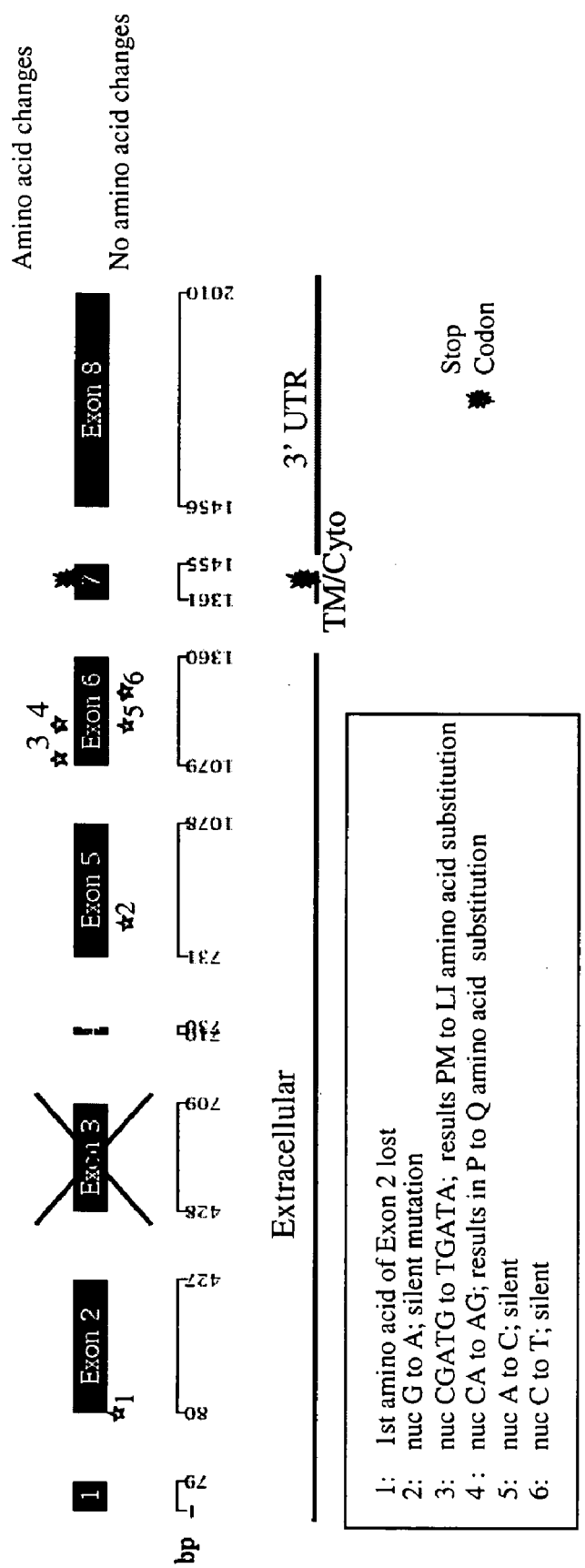
FIG. 7a shows the structure on a fifth category of splice variants of the human BTL-II mRNA. The large X over exon 3 indicates that this exon is missing in this category of splice variants. Sequence polymorphisms are indicated as in FIG. 5a, and variations 2 to 6 are as in FIG. 5a. Variation 1 is a deletion of nucleotides 78 to 80 of SEQ ID NO:3.

SEQ ID NO:15 is a partial nucleotide sequence of the cDNA from a representative member of a fifth category of human BTL-II splice variants (FIG. 7a).

SEQ ID NO:16 is the amino acid sequence encoded by SEQ ID NO:15.

Figure 9A:
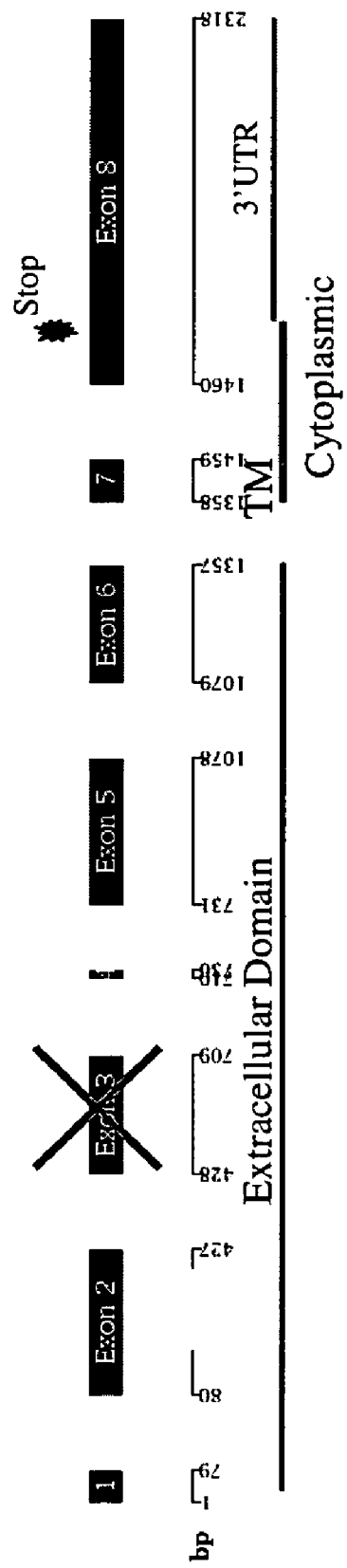
FIG. 9a shows the structure of a first category of splice variants of the murine BTL-II MRNA. The large X over exon 3 indicates that this exon is missing in this category of splice variants.

SEQ ID NO:17 is the nucleotide sequence of a representative member of a first category of murine BTL-II splice variants (FIG. 9a).

SEQ ID NO:18 is the amino acid sequence encoded by SEQ ID NO:17.

SEQ ID NO:19 is the nucleotide sequence encoding the BTL-II:Fc fusion protein described in Example 5.

SEQ ID NO:20 is the amino acid sequence of the BTL-II:Fc fusion protein described in Example 5.

DETAILED DESCRIPTION

The present invention provides BTL-II proteins and nucleic acids, including recombinant vectors encoding BTL-II proteins, anti-BTL-II antibodies, which can be agonists or antagonists, as well as methods for producing and using these molecules and pharmaceutical compositions containing them. BTL-II expression is restricted to a small number of tissue types. BTL-II is overexpressed in the gut prior to the onset of symptoms and during the symptomatic phase in a murine inflammatory bowel disease model system as illustrated in Example 4. BTL-II antibodies can therefore serve to diagnose or to predict the likelihood of the onset of an inflammatory bowel disease. In addition, the invention provides a number of allelic variants of the BTL-II nucleotide sequence (FIGS. 5a to 7a). These can find use in predicting susceptibility to inflammatory bowel disease. Further, since a soluble BTL-II protein can inhibit T cell proliferation and cytokine production (Examples 6–10), BTL-II proteins can find use in the treatment of autoimmune and inflammatory diseases.

Further, BTL-II is expressed in Peyer's patches, which are specialized structures known to play a role in immune sampling in the gut. BTL-II is preferentially expressed on are CD11c$^+$ (low expressing) CD8$^+$ B220$^+$ dendritic cells (also called plasmacytoid dendritic cells) found in Peyer's patches as compared to other cells found in Peyer's patches, including other dendritic cells. Peyer's patch dendritic cells have been hypothesized to play a role in inducing tolerance at mucosal surfaces due to their influence on T cell differentiation. Weiner (2001), Nature Immunology 2 (8): 671–71; Weiner (2001), Immunol. Rev. 182: 207–14; Iwasaki and Kelsall (1999), American Journal of Physiology-Gastrointestinal and Liver Physiology 276 (5): G1074–78. Thus, anti-BTL-II antibodies can be used to identify CD11c$^+$ (low expressing) CD8$^+$ B220$^+$ dendritic cells within Peyer's patches.

As explained below, BTL-II is within the B7 subfamily of butyrophilin-like proteins that play roles in regulating T and B cell-mediated responses. BTL-II may play a role in either dampening and/or promoting immune system-mediated inflammation, especially in the gut. Given the complexity of the immune system, a single cell surface protein may, in some cases, both stimulate or dampen an immune response by immune effector cells, depending on what receptors on the effector cells are available for the molecule to interact with. The B7-1 and B7-2 proteins discussed below are examples of immune-regulating cell surface proteins with both stimulatory and dampening effects on immune effector cells, in this case, T cells. Hence, BTL-II may play similar dual roles in vivo. However, the gut is, overall, highly tolerant to foreign antigens, as evidenced by its tolerance to food antigens and commensal microorganisms. It is therefore likely that BTL-II plays a role in dampening immune responses or inflammation in vivo in at least some situations. Thus, BTL-II antagonists, which can include antibodies, binding proteins selected in vitro, or small molecules, may serve to stimulate a mucosal immune response to an antigen. Further, soluble BTL-II proteins, or functionally equivalent anti-idiotypic antibodies, may dampen an immune response in the gut or in other mucosal surfaces in the body, such as the lungs.

An "antibody," as used herein, can be a chimeric antibody, can be monomeric or single chain, dimeric, trimeric, tetrameric, or multimeric antibody, and can be a recombinant protein or a non-recombinant protein. A "domain" is part or all of a protein that can be distinguished by primary sequence motifs and/or tertiary structural characteristics. Programs designed to locate protein domains include, for example, Pfam (Bateman et al. (1999), Nucleic Acids Res. 27: 260–62; Bateman et al. (1999), Nucleic Acids Res. 28: 263–66), ProDom (Corpet et al. (1999), Nucleic Acids Res. 27: 263–67; Corpet et al. (1999), Nucleic Acids Res. 28: 267–69), Domo (Gracy and Argos (1998), Bioinformatics 14: 164–87), and SMART (Ponting et al. (1999), Nucleic Acids Res. 27: 229–32). Tertiary structure can be determined empirically, for example by X-ray crystallography, or can be predicted using computer software designed for such uses. For example, structural data can be accessed through the Entrez website of NCBI from the Molecular Modeling Database (Wang et al. (2000), Nucleic Acids Res. 28 (1): 243–45) or by the use of software such as DALI (Holm and Sander (1993), J. Mol. Biol. 233: 123–38). Immunoglobulin-like domains (Ig-like), for example, are distinguished mainly by their tertiary structure rather than by primary sequence homologies. See e.g. Bork et al. (1994), J. Mol. Biol. 242: 309–20; Hunkapiller and Hood (1989), Adv. Immunol. 44: 1–63; Williams and Barclay (1988), Ann. Rev. Immunol. 6: 381–405. However, IgV and IgC domains do contain a handful of highly conserved amino acids that occur at conserved positions within their primary amino acid sequence. See e.g. Kabat et al. (1991), Sequences of Proteins of Immunological Interest, U.S. Dept. of Health and Human Services, Public Health Service, National Institutes of Health, NIH Publication No. 91-3242. The presence of such highly conserved amino acids occurring in the proper spacing can indicate the presence of an IgC-like or IgV-like domain.

A nucleic acid "encodes" a protein, as meant herein, if the nucleic acid or its complement comprises the codons encoding the protein.

Cells have been "genetically engineered" to express a specific protein when recombinant nucleic acid sequences that allow expression of the protein have been introduced into the cells using methods of "genetic engineering," such as viral infection, transfection, transformation, or electroporation. See e.g. Kaufman et al. (1990), Meth. Enzymol. 185: 487–511. This can include, for example, the introduction of nucleic acids encoding the protein into the cells or the introduction of regulatory sequences to enhance the expression of a host gene encoding the protein as described in U.S. Pat. No. 5,272,071 to Chappel. The methods of "genetic engineering" encompass numerous methods including, but not limited to, amplifying nucleic acids using polymerase chain reaction, assembling recombinant DNA molecules by cloning them in *Escherichia coli*, restriction enzyme digestion of nucleic acids, ligation of nucleic acids, in vitro synthesis of nucleic acids, and transfer of bases to the ends of nucleic acids, among numerous other methods that are well-known in the art. See e.g. Sambrook et al., Molecular Cloning: A Laboratory Manual, $2^{nd}$ ed., vol. 1–3, Cold Spring Harbor Laboratory, 1989.

A "heterologous polypeptide" is any polypeptide that is at least 3 amino acids long that is not a BTL-II polypeptide as meant herein.

In connection with comparisons to determine sequence identity of polynucleotides or polypeptides, what is meant by an "identity region" is the portion of the polynucleotide or polypeptide that is matched, partially or exactly, with another polynucleotide or polypeptide by the computer program GAP (Devereux et al. (1984), Nucleic Acids Res.

12: 387–95) using the parameters stated below. For example, when a polypeptide of 20 amino acids is aligned with a considerably longer protein, the first 10 amino acids match the longer protein exactly, and the last 10 amino acids do not match the longer protein at all, the identity region is 10 amino acids. If, on the other hand, the first and last amino acids of the 20 amino acid polypeptide match the longer protein, and eight other matches are scattered between, the identity region is 20 amino acids long. However, long stretches in either aligned strand without identical or conservatively substituted amino acids or identical nucleotides of at least, for example, 20 amino acids or 60 nucleotides constitute an endpoint of an identity region, as meant herein.

"Ig-like" domains are immunoglobulin like domains and may be either IgV-like or IgC-like domains or be domains that can fold into an immunoglobulin structure but cannot be unambigously classified as either IgV-like or IgC-like.

"IgV-like" domains have amino acid sequences that can be folded into an immunoglobulin fold with the characteristics common to immunoglobulin variable region domains. See Bork et al., supra; Miller et al. (1991), Proc. Natl. Acad. Sci. USA 88: 4377–81; Williams and Barclay (1988), Ann. Rev. Immunol. 6: 381–405. One of skill in the art is aware that the presence of amino acids that are highly conserved in IgV domains at conserved positions can identify a domain as IgV-like.

"IgC-like" domains have amino acid sequences that can be folded into an immunoglobulin fold with the characteristics common to immunoglobulin constant region domains. See Bork et al., supra; Williams and Barclay, supra. One of skill in the art is aware that the presence of amino acids that are highly conserved in IgC domains at conserved positions can identify a domain as IgC-like.

"Inflammatory bowel diseases" include Crohn's disease, ulcerative colitis, ileitis, and any other disease characterized by chronic inflammation of the gastrointestinal tract.

A protein comprises "no more or less than 2 Ig-like domains" when it contains two Ig-like domains and does not contain all or some recognizable portion of another Ig-like domain. However, such a protein can contain other amino acid sequences that are not Ig-like domains and still contain "no more or less than 2 Ig-like domains." Thus, the phrase "no more or less" refers only to Ig-like domains, not to other amino acid sequences that may be part of the protein.

When a polypeptide is said to be able to "inhibit the proliferation of T cells" or to be able to perform some other biological function, it is meant that a protein comprising the polypeptide can perform the function and that the addition of the polypeptide to at least some proteins that cannot perform the biological function enables these proteins to perform the function. In some cases, a polypeptide that can perform the biological function can do so without any additional sequences. In other cases, a polypeptide may require other sequences, for example, oligomerization sequences, to perform a biological function. In one scenario, a polypeptide may be able to effectively perform a particular biological function when it is linked to an Fc region or a leucine zipper or some other dimerizing domain, but not without the dimerizing domain. As meant herein, such a polypeptide can perform the biological function.

A "protein" is any polypeptide comprising at least 10 amino acids, optionally at least 20, 30, 40, 50, 60, 80, 100, 150, 200, 250, and/or 300 amino acids.

"Recombinant," as it applies to polypeptides or proteins, means that the production of the protein is dependent on at least one step in which nucleic acids, which may or may not encode the protein, are introduced into a cell in which they are not naturally found.

"Recombinant fusion proteins" are recombinant proteins comprising part or all of at least two proteins, which are not found fused together in nature, fused into a single polypeptide chain.

A "silent mutation" in a nucleic acid sequence is one that changes the sequence of the nucleic acid without changing the sequence of the protein encoded by the nucleic acid.

A "soluble" protein is one lacking a transmembrane domain or some other amino acid sequence, such as a GPI anchor sequence, that normally causes the protein to be embedded in or to associate with a membrane. Such proteins might typically comprise all or part of the extracellular region of a transmembrane protein.

For the purposes of the invention, two proteins or nucleic acids are "substantially similar" if they are at least 80%, optionally at least 85%, 90%, 95%, 97%, 98%, 99%, 99.5%, or 99.7% identical to each other in amino acid or nucleotide sequence and maintain or alter in a desirable manner a biological activity of the unaltered protein. The percent identity of two amino acid or two nucleic acid sequences can be determined by visual inspection and mathematical calculation, or more preferably, the comparison is done by comparing sequence information using a computer program. An exemplary computer program is the Genetics Computer Group (GCG; Madison, Wis.) Wisconsin package version 10.0 program, GAP (Devereux et al. (1984), Nucleic Acids Res. 12: 387–95). The preferred default parameters for the GAP program includes: (1) The GCG implementation of a unary comparison matrix (containing a value of 1 for identities and 0 for non-identities) for nucleotides, and the weighted amino acid comparison matrix of Gribskov and Burgess, ((1986) Nucleic Acids Res. 14: 6745) as described in *Atlas of Polypeptide Sequence and Structure*, Schwartz and Dayhoff, eds., National Biomedical Research Foundation, pp. 353–358 (1979) or other comparable comparison matrices; (2) a penalty of 8 for each gap and an additional penalty of 2 for each symbol in each gap for amino acid sequences, or a penalty of 50 for each gap and an additional penalty of 3 for each symbol in each gap for nucleotide sequences; (3) no penalty for end gaps; and (4) no maximum penalty for long gaps. Other programs used by those skilled in the art of sequence comparison can also be used.

Butyrophilin-Like Proteins

Figure 1:
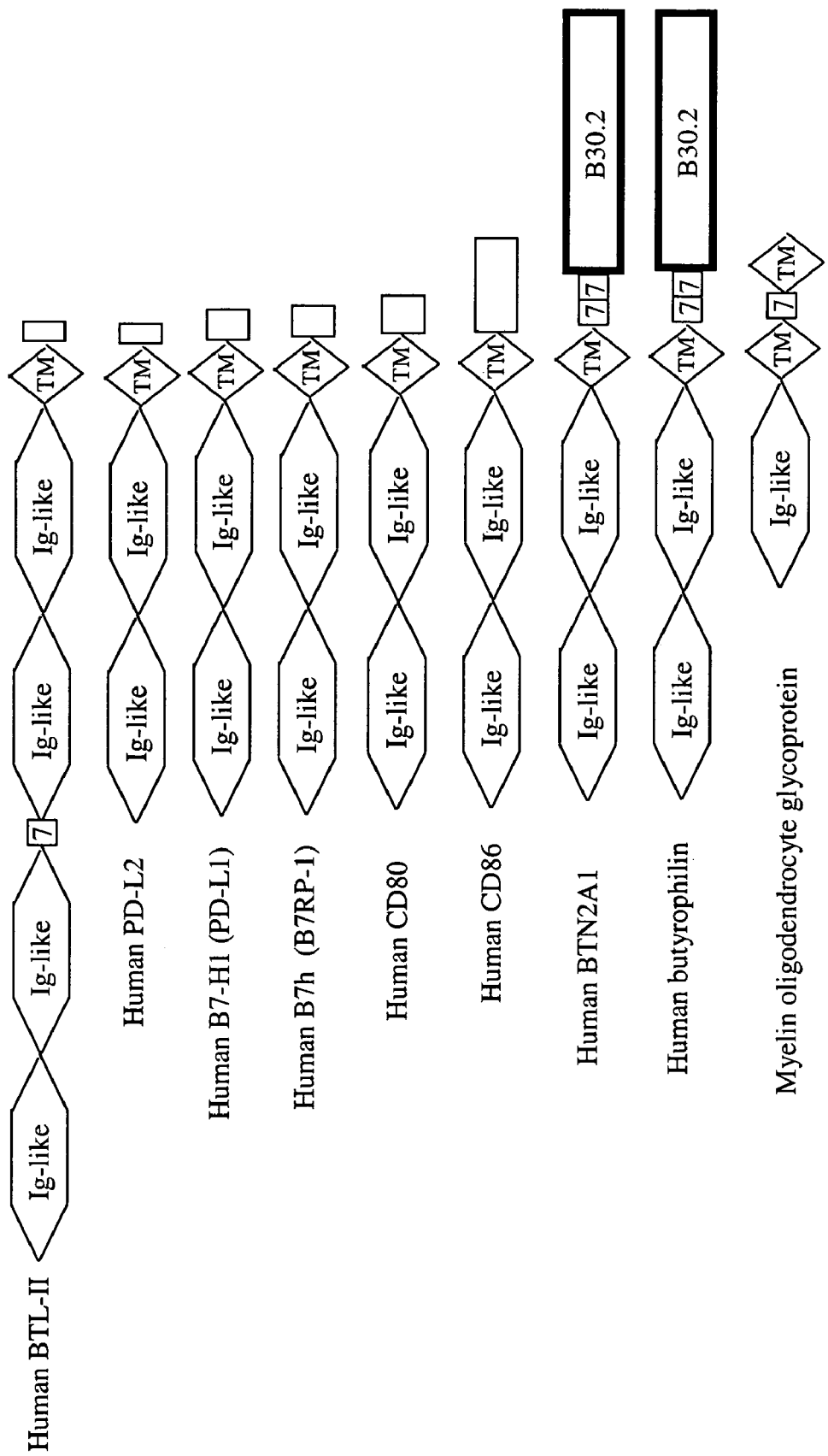
FIG. 1 shows the domain structures of selected members of the family of butyrophilin-like proteins. Most of the selected proteins are members of the B7 subfamily discussed below. The name of each protein is shown to the left of the diagram depicting its structure. The "Ig-like" domains are immunoglobulin-like domains as described below. The domains labeled "7" are heptad repeat regions as described below. The domains labeled "TM" are transmembrane domains. Open boxes are cytoplasmic domains not identified are part of a specific family of domains. Domains labeled "B30.2" are B30.2 domains as explained below. The BTL-II protein is depicted here as having four Ig-like domains, but forms of BTL-II also exist that have two or three Ig-like domains. B7-H3 is depicted with four Ig-like domains, and it also exists in a form containing only two Ig-like domains.
Figure 2:
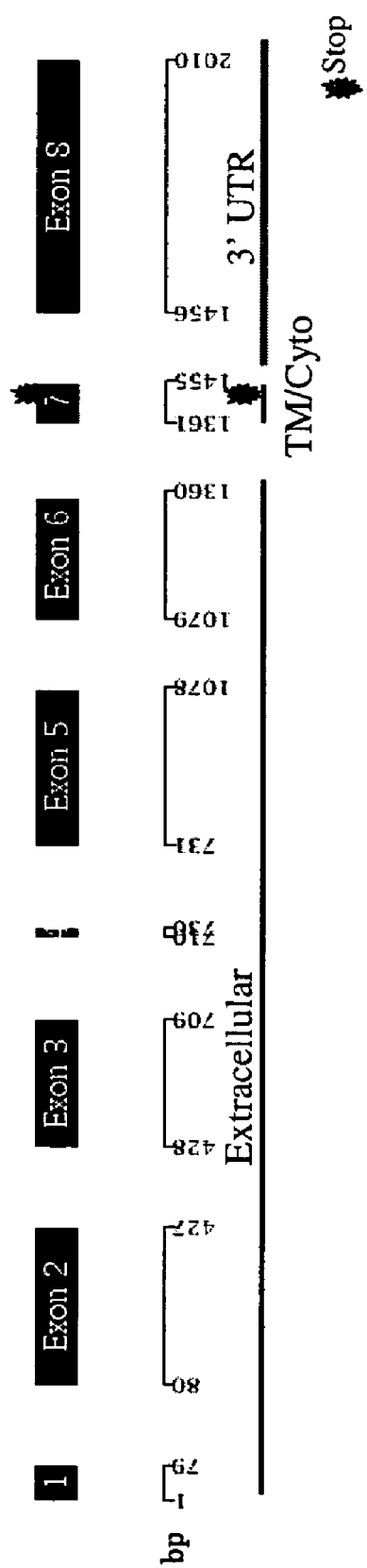
FIG. 2 is a diagram of the structure the human BTL-II gene and mRNA. The boxes indicate exons. The numbers below the horizontal lines below the boxes indicate the positions within SEQ ID NO:3 of the exons. The horizontal lines at the bottom of the figure denote the extent of SEQ ID NO:3 encoding the extracellular domain and the transmembrane and cytoplasmic domains ("TM/Cyto") and forming the 3' untranslated region ("3' UTR"). Stop codons are denoted by a mark that could be described as a sunburst or a small explosion.

Butyrophilin-like proteins reported to date share some structural features, and many are encoded within or adjoining the major histocompatability locus (MHC). See e.g. Henry et al. (1999), Immunology Today 20 (6): 285–88. Butyrophilin is a protein that constitutes 40% of the total protein associated with the fat globule of bovine milk, and a human homolog exists. Ruddy et al. (1997), Genome Research 7:441–56, citing Jack and Mather (1990), J. Biol. Chem. 265: 14481–86. Similarity at the amino acid sequence level among butyrophilin-like proteins can be low, but domain structure is somewhat conserved. All members comprise an amino terminal signal peptide followed by an Ig-like domain, usually reported to be an IgV-like domain. In many cases, this is followed by another Ig-like domain, usually reported to be an IgC-like domain, a transmembrane domain, and a cytoplasmic domain. The two Ig-like domains can be repeated immediately following their first occurrence, as in BTL-II or B7-H3. This domain structure is illustrated in FIG. 1. Most of the proteins diagrammed in FIG. 1 are members of the B7 subfamily of butyrophilin-like proteins; only three (human BTN2A1, human butyrophilin, and myelin oligodendrocyte glycoprotein) are not.

Ig-like domains can be very divergent in sequence and still retain one of a number of conserved folding patterns, which all include a common structural core comprising four β strands. Immunoglobulin constant and variable regions have a tertiary structure which is characterized by seven to nine antiparallel β strands forming a barrel-like shape. Bork et al. (1994), J. Mol. Biol. 242: 309–20. IgV- and IgC-like immunoglobulin domains each include a handful of distinct, highly conserved residues. Hunkapiller and Hood (1989), Adv. Immunol. 44: 1–63; Miller et al. (1991), Proc. Natl. Acad. Sci. USA 88: 4377–81; Williams and Barclay (1988), Ann. Rev. Immunol. 6: 381–405. Conserved residues are presumably important for structure or function. Such conserved residues are found in the Ig-like domains of BTL-II. For example, the first Ig-like domain of the human BTL-II protein (SEQ ID NO:4) contains such highly conserved residues characteristic of IgV-like domains in the appropriate locations at, for example, positions G43, C50, W65, L109, D118, G120, Y122 and C124. See Table 3. The third Ig-like domain also contains residues that correspond to residues conserved in IgV-like domains. The second and fourth Ig-like domains of human BTL-II contain contain residues that correspond to highly conserved residues in IgC-like domains. Table 3.

Transmembrane and cytoplasmic domains occur in butyrophilin-like proteins, regardless of whether they have a second Ig-like domain. The transmembrane domain may or may not be followed by one or more seven amino acid units reminiscent of the heptad repeats typical of an α-helical coiled coil motif. Heptad repeats may also occur at other positions in a butyrophilin-like protein. For a discussion of heptad repeats, see Miller et al. (1991), Proc. Nat. Acad. Sci. 88: 4377–81. Methods for predicting transmembrane domains are well known in the art. See e.g. Ikeda et al. (2002), In Silico Biol. 2 (1): 19–33; Tusnady and Simon (1998), J. Mol. Biol. 283 (2):489–506. Butyrophilin-like proteins can have a cytoplasmic domain. Such a cytoplasmic domain may or may not comprise a B30.2 domain. Sequences of various B30.2 domains are displayed, and putative functions of B30.2 domains are discussed by Henry et al. ((1998), Mol. Biol. Evol. 15 (12): 1696–1705. B30.2 domains are found in a variety of proteins, and the function of the B30.2 domain is unknown. A proposed ligand of the B30.2 domain is xanthine oxidase, which interacts with the cytoplasmic domain of butyrophilin. Mutations in B30.2 domains of two different B30.2-containing proteins have been correlated with two different diseases, although causal relationships between the mutations and the disease phenotypes have not been established. Henry et al., supra.

The B7 Subfamily of Butyrophilin-Like Proteins

BTL-II shares a domain structure with a number of butyrophilin-like immune regulatory proteins lacking the B30.2 domain that play roles in regulating immune effector cells, such as, for example, T cells, B cells and myeloid cells. This subfamily is referred to herein as "the B7 subfamily" of butyrophilin-like proteins. As meant herein, characteristics of B7 subfamily members include, without limitation, the following: (1) having one or more extracellular Ig-like domains; (2) having transmembrane and cytoplasmic domains; (3) lacking a B30.2 domain; (4) being expressed on antigen presenting cells; (5) undergoing regulation of expression during an activated immune response; and (6) modulating an immune response. No secreted, soluble B7 proteins, lacking a transmembrane domain, that modulate immune response have been reported to date. Most B7 proteins have two extracellular Ig-like domains, but some isoforms of B7-H3 have four. See FIG. 1. Human BTL-II can have from two to four extracellular Ig-like domains and has all of the characteristics of B7 family members listed above. We therefore consider it to be a member of the B7 subfamily of butyrophilin-like proteins. All other known members of the B7 subfamily interact with receptors on immune effector cells, such as B cells and/or T cells, which interaction serves as a signal to modulate an immune response. BTL-II is therefore predicted to interact with a receptor on an immune effector cell, such as a T cell, and thereby to modulate an immune response.

B7 family members play roles in modulating the activity of immune effector cells, especially T cells. Henry et al. (1999), Immunology Today 20 (6): 285–88; Sharpe and Freeman (2002), Nat. Rev. Immunol. 2: 116–26. The best characterized examples are, CD80 and CD86 (also called B7-1 and B7-2, respectively), which are expressed on antigen presenting cells and can promote T cell activation when they interact with CD28, which is constitutively expressed on the surface of T cells, or inhibit T cell activation when they interact with a CTLA-4, which is also expressed on the surface of T cells. CTLA-4 expression is not constitutive, but is rapidly upregulated following T cell activation. See e.g. Masteller et al. (2000), J. Immunol. 164: 5319–27; Hehner et al. (2000), J. Biol. Chem. 275 (24): 18160–71; Sharpe and Freeman (2002), Nat. Rev. Immunol. 2: 116–26. Moreover, it has been reported that numerous individual amino acid residues in both Ig-like domains of CD80 are important for binding to CTLA-4 and CD28. Peach et al. (1995), J. Biol. Chem. 270 (36): 21181–87. CD86 is constitutively expressed at low levels and is rapidly upregulated after activation, whereas CD80 is inducibly expressed later after activation. Sharpe and Freeman (2002), Nature Reviews Immunology 2: 116–26.

Another T cell regulatory molecule, referred to herein as B7RP-1, has a plethora of names, KIAA0653 (Ishikawa et al. (1998), DNA Res. 5: 169–76), B7h (Swallow et al. (1999), Immunity 11: 423–32), GL50 (Ling et al. (2000), J. Immunol. 164: 1653–57), B7RP-1 (Yoshinaga et al. (1999), Nature 402: 827–32), LICOS (Brodie et al. (2000), Curr. Biol. 10: 333–36), B7-H2 (Wang et al. (2000), Blood 96:2808–13), and ICOSL (Sharpe and Freeman, supra). B7RP-1 is expressed in peripheral lymphoid tissues, spleen, lymph nodes, lung, thymus, splenocytes, and B cells. Interaction of B7RP-1 with T cells can increase T cell proliferation and cytokine production. B7RP-1 signals T cells through the ICOS receptor, which is expressed on activated T cells. Yoshinaga et al. (1999), Nature 402: 827–32; Swallow et al. (1999), Immunity 11: 423–32. B7RP-1 is constitutively expressed in unstimulated B cell lines, and its expression can be induced in monocytes by interferon γ. Aicher et al. (2000), J. Immunol. 164: 4689–96. The development and regulatory function of regulatory T cells is dependent on the interaction between B7RP-1 and its receptor on T cells. Akbari et al. (2002), Nature Medicine 8 (9):1024–32.

Further, three other T cell regulatory molecules, PD-L1 (also called B7-H1), PD-L2 (also called B7-DC), and B7-H4 (also called B7S 1 and B7x) can inhibit T cell proliferation and cytokine production. PD-L1 and PD-L2 act through their common receptor, PD-1, which is expressed on T cells, B cells, and myeloid cells. Freeman et al. (2000), J. Exp. Med. 192 (7): 1027–34; Dong et al. (1999), Nature Medicine 5 (12): 1365–69; Latchman et al. (2001), Nature Immunology 2 (3): 261–68; Tamura et al. (2001), Blood 97 (6): 1809–16; and Tseng et al. (2001), J. Exp. Med. 193 (7): 839–45. Expression of PD-L1 and PD-L2 can be induced by interferon γ, a generally pro-inflammatory cytokine. Latchman et al., supra. B7-H4 is expressed on B cells, macrophages, and dendritic cells and likely acts through BTLA, an inhibitory receptor expressed on B and T cells. Watanabe et al. (2003), Nature Immunology 4 (7): 670–79; Zang et al. (2003), Proc. Natl. Acad. Sci. 100 (18): 10388–92; Sica et al. (2003), Immunity 18: 849–61; Prasad et al. (2003), Immunity 18: 863–73; Carreno and Collins (2003), Trends Immunol. 24 (10): 524–27.

Still another butyrophilin-like protein that plays a costimulatory role in stimulating T cells is B7-H3. Chapoval et al. (2001), Nature Immunol. 2 (3):269–74. Like the other B7 family members, B7-H3 has a signal sequence, extracellular Ig-like domains, a transmembrane domain, and a cytoplasmic domain. The human B7-H3 gene encodes isoforms with two or four extracellular Ig-like domains. Sun et al. (2002), J. Immunol. 168: 6294–97. Expression of B7-H3 can be induced on dendritic cells by inflammatory cytokines. B7-H3 can stimulate proliferation and the cytotoxic response of T cells. B7-H3 acts through a putative T cell receptor that is distinct from CD28, CTLA-4, ICOS, and PD-1. Chapoval et al, supra.

BTL-II Proteins

The existence of human and murine BTL-II proteins has been predicted from genomic sequence. Stammers et al. (2000), Immunogenetics 51: 373–82. However, these authors found no evidence of a transmembrane or a cytoplasmic domain in human or murine BTL-II proteins based on genome analysis and no evidence of a transcript connecting exons 1–4 (which encode a signal peptide, two Ig-like domains, and a heptad repeat region, respectively) with exons 5 and 6 (which encode another two Ig-like domains, respectively) in PCR experiments designed to detect murine BTL-II mRNAs. Stammers et al., supra. Based on these findings, BTL-II was not placed in the B7 subfamily of cell surface, immunomodulatory proteins. Later sequence submissions to public databases by these same authors predict a human BTL-II mRNA of 1368 nucleotides, which includes exons 5 and 6, encoding a protein of 455 amino acids, which lacks a transmembrane domain and a cytoplasmic domain (NCBI accession no. NM_019602, which discloses SEQ ID NO:1 (human BTL-II cDNA sequence) and SEQ ID NO:2 (human BTL-II protein sequence)).

The BTL-II nucleic acid and protein sequences of the invention differ from these sequences in a number of respects. The cDNA sequence encodes a protein comprising a signal sequence, an extracellular domain, a transmembrane domain, and a cytoplasmic domain, unlike the previously reported BTL-II protein sequence, which contained no transmembrane or cytoplasmic domains. These characteristics, along with the expression pattern of BTL-II, place BTL-II within the B7 subfamily of butyrophilin-like proteins. Table 1 (below) highlights the differences between the BTL-II protein of the invention and the previously reported sequence. A BTL-II protein of the invention is shown on the top line (SEQ ID NO:4), and the BTL-II protein reported in NCBI accession no. NM_019602 is shown on the bottom line (SEQ ID NO:2). From this comparison, it is apparent that there are three mismatches between the two sequences (at positions 360, 454, and 455) and that SEQ ID NO:4 has 27 more amino acids, which constitute additional sequence in the extracellular domain as well as a transmembrane and a cytoplasmic domain. These sequences 99.3% identical according to the GAP program using the parameters recited above.

TABLE 1

Comparison of human BTL-II predicted protein sequences

```
MVDFPGYNLSGAVASFLFILLTMKQSEDFRVIGPAHPILAGVGEDALLTC 50
||||||||||||||||||||||||||||||||||||||||||||||||||
MVDFPGYNLSGAVASFLFILLTMKQSEDFRVIGPAHPILAGVGEDALLTC 50

QLLPKRTTMHVEVRWYRSEPSTPVFVHRDGVEVTEMQMEEYRGWVEWIEN 100
||||||||||||||||||||||||||||||||||||||||||||||||||
QLLPKRTTMHVEVRWYRSEPSTPVFVHRDGVEVTEMQMEEYRGWVEWIEN 100

GIAKGNVALKIHNIQPSDNGQYWCHFQDGNYCGETSLLLKVAGLGSAPSI 150
||||||||||||||||||||||||||||||||||||||||||||||||||
GIAKGNWALKIHNIQPSDNGQYWCHFQDGNYCGETSLLLKVAGLGSAPSI 150

HMEGPGESGVQLVCTARGWFPEPQVYWEDIRGEKLLAVSEHRIQDKDGLF 200
||||||||||||||||||||||||||||||||||||||||||||||||||
HMEGPGESGVQLVCTARGWFPEPQVYWEDIRGEKLLAVSEHRIQDKDGLF 200

YAEATLVVRNASAESVSCLVHNPVLTEEKGSVISLPEKLQTELASLKVNG 250
||||||||||||||||||||||||||||||||||||||||||||||||||
YAEATLVVRNASAESVSCLVHNPVLTEEKGSVISLPEKLQTELASLKVNG 250

PSQPILVRVGEDIQLTCYLSPKANAQSMEVRWDRSHRYPAVHVYMDGDHV 300
||||||||||||||||||||||||||||||||||||||||||||||||||
PSQPILVRVGEDIQLTCYLSPKANAQSMEVRWDRSHRYPAVHVYMDGDHV 300

AGEQMAEYRGRTVLVSDAIDEGRLTLQILSARPSDDGQYRCLFEKDDVYQ 350
||||||||||||||||||||||||||||||||||||||||||||||||||
AGEQMAEYRGRTVLVSDAIDEGRLTLQILSARPSDDGQYRCLFEKDDVYQ 350
```

TABLE 1-continued

Comparison of human BTL-II predicted protein sequences

```
EASLDLKVVGLGSSPLITVEGQEDGEMQPMCSSDGWFPQPHVPWRDMEGK 400
||||||||| |||||||||||||||||||||||||||||||||||||||
EASLDLKVVSLGSSPLITVEGQEDGEMQPMCSSDGWFPQPHVPWRDMEGK 400

TIPSSSQALTQGSHGLFHVQTLLRVTNISAVDVTCSISIPFLGEEKIATF 450
||||||||||||||||||||||||||||||||||||||||||||||||||
TIPSSSQALTQGSHGLFHVQTLLRVTNISAVDVTCSISIPFLGEEKIATF 450

SLSESRMTFLWKTLLVWGLLLAVAVGLPRKRS 482
    |||
    SLSGW . . . 455
```

Besides an overall similarity in domain structure as illustrated in FIG. 1, the B7 subfamily proteins have similarities at the primary sequence level. For example, when aligned pairwise using the computer program GAP, the human BTL-II protein sequence (SEQ ID NO:4) is similar to other B7 subfamily members as displayed in Table 2 below.

TABLE 2

|  | Percent identity to human BTL-II protein | Percent similarity to human BTL-II protein |
|---|---|---|
| Human PD-L1 (NCBI accession no. NP_054862) | 19% | 28% |
| Human PD-L2 (NCBI accession no. NP_079515) | 19% | 29% |
| Human CD80 (NCBI accession no. P33681) | 26% | 33% |
| Human CD86 (NCBI accession no. P42081) | 23% | 32% |
| Murine BTL-II | 62% | 68% |

One of skill in the art will realize that residues that are conserved in any of these alignments are more likely to play an essential role in the structure or function of human BTL-II than those that are not conserved.

In Table 3 (below), the human BTL-II amino acid sequence (SEQ ID NO:4, top line) is aligned with the murine BTL-II amino acid sequence (SEQ ID NO:6; bottom line). Identical amino acids are joined by a vertical line, and similar amino acids have one or two dots between them. The percent identity between these sequences as determined GAP (described above) is about 62%, and the percent similarity is about 68%. Residues found in IgV- or IgC-like domains or in the so-called "I set" of IgV-like immunoglobulin superfamily members or conservative substitutions of such residues are shown in boldface. Peach et al., supra; Harpaz and Chothia (1994), J. Mol. Biol. 238: 528–39. Such residues are likely to be structurally important and, thus, may have functional effects. The occurrence of a substantial number of such amino acids in the proper spacing can identify a sequence as IgV-like or IgC-like.

TABLE 3

```
  1 MVDFPGYNLSGAVASFLFILLTMKQSEDFRVIGPAHPILAGVGEDALLTC
    ||| |.||| ||||:|||.|  :||||:||  |||  ||||||||||
  1 MVDCPRYSLSGVAASFLFVLLTIKHPDDFRVVGPNLPILAKVGEDALLTC

51 QLLPKRTTMHVEVRWYRSEPSTPVFVHRDGVEVTEMQMEEYRGWVEWIEN
    ||||||||  |.|||||||:|. ||  .:|||  ||  :   || | ||.|.
 51 QLLPKRTTAHMEVRWYRSDPAMPVIMYRDGAVVTGLPMEGYGGRAEWMED

101 GIAKGNVALKIHNIQPSDNGQYWCHFQDGNYCGETSLLLKVAGLGSAPSI
    .|.||||  :||||.||||  ||:|.| |||.|.||  |||.|.|
101 STEEGSVALKIRQVQPSDDGQYWCRFQEGDYWRETSVLLQVAALGSSPNI

151 HMEGPGESGVQLVCTARGWFPEPQVYWEDIRGEKLLAVSEHRIQDKDGLF
    |.|| ||  ||||||.|||||||:|:||  |||:.  ||. :   .||||
151 HVEGLGEGEVQLVCTSRGWFPEPEVHWEGIWGEKLMSFSENHVPGEDGLF

201 YAEATLVVRNASAESVSCLVHNPVLTEEKGSVISLPEKLQTELASLKVNG
    |  ||.|||  |  |.:||  ::.  |  .|.| |:|||||.|  | |
201 YVEDTLMVRNDSVETISCFIYSHGLRETQEATIALSERLQTELVSVSVIG

251 PSQPILVRVGEDIQLTCYLSPKANAQSMEVRWDRSHRYPAVHVYMDGDHV
    |||  |.|||.|:|||:|||. .||.:|||| ||   |||||||  .| ||
251 HSQPSPVQVGENIELTCHLSPQTDAQNLEVRWLRSRYYPAVHVYANGTHV
```

TABLE 3-continued

```
301 AGEQMAEYRGRTVLVSDAIDEGRLTLQILSARPSDDGQYRCLFEKDDVYQ
    |||||  ||:|||  ||.|||  ||:|||||  .||  ||:||||||||  ||  |||
301 AGEQMVEYKGRTSLVTDAIHEGKLTLQIHNARTSDEGQYRCLFGKDGVYQ

351 EASLDLKVVGLGSSPLITVEGQEDGEMQPMCSSDGWFPQPHVPWRDMEGK
    ||  .|...|  ..||.|  |||  |  .||  ||  |.||||||.|||  |||  :||
351 EARVDVQVTAVGSTPRITREVLKDGGMQLRCTSDGWFPRPHVQWRDRDGK

401 TIPSSSQALTQGSHGLFHVQTLLRVTNISAVDVTCSISIPFLGEEKIATF
    |.||  |:|  |||  ||  |:|||  |||  |  |.||||||:|  ||:||  |  |
401 TMPSFSEAFQQGSQELFQVETLLLVTNGSMVNVTCSISLP.LGQEKTARF

451 SLSESRMTFLWKTLLVWGLLLAVAVGLPR.KRS*................
    ||:|:.  ||  |||  |  |  ||.|.|  :  ||
450 PLSDSKIALLWMTLPVVVLPLAMAMDLIKVKRRRRTNEQTHSSNQENNKN

483 ..................................................

500 DENHRRRPPSDERLR...................................
```

One of skill in the art will appreciate that non-conserved residues are less likely to play a role in determining the overall tertiary structure of a BTL-II protein than conserved residues, since structure is more conserved in evolution than sequence. Bork et al. (1994), J. Mol. Biol. 242: 309–20. As used herein, "non-conserved residues" are amino acids within a BTL-II protein that are not conserved when the human and the murine BTL-II protein sequences are compared as in Table 3. In BTL-II proteins encoded by splice variants, such residues will occur a different numerical positions within the sequence. For example, the non-conserved residue at position 397 of SEQ ID NO:4 is the same non-conserved residue seen at position 187 of SEQ ID NO:8. One of skill in the art will appreciate that protein structure can affect protein function. Further, non-conserved amino acids are also less likely to play a direct role in BTL-II function. For example, residues 4, 6, 25, 26, 35, 36, and many others are neither identical nor similar. Thus, one of skill in the art would realize that alteration of such residues would be less likely to affect BTL-II protein function that would alteration of conserved or similar residues. Moreover, conservative substitutions are less likely to affect protein function that non-conservative substitutions. Examples of amino acid substitutions that are conservative substitutions, unlikely to affect biological activity, including the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and these changes in the reverse. See e.g. Neurath et al., *The Proteins*, Academic Press, New York (1979). Further, an exchange of one amino acid within a group for another amino acid within the same group is a conservative substitution where the groups are the following: (1) alanine, valine, leucine, isoleucine, methionine, norleucine, and phenylalanine; (2) histidine, arginine, lysine, glutamine, and asparagine; (3) aspartate and glutamate; (4) serine, threonine, alanine, tyrosine, phenylalanine, tryptophan, and cysteine; (5) glycine, proline, and alanine;

Human BTL-II protein comprises several recognizable domains. First, is a signal sequence (encoded by exon 1), which extends from residue 1 of SEQ ID NO:4 to a second position from about residue 22 to 29 of SEQ ID NO:4. Next is an Ig-like domain (encoded by exon 2), which extends from residue x to residue y, where x is from residue 22 to 32 and y is from residue 138 to 148 of SEQ ID NO:4. Following this is another Ig-like domain (encoded by exon 3) extending from residue v to residue w, where residue v is from residue 138 to 148 and w is from residue 232 to 242 of SEQ ID NO:4. Next is a heptad repeat region (encoded by exon 4) from residue t to residue u, where t is from 234 to 239 and u is from residue 240 to 247 of SEQ ID NO:4. Another Ig-like region extends from residue r to residue s, where r is from residue 240 to 247 and s is from residue 354 to 364 of SEQ ID NO:4. A fourth Ig-like region extends from residue p to residue q, where p is from residue 355 to 365 and q is from residue 452 to 462 of SEQ ID NO:4. These first six domains of human BTL-II make up the extracellular region of human BTL-II. The signal sequence may, but need not, be cleaved from the rest of the protein upon secretion of the protein. A transmembrane domain extends from residue n to residue o, where n is from residue 454 to 462 and o is from residue 473 to 481 of SEQ ID NO:4. Finally, a cytoplasmic domain extends from residue k to residue m, where k is from residue 474 to 481 and m is at about residue 482 of SEQ ID NO:4.

Murine BTL-II protein comprises a similar set of domains. First is a signal sequence starting at residue 1 and ending at a position from about residue 20 to about residue 27 of SEQ ID NO:6. Second is an Ig-like domain extending from residue x to y, where x is from residue 21 to 27 and y is from residue 138 to 148 of SEQ ID NO:6. Third is another Ig-like domain from residue v to w, where v is from 139 to 148 and w is from 232 to 242 of SEQ ID NO:6. A heptad repeat region extends from residue t to u, where t is from 233 to 242 and u is from 238 to 248 of SEQ ID NO:6. Another Ig-like region extends from residue r to s, where r is from 239 to 248 and s is from 355 to 365 of SEQ ID NO:6. A final Ig-like region extends from residue p to q, where p is from 356 to 365 and q is from 447 to 457 of SEQ ID NO:6. These first six domains make up the extracellular region of murine BTL-II. A transmembrane domain extends from residue n to o, where n is from 448 to 459 and o is from 470 to 478 of SEQ ID NO:6. Finally, a cytoplasmic domain extends from residue k to m, where is from 471 to 478 and m is at about 514 of SEQ ID NO:6.

The instant invention encompasses secreted, soluble versions of BTL-II as well as versions comprising a transmembrane domain that can be expressed on a cell surface. The invention further includes BTL-II proteins encoded by the BTL-II nucleic acids described below. Recombinant versions of all of these proteins can be used to produce antibodies, in screening, and/or as therapeutic agents as described herein. For example, the invention encompasses BTL-II proteins comprising all or part of SEQ ID NO:4, SEQ ID NO:6, SEQ ID NO:8, SEQ ID NO:10, SEQ ID NO:12, SEQ ID NO:14, SEQ ID NO:16, and/or SEQ ID NO:18. BTL-II proteins of the invention include proteins that differ from SEQ ID NO:4, SEQ ID NO:6, SEQ ID NO:8, SEQ ID NO:10, SEQ ID NO:12, SEQ ID NO:14, SEQ ID NO:16, or SEQ ID NO:18 by insertion, deletion, alteration, or substitution in the primary amino acid sequence. Such variant sequences are at least 80%, 85%, 90%, 95%, 97%, 98%, 99%, 99.5%, or 99.7% identical to SEQ ID NO:4, SEQ ID NO:6, SEQ ID NO:8, SEQ ID NO:10, SEQ ID NO:12, SEQ ID NO:14, SEQ ID NO:16, and/or SEQ ID NO:18, and contain no internal gaps of over 10 amino acids when aligned using GAP with the above-mentioned sequences. Examples of such sequences include the naturally-occurring human allelic variants of BTL-II shown in FIGS. 5b, 6b, and 7b. If such variant sequences contain amino substitutions when compared to SEQ ID NO:4, SEQ ID NO:6, SEQ ID NO:8, SEQ ID NO:10, SEQ ID NO:12, SEQ ID NO:14, SEQ ID NO:16, and/or SEQ ID NO:18, these substitutions can be conservative amino acid substitutions. Further, variant BTL-II proteins may contain no more than 3, 4, 5, 6, 7, 8, 9, 10, 15, 20, or 25 insertions, deletions, or substitutions of a single amino acid with respect to SEQ ID NO:4, SEQ ID NO:6, SEQ ID NO:8, SEQ ID NO:10, SEQ ID NO:12, SEQ ID NO:14, SEQ ID NO:16, and/or SEQ ID NO:18.

The BTL-II proteins of the invention include proteins encoded by various splice variants of the human and mouse BTL-II mRNA. Sequences of such variant human BTL-II proteins are shown in SEQ ID NO:8, SEQ ID NO:10, SEQ ID NO:12, SEQ ID NO:14, and SEQ ID NO:16. The sequence of a variant mouse BTL-II protein is shown in SEQ ID NO:18. Human splice variants lack either exon 3 alone or lack both exons 2 and 3, and the murine splice variant disclosed lacks exon 3 only. See SEQ ID NO:7, SEQ ID NO:9, SEQ ID NO:11, SEQ ID NO:13, SEQ ID NO:15, and SEQ ID NO:17; FIGS. 3a, 4a, 5a, 6a, 7a, and 9a. Proteins encoded by these sequences and substantially similar sequences, where an alignment of the protein sequence with at least one of the group consisting of SEQ ID NO:4, SEQ ID NO:6, SEQ ID NO:8, SEQ ID NO:10, SEQ ID NO:12, SEQ ID NO:14, SEQ ID NO:16, or SEQ ID NO:18 using GAP comprises no gaps longer than 10 amino acids, are encompassed by the invention. If these proteins contain amino acid substitutions relative to SEQ ID NO:4, SEQ ID NO:6, SEQ ID NO:8, SEQ ID NO:10, SEQ ID NO:12, SEQ ID NO:14, SEQ ID NO:16, and/or SEQ ID NO:18, such substitutions are preferably conservative amino acid substitutions. BTL-II proteins of the invention can bind to a receptor on the surface of a T cell and can inhibit proliferation and/or cytokine production by T cells.

Further, the invention provides BTL-II proteins encoded by nucleic acids that span the splice junctions of exons 1 and 4 (SEQ ID NO:8 and SEQ ID NO:12) or exons 2 and 4 (SEQ ID NO:10, SEQ ID NO:14, SEQ ID NO:16, and SEQ ID NO:18) and substantially similar proteins that can bind to a receptor expressed on the surface of T cells and/or can inhibit proliferation and/or cytokine production by T cells. This specifically includes BTL-II proteins comprising a polypeptide consisting of an amino acid sequence at least 80%, 85%, 90%, 95%, 96%, 97%, 98%, 99%, 99.7%, or 100% identical to amino acids 127 to 157 of SEQ ID NO:10, SEQ ID NO:14, or SEQ ID NO:18 or amino acids 126 to 156 of SEQ ID NO:16. The identity region of the amino acid sequence aligned with amino acids 127 to 157 of SEQ ID NO:10, SEQ ID NO:14, or SEQ ID NO:18 or amino acids 126 to 156 of SEQ ID NO:16 is preferably at least 20, 23, 25, 27, 30, 35, or 40. amino acids long. Such an amino acid sequence can be at least 150 amino acids long and can be at least 80%, 85%, 90%, 95%, 96%, 97%, 98%, 99%, 99.7%, or 100% identical to amino acids 30 to 358 of SEQ ID NO:10, SEQ ID NO:14, SEQ ID NO:16, or SEQ ID NO:18. The identity region of the amino acid sequence aligned with amino acids 30 to 358 of SEQ ID NO:10, SEQ ID NO:14, SEQ ID NO:16, or SEQ ID NO:18 can be at least 50, 75, 100, 125, 150, 175, 200, or 300 amino acids.

The invention also provides BTL-II proteins comprising a polypeptide consisting of an amino acid sequence at least 80%, 85%, 90%, 95%, 96%, 97%, 98%, 99%, 99.7%, or 100% identical to amino acids 30 to 457 of SEQ ID NO:4 that contains no more or less than 2 Ig-like domains and that can bind to a cell surface receptor expressed on B cells or T cells. The amino acid sequence can be at least 80%, 85%, 90%, 95%, 96%, 97%, 98%, 99%, 99.7%, or 100% identical to amino acids 30 to 247 of SEQ ID NO:8 or to amino acids 30 to 243 of SEQ ID NO:12.

In further embodiments, the invention provides proteins encoded by nucleic acids comprising a polynucleotide that is 80%, 85%, 90%, 95%, 96%, 97%, 98%, 99%, 99.7%, or 100% identical to a polynucleotide consisting of nucleotides 34 to 124 of SEQ ID NO:11, where the identity region is at least 60, 70, 80, 90, or 100 nucleotides long. Mature BTL-II proteins encoded by such polynucleotides may, but need not, lack a signal sequence (which is present in the immature version of the protein) that is at least partially encoded by this polynucleotide. Such proteins can bind to a T cell and/or can inhibit proliferation and/or cytokinine production by the T cell.

BTL-II proteins may be glycosylated to varying degrees or not glycosylated. As an illustration, a BTL-II protein of the invention may comprise one or more N- or O-linked glycosylation sites in addition to those already found in a protein comprising SEQ ID NO:4, SEQ ID NO:6, SEQ ID NO:8, SEQ ID NO:10, SEQ ID NO:12, SEQ ID NO:14, SEQ ID NO:16, and/or SEQ ID NO:18. Such a BTL-II protein can have a longer in vivo half life than an unaltered protein since it may have more sialic acid moieties attached to it. BTL-II proteins also include proteins comprising any one, any two, any three, or all four of the Ig-like domains of a human or murine BTL-II or substantially similar domains.

Variants

Polypeptides derived from any BTL-II protein by any type of alteration (for example, but not limited to, insertions, deletions, or substitutions of amino acids; changes in the state of glycosylation of the polypeptide; refolding or isomerization to change its three-dimensional structure or self-association state; and changes to its association with other polypeptides or molecules) are also BTL-II proteins as meant herein. The BTL-II proteins provided by the invention include polypeptides characterized by amino acid sequences substantially similar to those of the BTL-II proteins SEQ ID NO:4, SEQ ID NO:6, SEQ ID NO:8, SEQ ID NO:10, SEQ ID NO:12, SEQ ID NO:14, SEQ ID NO:16, and/or SEQ ID NO:18 that can bind to a receptor expressed on the surface of T cells and/or can inhibit proliferation of and/or cytokine production of a T cell. The region of identity can start at position 30 or higher of SEQ ID NO:4, SEQ ID NO:6, SEQ ID NO:8, SEQ ID NO:10, SEQ ID NO:12, SEQ ID NO:14, SEQ ID NO:16, or SEQ ID NO:18. A GAP alignment of such a variant protein with at least one of SEQ ID NO:4, SEQ ID NO:6, SEQ ID NO:8, SEQ ID NO:10, SEQ ID NO:12, SEQ ID NO:14, SEQ ID NO:16, and/or SEQ ID NO:18 may have no internal gaps longer than 10 amino acids. The portion of the BTL-II protein that is substantially similar to SEQ ID NO:4, SEQ ID NO:6, SEQ ID NO:8, SEQ ID NO:10, SEQ ID NO:12, SEQ ID NO:14, SEQ ID NO:16, or SEQ ID NO:18 can be at least 100, at least 125, at least 150, at least 175, at least 200, or at least 250 amino acids long. Modifications in such proteins can be naturally provided or deliberately engineered. For example, SEQ ID NO:11 (FIG. 6*a*) is an allelic or polymorphic variant of SEQ ID NO:9 (FIG. 4*a*) containing base changes at a handful of positions including at positions.

The invention provides BTL-II protein variants that contain single or multiple amino acid alterations, which can be insertions, deletions, or substitutions of a single amino acid, relative to the sequence of SEQ ID NO:4, SEQ ID NO:6, SEQ ID NO:8, SEQ ID NO:10, SEQ ID NO:12, SEQ ID NO:14, SEQ ID NO:16, or SEQ ID NO:18, wherein the BTL-II variant protein can inhibit T cell proliferation and/or cytokine production. The alterations can be conservative amino acid substitutions. One of skill in the art is guided as to what amino acids can be changed without affecting function by, for example, the alignment of human and mouse BTL-II proteins shown in Table 3. Amino acids that are identical or similar in human and mouse BTL-II are more likely to be important for function that those that are not. Further, amino acids that are highly conserved in IgV or IgC domains (shown in boldface in Table 3) are also likely to be functionally important. Such allelic or polymorphic variants can be valuable as diagnostic agents to determine a predisposition to disease. Human allelic variants with sequences varying from SEQ ID NO:3 are disclosed in FIGS. 5*a*, 5*b*, 6*a*, 6*b*, 7*a*, and 7*b*. For example, among normal people without symptoms of inflammatory bowel disease, a certain ratio can exist between the number having BTL-II genes encoding cDNAs with the sequence of SEQ ID NO:3 and the number having BTL-II genes encoding the allelic variant mutations labeled 3–6 in FIGS. 5*a*, 6*a*, and 7*a*. The ratio of the occurrence of these alleles may be altered among patients with symptoms of inflammatory bowel disease such that a greater proportion of these people have BTL-II genes with the allelic variant mutations labeled 3–6 in FIGS. 5*a*, 6*a*, and 7*a*. The existence of various allelic variations in a patient's tissues can be determined by, for example, PCR amplification of a segment of a DNA or RNA molecule spanning the polymorphic site. As mentioned above, conservative amino acid substitutions, particularly at sites not conserved between human and mouse BTL-II protein sequences, are more likely to preserve biological function that are non-conservative substitutions at conserved sites. One of skill in the art will also appreciate that substitutions that substantially upset the tertiary structure of a BTL-II protein as predicted by programs such as, for example, DALI (Holm and Sander (1993), J. Mol. Biol. 233: 123–38), are likely to also impair function.

Fragments

Included among BTL-II proteins are proteins comprising fragments of SEQ ID NO:4, SEQ ID NO:6, SEQ ID NO:8, SEQ ID NO:10, SEQ ID NO:12, SEQ ID NO:14, SEQ ID NO:16, or SEQ ID NO:18 or fragments that are at least 80%, 85%, 90%, 95%, 97%, 98%, 99%, 99.5%, or 99.7% identical to these sequences. Preferably, such fragments can bind to a receptor expressed on the surface of a T cell and are at least about 50, 60, 70, 80, 90, 100, 150, or 200 amino acids long. Preferably, such fragments are soluble in aqueous solution and comprise part or all of the extracellular region of a BTL-II protein. The protein comprising such a fragment can be secreted. For example, BTL-II proteins comprising at least one of the domains of the human or murine BTL-II proteins described above or a substantially similar protein, wherein the domain has at least one of the biological properties of BTL-II proteins, are encompassed by the invention. For example, such proteins can inhibit proliferation and/or cytokine production of T cells.

Further, encompassed by the invention are the following altered versions the human and murine BTL-II proteins or substantially similar proteins: (1) versions of the human and murine BTL-II protein lacking the second Ig-like domain (see FIG. 1) encoded by exon 3; (2) versions of a human or murine BTL-II protein lacking the first and second Ig-like domains encoded by exons 2 and 3; (3) versions lacking third and fourth Ig-like domains encoded by exons 5 and 6; (4) versions lacking any two of the four Ig-like domains; and (5) versions lacking any one of the Ig-like domains.

Also encompassed within the invention are immunogenic fragments of SEQ ID NO:4, SEQ ID NO:6, SEQ ID NO:8, SEQ ID NO:10, SEQ ID NO:12, SEQ ID NO:14, SEQ ID NO:16, or SEQ ID NO:18 that are capable of eliciting antibodies that bind specifically to the fragment. Such fragments are preferably at least 10 amino acids long and preferably comprise contiguous amino acid residues from sequences mentioned above. Antibodies generated by immunizing animals with such fragments can be useful for prediction, diagnosis, and treatment of inflammatory bowel diseases, as discussed elsewhere in this application. Such fragments can span regions of these proteins encoded by splice junctions, which may have the advantage of generating antibodies specific for proteins encoded by splice variants or the full length protein. Alternatively, an antibody against a portion of BTL-II that is encoded by exon 3 would detect only full length BTL-II proteins, not proteins encoded by any other splice variants, all of which lack exon 3.

Recombinant Fusion Proteins

The invention further encompasses fusion proteins comprising at least one BTL-II polypeptide, which is one of the BTL-II proteins, variants, or fragments described above, and at least one other moiety. The other moiety can be a heterologous polypeptide, that is, a polypeptide other than a BTL-II polypeptide. The other moiety can also be a non-protein moiety such as, for example, a polyethylene glycol (PEG) moiety or a cytotoxic, cytostatic, luminescent, and/or radioactive moiety. Attachment of PEG has been shown to increase the in vivo half life of at least some proteins. Moreover, cytotoxic, cytostatic, luminescent, and/or radioactive moieties have been fused to antibodies for diagnostic or therapeutic purposes, for example, to locate, to inhibit proliferation of, or to kill cells to which the antibodies can bind. Similarly, BTL-II polypeptides fused to such moieties can be used to locate, to inhibit proliferation of, or to kill cells that BTL-II can bind to. Among such cytotoxic, cytostatic, luminescent, and/or radioactive moieties are, for example, maytansine derivatives (such as DM1), enterotoxins (such as a Staphlyococcal enterotoxin), iodine isotopes (such as iodine-125), technetium isotopes (such as Tc-99 m), cyanine fluorochromes (such as Cy5.5.18), ribosome-inactivating proteins (such as bouganin, gelonin, or saporin-S6), and calicheamicin, a cytotoxic substance that is part of a product marketed under the trademark MYLOTARG™ (Wyeth-Ayerst).

A variety of heterologous polypeptides can be fused to a BTL-II polypeptide for a variety of purposes such as, for example, to increase in vivo half life of the protein, to facilitate identification, isolation and/or purification of the protein, to increase the activity of the protein, and to promote oligomerization of the protein. Since some proteins of the B7 subfamily, such as, for example, CD80, bind to their receptors primarily in oligomeric form (dimeric in the case of CD80; see Collins et al. (2002), Immunity 17: 201–10), oligomerization can be very important to preserve the biological activity of a soluble protein.

Many heterologous polypeptides can facilitate identification and/or purification of recombinant fusion proteins of which they are a part. Examples include polyarginine, polyhistidine, or HAT™ (Clontech), which is a naturally-occurring sequence of non-adjacent histidine residues that possess a high affinity for immobilized metal ions. Proteins comprising these heterologous polypeptides can be purified by, for example, affinity chromatography using immobilized nickel or TALON™ resin (Clontech), which comprises immobilized cobalt ions. See e.g. Knol et al. (1996), J. Biol. Chem. 27 (26): 15358–15366. Heterologous polypeptides comprising polyarginine allow effective purification by ion exchange chromatography. Other useful heterologous polypeptides include, for example, the antigenic identification peptides described in U.S. Pat. No. 5,011,912 and in Hopp et al. (1988), *Bio/Technology* 6:1204. One such peptide is the FLAG® peptide, which is highly antigenic and provides an epitope reversibly bound by a specific monoclonal antibody, enabling rapid assay and facile purification of expressed recombinant fusion protein. A murine hybridoma designated 4E11 produces a monoclonal antibody that binds the FLAG® peptide in the presence of certain divalent metal cations, as described in U.S. Pat. No. 5,011,912. The 4E11 hybridoma cell line has been deposited with the American Type Culture Collection under accession no. HB 9259. Monoclonal antibodies that bind the FLAG® peptide can be used as affinity reagents to recover a polypeptide purification reagent that comprises the FLAG® peptide. Other suitable protein tags and affinity reagents are: 1) those described in GST-Bind™ system (Novagen), which utilizes the affinity of glutathione-S-transferase fusion proteins for immobilized glutathione; 2) those described in the T7-Tag® affinity purification kit (Novagen), which utilizes the affinity of the amino terminal 11 amino acids of the T7 gene 10 protein for a monoclonal antibody; or 3) those described in the Strep-tag® system (Novagen), which utilizes the affinity of an engineered form of streptavidin for a protein tag. Some of the above-mentioned protein tags, as well as others, are described in Sassenfeld (1990), TIBTECH 8: 88–93, Brewer et al., *in Purification and Analysis of Recombinant Proteins*, pp.239–266, Seetharam and Sharma (eds.), Marcel Dekker, Inc. (1991), and Brewer and Sassenfeld, *in Protein Purification Applications*, pp. 91–111, Harris and Angal (eds.), Press, Inc., Oxford England (1990). Further, fusions of two or more of the tags described above, such as, for example, a fusion of a FLAG tag and a polyhistidine tag, can be fused to a BTL-II protein of the invention.

Recombinant fusion proteins comprising other heterologous polypeptides may have other kinds of unique advantages, such as, for example, a propensity to form dimers, trimers, or higher order multimers, an increased in vivo half-life, and/or an increased biological activity. Techniques for preparing fusion proteins are known, and are described, for example, in WO 99/31241 and in Cosman et al. ((2001). Immunity 14: 123–133). As an illustration, a heterologous polypeptide that comprises an Fc region of an IgG antibody, or a substantially similar protein, can be fused to a BTL-II polypeptide or fragment. An Fc region of an antibody is a polypeptide comprising $C_H2$ and $C_H3$ domains from an antibody of human or animal origin or immunoglobulin domains substantially similar to these. For discussion, see Hasemann and Capra, Immunoglobulins: Structure and Function, in William E. Paul, ed., Fundamental Immunology, Second Edition, 212–213 (1989). Truncated forms of Fc regions comprising the hinge region that promotes dimerization can also be used. Other portions of antibodies and other immunoglobulin isotypes can be used. Recombinant fusion proteins comprising Fc regions of IgG antibodies are likely to form dimers. Fusion proteins comprising various portions of antibody-derived proteins have been described by Ashkenazi et al. ((1991) Proc. Natl. Acad. Sci. USA 88:10535–39), Byrn et al. ((1990), Nature 344: 677–70), Hollenbaugh and Aruffo (in Current Protocols in Immunology, Suppl. 4, pp. 10.19.1–10.19.11 (1992)), Baum et al. ((1994), EMBO J. 13: 3992–4001) and in U.S. Pat. No. 5,457,035 and WO 93/10151. In some embodiments, an altered Fc region can have the advantage of having a lower affinity for Fc receptors compared to a wild type Fc region. This is an advantage because it may lessen the lysis of cells to which such recombinant fusion proteins bind by immune effector cells. Example 5 describes the production of a fusion protein containing the extracellular region of murine BTL-II fused to a human Fc region. The nucleic acid sequence encoding this protein and its amino acid sequence are disclosed in SEQ ID NO:19 and SEQ ID NO:20, respectively.

As another alternative, recombinant fusion proteins of the invention can comprise a heterologous polypeptide comprising a leucine zipper. Among known leucine zipper sequences are sequences that promote dimerization and sequences that promote trimerization. See e.g. Landschulz et al. (1988), Science 240: 1759–64. Leucine zippers comprise a repetitive heptad repeat, often with four or five leucine residues interspersed with other amino acids. Use and preparation of leucine zippers are well-known in the art.

Alternatively, a heterologous polypeptide forming part of a recombinant fusion protein can be one or more peptide linkers, connecting two or more BTL-II polypeptides. Generally, a peptide linker is a stretch of amino acids that serves to link plural identical, similar, or different polypeptides to form multimers and provides the flexibility or rigidity required for the desired function of the linked portions of the protein. Typically, a peptide linker is between about 1 and 30 amino acids in length. Examples of peptide linkers include, but are not limited to, -Gly-Gly-, GGGGS (SEQ ID NO:21), (GGGGS)n (SEQ ID NO:22), GKSSGSGSESKS (SEQ ID NO:23), GSTSGSGKSSEGKG (SEQ ID NO:24), GSTSGS-GKSSEGSGSTKG (SEQ ID NO:25), GSTSGSGKS-SEGKG (SEQ ID NO:26), GSTSGSGKPGSGEGSTKG (SEQ ID NO:27), or EGKSSGSGSESKEF (SEQ ID NO:28). Linking moieties are described, for example, in Huston, J. S., et al., Proc. Nat. Acad. Sci. 85: 5879–83 (1988), Whitlow, M., et al., Protein Engineering 6: 989–95 (1993), and Newton, D. L., et al., Biochemistry 35: 545–53 (1996). Other suitable peptide linkers are those described in U.S. Pat. Nos. 4,751,180 and 4,935,233.

Further, a recombinant fusion protein can comprise a BTL-II protein that lacks its normal signal sequence and has instead a heterologous signal sequence replacing it. The choice of a signal sequence depends on the type of host cells in which the recombinant protein is to be produced, and a heterologous signal sequence can replace the native signal sequence. Examples of signal sequences that are functional in mammalian host cells include the following: the signal sequence for interleukin-7 (IL-7) described in U.S. Pat. No. 4,965,195; the signal sequence for interleukin-2 receptor described in Cosman et al. ((1984), *Nature* 312: 768); the interleukin-4 receptor signal peptide described in EP Patent No. 0 367 566; the type I interleukin-1 receptor signal peptide described in U.S. Pat. No. 4,968,607; and the type II interleukin-1 receptor signal peptide described in EP Patent No. 0 460 846.

BTL-II Nucleic Acids

The invention encompasses isolated nucleic acids that encode the BTL-II proteins, fragments, or immunogenic fragments described above, including variants, fragments, recombinant fusion proteins, full-length proteins, soluble proteins, and secreted proteins. These nucleic acids are useful for, inter alia, producing recombinant proteins and detecting the presence of BTL-II nucleic acids in tissue samples, e.g. for diagnostic uses. Such nucleic acids can be genomic DNA or cDNA. The nucleic acid can comprise an uninterrupted open reading frame encoding a BTL-II protein of the invention. Nucleic acid molecules of the invention include DNA and RNA in both single-stranded and double-stranded form, as well as the corresponding complementary sequences. An "isolated nucleic acid" is a nucleic acid that has been separated from adjacent genetic sequences present in the genome of the organism from which the nucleic acid was isolated, in the case of nucleic acids isolated from naturally-occurring sources. In the case of nucleic acids synthesized chemically, such as oligonucleotides, or enzymatically from a template, such as polymerase chain reaction (PCR) products or cDNAs, it is understood that the nucleic acids resulting from such processes are isolated nucleic acids. An isolated nucleic acid molecule refers to a nucleic acid molecule in the form of a separate fragment or as a component of a larger nucleic acid construct.

Further, the invention encompasses fragments of a nucleic acid encoding a BTL-II protein that can serve (1) as probes for detecting BTL-II nucleic acids by a number of methods well known in the art, e.g. Southern and northern blotting, dot blotting, colony hybridizations, etc., (2) as polymerase chain reaction (PCR) primers to amplify BTL-II nucleic acids, or (3) as a means to regulate expression of BTL-II nucleic acids, e.g. through inhibition of expression with antisense nucleic acids (including peptide nucleic acids), ribozymes, triple helix-forming molecules, or interfering RNAs or DNAs that encode any of these RNAs. PCR primers can comprise, in addition to BTL-II nucleic acid sequences, other sequences such as restriction enzyme cleavage sites that facilitate the use of the amplified nucleic acid. PCR is described in the following references: Saiki et al. (1988), Science 239: 487–91; *PCR Technology*, Erlich, ed., Stockton Press, (1989). As explained below, PCR can be useful to detect overexpression of BTL-II mRNAs, and PCR primers can be taken from various parts of the gene and can also be selected to distinguish between different splice variants. Antisense RNAs (and DNAs encoding them), DNAs, or synthetic nucleotides and their use to regulate expression are well known in the art and are described in, e.g. Izant and Weintraub (1984), Cell 36 (4): 1007–15; Izant and Weintraub (1985), Science 229 (4711): 345–52; Harel-Bellan et al. (1988), J. Exp. Med. 168 (6): 2309–18; Sarin et al. (1988), Proc. Nat. Acad. Sci. USA 85 (20): 7448–51; Zon (1988), Pharm. Res. 5 (9): 539–49; Harel-Bellan et al. (1988), J. Immunol. 140 (7): 2431–35; Marcus-Sekura et al. (1987), Nucleic Acids Res. 15 (14): 5749–63; Gambari (2001), Curr. Pharm. Des. 7 (17): 1839–62; and Lemaitre et al. (1987), Proc. Natl. Acad. Sci. USA 84 (3): 648–52. Similarly, interfering RNAs (and DNAs encoding them) and their use to inhibit expression of selected genes are well known in the art and described in, e.g., Fjose et al. (2001), Biotechnol. Ann. Rev. 7: 31–57; Bosher and Labouesse (2000), Nature Cell Biol. 2: E31–E36. Further, ribozymes or DNAzymes can be targeted to cleave specific RNAs and thus used to inhibit gene expression as described in, e.g., Lewin and Hauswirth (2001), Trends Mol. Med. 7 (5): 221–28; Menke and Hobom (1997), Mol. Biotechnol. 8 (1): 17–33; Norris et al. (2000), Adv. Exp. Med. Biol. 465: 293–301; Sioud (2001), Curr. Mol. Med. 1 (5): 575–88; and Santiago and Khachigian (2001), J. Mol. Med. 79 (12): 695–706. Nucleic acids that can regulate BTL-II expression can find use in in vivo or in vitro studies of BTL-II function or as therapeutics, optionally as gene therapy agents.

The present invention also includes nucleic acids that hybridize under moderately stringent conditions, and more preferably highly stringent conditions, to nucleic acids encoding the BTL-II proteins described herein. Such nucleic acids include SEQ ID NO:3, SEQ ID NO:5, SEQ ID NO:7, SEQ ID NO:9, SEQ ID NO:11, SEQ ID NO:13, SEQ ID NO:15, or SEQ ID NO:17. Preferably such nucleic acids encode proteins that can bind to a receptor on the surface of T cells and/or can inhibit T cell proliferation and/or cytokine production. Hybridization techniques are well known in the art and are described by Sambrook, J., E. F. Fritsch, and T. Maniatis (*Molecular Cloning: A Laboratory Manual*, Cold Spring Harbor Laboratory Press, Cold Spring Harbor, N.Y., chapters 9 and 11, (1989)) and *Current Protocols in Molecular Biology* (F. M. Ausubel et al., eds., John Wiley & Sons, Inc., sections 2.10 and 6.3–6.4 (1995)). Moderately stringent conditions include hybridization in about 50% formamide, 6×SSC at a temperature from about 42 to 55° C. and washing at about 60° C. in 0.5×SSC, 0.1% SDS. Highly stringent conditions are defined as hybridization conditions as above, but with washing at approximately 68° C. in 0.2×SSC, 0.1% SDS. SSPE (1×SSPE is 0.15 M NaCl, 10 mM $NaH_2PO_4$, and 1.26 mM EDTA, pH 7.4) can be substituted for SSC (1×SSC is 0.15 M NaCi and 15 mM sodium citrate) in the hybridization and wash buffers; washes, preferably at least two, are performed for 15 minutes after hybridization is complete.

It should be understood that the wash temperature and wash salt concentration can be adjusted as necessary to achieve a desired degree of stringency by applying the basic principles that govern hybridization reactions and duplex stability, as known to those skilled in the art and described further below (see e.g., Sambrook et al., supra). When nucleic acids of known sequence are hybridized, the hybrid length can be determined by aligning the sequences of the nucleic acids and identifying the region or regions of optimal sequence complementarity. The hybridization temperature for hybrids anticipated to be less than 50 base pairs in length should be 5 to 10° C. less than the melting temperature (Tm) of the hybrid, where Tm is determined according to the following equations. For hybrids less than 18 base pairs in length, Tm (degrees C)=2 (# of A+T bases)+4 (# of G+C bases). For hybrids above 18 base pairs in length, Tm (degrees C)=81.5+16.6 ($\log_{10}[Na^+]$)+0.41 (% G+C)−(600/N), where N is the number of bases in the hybrid, and [$Na^+$] is the concentration of sodium ions in the hybridization buffer ([$Na^+$] for 1×SSC=0.165 M). Each such hybridizing nucleic acid has a length that is at least 15 nucleotides (or at least 18 nucleotides, or at least 20, or at least 25, or at least 30, or at least 40, or at least 50, or at least 100. Sambrook et al., supra.

BTL-II nucleic acids include nucleic acids comprising the following polynucleotides: (1) all or or a fragment of SEQ ID NO:3, SEQ ID NO:5, SEQ ID NO:7, SEQ ID NO:9, SEQ ID NO:11, SEQ ID NO:13, SEQ ID NO:15, or SEQ ID NO:17, wherein the fragment encodes a BTL-II protein that can bind to a receptor expressed on the surface of a T cell and/or inhibit proliferation and/or cytokine production of T cells; (2) sequences at least 80%, 85%, 90%, 95%, 97%, 98%, 99%, 99.5%, or 99.7% identical to SEQ ID NO:3, SEQ ID NO:5, SEQ ID NO:7, SEQ ID NO:9, SEQ ID NO:11, SEQ ID NO:13, SEQ ID NO:15, or SEQ ID NO:17 that are at least 100, 125, 150, 175, 200, 225, 250, 300, 400, 500, 600, 800, 1000. 1200, 1400, or 1600 nucleotides long and encode a BTL-II protein that can bind to a receptor expressed on the surface of T cells and/or inhibit proliferation and/or cytokine production of T cells; (3) fragments of SEQ ID NO:3, SEQ ID NO:5, SEQ ID NO:7, SEQ ID NO:9, SEQ ID NO:11, SEQ ID NO:13, SEQ ID NO:15, or SEQ ID NO:17 or substantially similar sequences that are useful for detecting or amplifying nucleic acids encoding the BTL-II proteins of the invention or for regulating the expression of BTL-II mRNAs and/or proteins; (4) nucleic acids comprising a polynucleotide that is at least 80%, 85%, 90%, 95%, 97%, 98%, 99%, 99.5%, or 99.7% identical to a polynucleotide consisting of nucleotides 30 to 130 of SEQ ID NO:7 or SEQ ID NO:11 or to nucleotide 377–477 of SEQ ID NO:9, SEQ ID NO:13, SEQ ID NO:15, or SEQ ID NO:17, wherein the region of identity is at least 60, 70, 80, 90, or 100 nucleotides long and the protein encoded by the nucleic acid can inhibit proliferation and/or cytokine production of T cells; and (5) nucleic acids that comprise at least 1, 2, 3, 4, 6, 8, 10, 15, 20, 25, 30, 35, 40, 50, or 75 alteration(s) relative to SEQ ID NO:3, SEQ ID NO:5, SEQ ID NO:7, SEQ ID NO:9, SEQ ID NO:11, SEQ ID NO:13, SEQ ID NO:15, or SEQ ID NO:17, wherein an alteration can be an insertion, deletion or substitution of a single nucleotide.

Antibodies that Bind Specifically to BTL-II Polypeptides

Antibodies that bind specifically to the BTL-II proteins of the invention, including variants, fragments, and recombinant fusion proteins, are encompassed by the invention. As used herein, specific binding of an epitope on a BTL-II protein by another protein (such as an antibody) means that the specifically-bound protein can be displaced from the molecule of BTL-II protein to which it is bound by another protein comprising the same epitope but not by another protein which does not comprise this epitope. Numerous competitive binding assays are known in the art. Epitopes may comprise only contiguous amino acids, but also may comprise non-contiguous amino acids that are brought into proximity by the tertiary folding of a BTL-II protein. Epitopes can be identified by methods known in the art. See e.g. Leinonen et al. (2002), Clin. Chem. 48 (12): 2208–16; Kroger et al. (2002), Biosens. Bioelectron. 17 (11–12): 937–44; Zhu et al. (2001), Biochem. Biophys. Res. Commun. 282 (4): 921–27. The invention also encompasses epitopes of the BTL-II proteins described herein that are useful for generating antibodies, which are referred to herein as immunogenic fragments. Immunogenic fragments are preferably at least 10 amino acids long and preferably comprise contiguous amino acids from SEQ ID NO:4, SEQ ID NO:6, SEQ ID NO:8, SEQ ID NO:10, SEQ ID NO:12, SEQ ID NO:14, SEQ ID NO:16, or SEQ ID NO:18. Such epitopes can span regions of BTL-II proteins encoded by splice junctions, which may have the advantage of specific binding to proteins encoded by specific splice variants.

Antibodies can be polyclonal or monoclonal antibodies and can be produced by methods well-known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988); Kohler and Milstein (1980) Proc. Natl. Acad. Sci., USA, 77: 2197; Kozbor et al. (1984), J. Immunol. 133: 3001–3005 (describing the human B-cell hybridoma technique); Cole et al., *Monoclonal Antibodies And Cancer Therapy*, Alan R. Liss, Inc., pp. 77–96 (1985)(which describes EBV-hybridoma technique);. Kuby, *Immunology*, Second Edition, p. 162–64, W.H. Freeman and Co., New York (1994). Hybridoma cell lines that produce monoclonal antibodies specific for the BTL-II proteins of the invention are also contemplated herein. Such hybridomas can be produced and identified by conventional techniques. The hybridoma producing-the mAb of this invention can be cultivated in vitro or in vivo. Further, anti-BTL-II antibodies of the invention can be produced in other cultured cells, including, for example, Chinese hamster ovary (CHO), HeLa, VERO, BHK, Cos, MDCK, 293, 3T3, myeloma (e.g. NSO, NSI), or W138 cells, yeast cells, insect cells, and bacterial cells, including, for example, *Eschericha coli*. Such antibodies can be produced by introducing nucleic acids encoding the antibodies plus nucleic acids to enable expression of these nucleic acids into desired host cells. The antibodies can then be produced by culturing the cells into which these nucleic acids have been introduced. Monoclonal antibodies can be of any immunoglobulin class including IgG, IgM, IgE, IgA, IgD and any subclass thereof.

Alternatively, antibodies can be single chain antibodies comprising a heavy and a light chain variable region-like domain and, optionally, also one or more constant region-like domain (U.S. Pat. No. 4,946,778; Bird et al. (1988), Science 242: 423–26; Huston et al. (1988), Proc. Natl. Acad. Sci. USA 85: 5879–83), dimeric or multivalent antibodies (see e.g. Lantto et al. (2002), J. Gen. Virol. 83: 2001–05; Hudson and Souriau (2001), Expert Opin. Biol. Ther. 1 (5): 845–55), tetrameric antibodies (see e.g. Janeway et al., Immunobiology: The Immune System in Health and Disease, Fifth Edition, Part II, Ch. 3, Garland Publishing (2001)), chimeric antibodies (Hudson and Souriau, supra; Boulianne et al. (1984), Nature 312:643–46; Morrison et al (1984), Proc. Natl. Acad. Sci. USA 81: 6851–55; Takeda et al. (1985), Nature 314: 452–54; Neuberger et al. (1985), Nature 314: 268–70), fully human antibodies produced in a different transgenic mammal (described in e.g., U.S. Pat. No. 6,150,584) or by in vitro selection (U.S. patent application No. 2002/0058033) or humanized antibodies (Morrison et al., supra; Takeda et al., supra; Boulianne et al., supra). Further, antibodies can be "matured" by in vitro selection schemes to yield an antibody with altered properties such as, for example, a higher affinity for the epitope to which it binds. See e.g. Jackson et al. (1995), J. Immunol. 154 (7): 3310–19; Pini and Bracci (2000), Curr. Protein Pept. Sci. 1 (2): 155–69; Ellmark et al. (2002), Mol. Immunol. 39 (5–6): 349; O'Connell et al. (2002), J. Mol. Biol. 321 (1): 49–56; Huls et al. (2001), Cancer Immunol. Immunother. 50: 163–71; Hudson and Souriau, supra; Adams and Schier (1999), J. Immunol. Methods 231 (1–2): 249–60; Schmitz et al. (2000), Placenta 21 Suppl. A: S106–12. Alternatively, fragments of an antibodies such as, for example, Fab fragments, F(ab')$_2$ fragments, or single chain Fv fragments (scFv's) that can bind specifically to a BTL-II protein of the invention are also encompassed by what is meant herein as an anti-BTL-II antibody. See Kuby, supra, pp.109–112 and Janeway et al., supra, for discussion of Fab and Fv fragments. The invention also encompasses anti-idiotypic antibodies that bind specifically to antibodies that bind specifically to BTL-II proteins and that mimic the effects of BTL-II proteins. Such anti-idiotypic antibodies find the same uses as BTL-II proteins. Methods for generating anti-idiotypic antibodies are well known in the art. See e.g. Kuby et al., supra, at 371–72. Various kinds of recombinant and non-recombinant bispecific antibodies that can bind specifically to a BTL-II protein of the invention and another epitope are also contemplated. Various kinds of bispecific antibodies and methods for making them are described in e.g. U.S. Pat. Nos. 4,474,893, 6,060,285, and 6,106,833.

The anti-BTL-II antibodies may be antagonistic antibodies that block a biological function of BTL-II, such as the binding of BTL-II to its receptor, or agonistic antibodies that promote a biological function of BTL-II or mimic the function of BTL-II. Agonistic antibodies can include agonistic anti-idiotypic antibodies that mimic the function of BTL-II protein. Assays for BTL-II function are described herein. Anti-BTL-II antibodies that block a biological function of BTL-II as determined in such assays are antagonistic antibodies as meant herein. Antagonistic antibodies may, for example, block the binding of BTL-II to its receptor. Anti-BTL-II antibodies that, when added to such assays, promote or enhance a biological function of BTL-II are agonistic antibodies as meant herein. An antagonistic anti-BTL-II antibody can be used, for example, as an adjuvant to enhance a mucosal immune response. Further, an agonistic antibody against a BTL-II receptor can be used to depress a mucosal immune response to treat, for example, a disease that is characterized by inappropriate inflammation of the gut, such as Crohn's disease or inflammatory bowel disease.

The antibodies of the invention can also be used in assays to detect the presence of the BTL-II proteins of the invention, either in vitro or in vivo. The antibodies also can be employed in purifying BTL-II proteins of the invention by immunoaffinity chromatography.

The invention encompasses nucleic acids encoding the antibodies of the invention and methods for producing the antibodies by introducing such nucleic acids into cells and culturing the cells containing the nucleic acids.

Agonists and Antagonists of BTL-II Polypeptides

The invention comprises agonists and antagonists of BTL-II and methods for screening for and using agonists and antagonists. Assays for BTL-II biological activity are described herein such as, for example, cell proliferation assays, cytokine secretion assays, binding assays, and genetic assays involving the over- or under-expression of BTL-II protein in vivo or in vitro or a complete absence of BTL-II expression in vivo or in vitro. Candidate molecules can be added to such assays to determine their effects on the biological activity of BTL-II proteins. BTL-II antagonists can, for example, block the interaction of BTL-II with its receptor, which is preferably expressed on B cell or T cells. Antagonists include antagonistic antibodies, and agonists include agonistic antibodies. In addition, other antibody-related molecules that can bind specifically to the BTL-II proteins of the invention, such as affibodies (Rönnmark et al. (2002), J. Immunol. Methods 261 (1–2): 199–211) and the biologically active peptides described in WO 00/24782 that can bind specifically to the BTL-II proteins of the invention and inhibit the biological activity of BTL-II proteins are encompassed by the invention. Further, BTL-II antagonists include the nucleic acids described above that are useful for modulating expression of BTL-II protein and/or mRNA, such as, for example, interfering RNAs (or DNAs that encode them) or antisense RNAs or DNAs.

Antagonists further include proteins that comprise amino acid sequences selected in vitro to bind to BTL-II or its receptor and that can, optionally, interfere with the interaction of BTL-II and its receptor. Alternatively, such proteins can be BTL-II agonists that promote or mimic the biological function of BTL-II. Proteins that bind to BTL-II or its receptor can be screened for their ability to interfere with the interaction of BTL-II with its receptor, or, alternatively, a selection can be designed to obtain such proteins directly.

Proteins may be selected by a number of methods such as, for example, phage display or display of the surface of a bacterium. See e.g. Parmley and Smith (1989), Adv. Exp. Med. Biol. 251: 215–218; Luzzago et al. (1995), Biotechnol. Annu. Rev. 1: 149–83; Lu et al. (1995), Biotechnology (NY) 13 (4): 366–372. In these methods, each member of a library of binding domains can be displayed on individual phage particles or bacterial cells, and bacteria or phage that bind to a protein of interest under chosen conditions can be selected. Nucleic acids encoding the selected binding domains can be obtained by growing the selected phage or bacteria and isolating nucleic acids from them.

Alternatively, a protein can be selected entirely in vitro. For example, each individual polypeptide in a library of potential binding domains can be attached to nucleic acids encoding it, and those that bind to the protein of interest under chosen conditions can be selected. Since the polypeptides are attached to nucleic acids encoding them, subsequent operations, such as amplifying, cloning, or sequencing nucleic acids encoding effective binding domains are facilitated. Various schemes for such selections are known in the art, including antibody-ribosome-mRNA particles, ribosome display, covalent RNA-peptide fusions, or covalent DNA-RNA-peptide fusions. He and Taussig (1997), Nucleic Acids. Res. 25 (24): 5132–5134; Hanes and Pluckthun (1997), Proc. Natl. Acad. Sci. 94: 4937–4942; Roberts and Szostak (1997), Proc. Natl. Acad. Sci. 94: 12297–12302; Lohse and Wright (2001), Curr. Opin. Drug Discov. Devel. 4 (2): 198–204; Kurz et al. (2000), Nucleic Acids Res. 28 (18): E83; Liu et al. (2000), Methods Enzymol. 318: 268–93; Nemoto et al. (1997), FEBS Lett. 414 (2): 405–08; U.S. Pat. No. 6,261,804; WO0032823; and WO0034784. Such proteins can be selected to be antagonists or agonists.

Assays for the Biological Activity of BTL-II Proteins

Various assays can be used to detect the biological activity of a BTL-II protein and to identify binding partners of BTL-II. BTL-II proteins, receptor(s) of BTL-II, and agonists and/or antagonists of either can be used in such assays.

Assays to Identify Binding Partners

A binding partner for BTL-II protein can be identified by first determining what type of cells a soluble BTL-II protein can bind to. Since the known receptors for members of the B7 subfamily of butyrophilin-like proteins are all expressed on T cells, either constitutively (CD28) or after activation (CTLA-4, ICOS, PD-1), T cells can be tested to determine whether BTL-II can bind to them. Because of the expression pattern of BTL-II, T cells isolated from normal and inflamed gut can be included in such tests. In addition, various subsets of T cells, including memory T cells, naive T cells, $\alpha\beta$ T cells, $\gamma\delta$ T cells, and T cells in various activation states, can be tested.

Such experiments can be conducted using methods well known in the art. For example, a BTL-II recombinant fusion protein comprising the extracellular domain of murine BTL-II plus an Fc region of an antibody can be used to bind to the cells being tested. A fluorescently-labeled antibody that can bind to the Fc region in the recombinant fusion protein can be added. After washing, the cells can be analyzed using a fluorescence activated cell sorting (FACS) device to determine whether BTL-II can bind to the cells. One such assay is described by Chapoval et al. )(2001), Nature Immunol. 2 (3): 269–74). Other methods known in the art can also be suitable to determine whether BTL-II binds to specific cell populations.

Further, known receptors of B7 subfamily members will be tested to determine whether BTL-II binds to any of these proteins. Recombinant fusion proteins comprising an extra-cellular domain of a receptor of a B7 sub-family member (such as, for example, CTLA-4, a receptor for B7-1 and B7-2) and an Fc region of an antibody can be made by methods similar to those used to make such BTL-II fusion proteins. Cells can be transfected with full length forms of BTL-II nucleic acids encoding BTL-II proteins including transmembrane and cytoplasmic domains that are expressed on the cell surface. The receptor:Fc fusion protein to be tested can be added to such cells along with a fluorescently-labeled antibody that can bind to the Fc region. After washing, the cells can be analyzed by FACS to determine whether the receptor:Fc fusion protein binds to the BTL-II protein expressed on the transfected cells. The reverse experiment can also done where soluble BTL-II:Fc fusion protein is used and the full length receptor protein is introduced and expressed via transfection. Such experiments can reveal binding interactions between BTL-II proteins and known receptors of other B7 subfamily members.

If BTL-II binds to at least one variety of T cells but does not bind to a known receptor, a variety of expression cloning or protein purification methods known in the art can be used to identify the receptor that BTL-II binds to. As an example, a radioactive slide binding cDNA expression cloning method can be used. Briefly, a cell source with the greatest binding to soluble BTL-II is identified, mRNA is isolated, and a cDNA library is built in a mammalian expression vector. Mammalian cells are transfected with pools of cDNAs on slides, and after an appropriate incubation to allow expression, soluble BTL-II:Fc fusion protein is bound to the cells. Specific binding to receptor bearing cells is detected by the following series of steps: binding of a radioactive anti-Fc reagent to the bound BTL-II:Fc protein; application of film emulsion to the slides; incubation to allow exposure; film development to deposit silver grains; and detection of the grains by microscope. The receptor-expressing clone is then isolated from the pool by sub-dividing the pool and iterative slide binding assays to identify the single receptor clone. Such methods are described in McMahon et al. (1991), EMBO J. 10: 2821–32.

When binding to cells is achieved, a variety of means, either through animal immunization or phage display technology, can be used to isolate antibodies that bind BTL-II and disrupt its binding to cells. Such antibodies can be used to antagonize the activity of endogenous BTL-II and therefore can be used in assays to determine the effects of lowered effective amounts of BTL-II on immune responses and in disease models, such as the inflammatory bowel disease models, for example, those described by Cooper et al. ((1993), Lab. Invest. 69 (2): 238–49) and Tokoi et al. ((1996), J. Gastroenterol. 31 (2): 182–88).

Assays to Determine BTL-II Function

B7 subfamily proteins have been shown to have activity in T cell "co-stimulatory" assays that involve activating T cells through their T cell receptors with varying doses of "antigen." The activity of the B7 subfamily proteins is most evident at "sub-optimal" T cell receptor stimulation. See e.g. Latchman et al. (2001), Nature Immunol. 2 (3): 261–68. A "surrogate antigen," such as tissue culture dish bound anti-CD3ε antibody or antigens presented by the MHC molecules on irradiated antigen presenting cells, can be used. A soluble BTL-II protein can be added to determine its effect on the T cells' response to the "antigen." Various parameters can be measured to determine whether the T cells are being stimulated or suppressed. Cellular proliferation, cell surface receptor expression, and levels of expression of immuno-modulatory molecules (such as, for example, interferon $\gamma$ and/or IL-2) at the protein and/or MRNA level can be measured. Such methods are used and described in e.g., Fitch et al. *in T Cell Subsets in Infectious and Autoimmune Diseases*, John Wiley and Sons, pp. 68–85 (1995); Freeman et al. (2000), J. Exp. Med. 192 (7): 1027–34; Swallow et al. (1999), Immunity 11:423–32; Hutloff et al. (1999), Nature 397: 263–66; Yoshinaga et al. (1999), Nature 402: 827–32; Latchman et al., supra. Given the expression pattern of BTL-II, such assays can include T cells derived from mucosal tissues or the lymph nodes that drain such tissues. In addition, naive and memory T cells, $CD4^+$ and $CD8^+$ T cells, and T cells expressing T cell receptors other than $\alpha\beta$ T cell receptors can be examined. From such experiments can reveal whether BTL-II can alter responses of a number of distinct kinds of T cells. Such experiments are described below and show that a soluble version of BTL-II can inhibit cell proliferation and suppress production of cytokines, including interferon gamma (IFN$\gamma$), interleukin 2 (IL2), and interleukin 5 (IL5). Examples 6–10; FIGS. 12–17.

Variations of this kind of experiment include examining the effect of including soluble forms of BTL-II proteins on the co-stimulatory response found with other soluble B7 subfamily proteins or various TNF family members that can be co-stimulatory. This will help to define whether BTL-II can alter co-stimulation seen with other molecules. Further variations can include use of non-irradiated antigen presentation cells of various sorts. This will help define the effects of addition of a soluble BTL-II protein on the function of antigen presenting cells. In still another variation, antibodies that block BTL-II binding to cells (see above) can also be introduced in such costimulation experiments to determine the effects of preventing binding.

In another kind of experiment, antigen presenting cells (such as, for example, dendritic cells or B cells from Peyer's patches or intestinal epithelial cells (IECs)) that express BTL-II can be combined with T cells (such as the various kinds listed above), and one or more of the parameters listed above can be measured. The results obtained with these cells can be compared to results obtained when interfering RNAs, or DNAs encoding them, designed to lower BTL-II expression are introduced into the antigen presenting cells.

T regulatory cells act to suppress autoimmune responses and help to do so, in part, by inducing differentiation or enhancing regulatory function of T regulatory (T reg) cells in inflammatory bowel disease model systems. T reg cells include, for example, Tr1 cells (Cong et al. (2002), J.

Immunol. 169 (11): 6112–19; Groux et al. (1997), Nature 389: 737–42), Th3 cells, CD4$^+$Cd25$^+$ T reg cells (see e.g. Maloy and Powrie (2001), Nature Immunology 2 (9): 816–22), CD4$^+$Rb$^{lo}$CD25$^+$ T reg cells, and CD8$^+$ T reg cells (Allez et al. (2002), Gastroenterology 123: 1516–26), among others. Thus, assessing the effects of BTL-II upon T regulatory cell proliferation and function may be necessary to determine the precise role of BTL-II in vivo. For example, antigen specific proliferation of T cells and/or cytokine production by T cells in the presence of Tr1 cells can be measured. Such assays are described in Cong et al., supra. Soluble forms of BTL-II, blocking antibodies, or inhibition of BTL-II expression using interfering RNAs can be used to determine whether BTL-II plays a role in T regulatory cell or Tr1 cell proliferation, maintenance, or ability to suppress antigen activation of other T cells.

One T cell subset, Th3 cells, produce transforming growth factor β (TGF β) and have been implicated in oral tolerance to mucosal antigens. See e.g. Fukaura et al. (1996), J. Clin. Invest. 98 (1): 70–77; Inobe et al. (1998), Eur. J. Immunol. 28: 2780–90. Such cells can be generated from native T cells by extensive culture with antigen in the presence of TGF β. Soluble BTL-II proteins or blocking antibodies can be used to ask whether BTL-II can alter the proliferation or function of these cells by methods similar to those described above.

The effects of administering soluble BTL-II proteins or antagonistic antibodies in model T cell systems using simple, well-defined antigens, such as, for example, ovalbumin, or complex antigens, including bacteria or viruses, will be ascertained. T cells responses to such antigens (including proliferation and/or production of molecules such as interferon γ or IL-2) can be measured in the presence and absence of BTL-II proteins or antibodies.

Similarly effects in animal systems can be tested. Early focus will be on systems particularly relevant to mucosal immune response. This includes model systems in which antigen is fed to animals (see e.g. Yamashiro et al. (1994), Acta Paediatr. Jpn. 36: 550–56; Jain et al. (1996), Vaccine 14 (13):1291–97; Chen et al. (2002), Immunology 105: 171–80), inflammatory bowel disease systems such as in the dextran sulfate sodium-induced inflammatory bowel disease model (Cooper et al. (1993), Lab. Invest. 69 (2): 238–49; Tokoi et al. (1996), J. Gastroenterol. 31 (2): 182–88), the CD45RB$^{hi}$/CD4$^+$ T cell-induced wasting disease model (Morrissey et al. (1993), J. Exp. Med. 178: 237–44), and/or model asthma systems in which antigen is fed or instilled into the airways to provoke an immune response such as the murine ovalalbumin-induced asthma model (Brusselle et al. (1994), Clin. Exp. Allergy 24 (1): 73–80). In particular, the magnitude of the humoral or cell mediated response will be measured, and the type of immunomodulatory cytokines produced will be measured. Such experiments can reveal whether increased or decreased BTL-II can be of benefit in dampening responses to antigens, including autoantigens, or increasing response to alloantigens. Effects of BTL-II proteins or anti-BTL-II antibodies can also be ascertained in other models of inflammatory diseases.

Assays for T-cell or thymocyte proliferation include without limitation those described in: *Current Protocols in Immunology*, Coligan et al. eds, Greene Publishing Associates and Wiley-Interscience (pp. 3.1–3.19: In vitro assays for mouse lymphocyte function; Chapter 7: Immunologic studies in humans); Takai et al. (1986), J. Immunol. 137: 3494–3500; Bertagnolli et al. (1990), J. Immunol. 145: 1706–1712; Bertagnolli, et al. (1992), J. Immunol. 149: 3778–3783; Bowman et al. (1994), J. Immunol. 152: 1756–1761.

Assays for cytokine production and/or proliferation of spleen cells, lymph node cells or thymocytes include, without limitation, those described in: Kruisbeek and Shevach (1994), Polyclonal T cell stimulation, in *Current Protocols in Immunology*, Coligan et al. eds. Vol 1 pp. 3.12.1–3.12.14, John Wiley and Sons, Toronto (1991); and Schreiber, (1994), Measurement of mouse and human interferon gamma in *Current Protocols in Immunology*, Coligan et al. eds. Vol 1 pp. 6.8.1–6.8.8, John Wiley and Sons, Toronto (1991).

Assays for proliferation and differentiation of hematopoietic and lymphopoietic cells include, without limitation, those described in: Bottomly et al., 1991, Measurement of human and murine interleukin 2 and interleukin 4, in *Current Protocols in Immunology*, Coligan et al. eds. Vol 1 pp. 6.3.1–6.3.12, John Wiley and Sons, Toronto (1991); deVries et al. (1991), J. Exp. Med. 173: 1205–1211; Moreau et al. (1988), Nature 336:690–692; Greenberger et al. (1983), Proc Natl Acad Sci.USA 80: 2931–2938; Nordan, Measurement of mouse and human interleukin 6, in *Current Protocols in Immunology*, Coligan et al. eds. Vol 1 pp. 6.6.1–6.6.5, John Wiley and Sons, Toronto (1991); Smith et al., (1986), Proc Natl Acad Sci USA 83: 1857–1861; Bennett et al., 1991, Measurement of human interleukin 11, in *Current Protocols in Immunology* Coligan et al. eds. Vol 1 pp. 6.15.1 John Wiley and Sons, Toronto (1991); Ciarletta et al., Measurement of mouse and human Interleukin 9, in Current Protocols in Immunology Coligan et al. eds. Vol 1 pp. 6.13.1, John Wiley and Sons, Toronto (1991).

Assays for T-cell clone responses to antigens (which will identify, among others, polypeptides that affect APC-T cell interactions as well as direct T-cell effects by measuring proliferation and cytokine production) include, without limitation, those described in: *Current Protocols in Immunology*, Coligan et al. eds, Greene Publishing Associates and Wiley-Interscience (Chapter 3: In vitro assays for mouse lymphocyte function; Chapter 6: Cytokines and their cellular receptors; Chapter 7: Immunologic studies in humans)(1991); Weinberger et al. (1980), Proc Natl Acad Sci USA 77: 6091–6095; Takai et al. (1986), J. Immunol. 137:3494–3500; Takai et al. (1988), J. Immunol. 140: 508–512.

Assays for thymocyte or splenocyte cytotoxicity include, without limitation, those described in: *Current Protocols in Immunology*, Coligan et al. eds, Greene Publishing Associates and Wiley-Interscience (Chapter 3, In Vitro assays for Mouse Lymphocyte Function 3.1–3.19; Chapter 7, Immunologic studies in Humans)(1991); Herrmann and Mescher (1981), Proc. Natl. Acad. Sci. USA 78: 2488–2492; Herrmann et al. (1982), J. Immunol. 128: 1968–1974; Handa et al. (1985), J. Immunol. 135:1564–1572; Takai et al. (1986), J. Immunol. 137: 3494–3500; Takai et al. (1988), J. Immunol. 140:508–512,; Brown et al. (1994), J. Immunol. 153: 3079–3092.

Assays for immunoglobulin responses and isotype switching by B cells (which will identify, among others, polypeptides that modulate T-cell dependent antibody responses and that affect Th1/Th2 profiles) include, without limitation, those described in: Maliszewski (1990), J. Immunol 144: 3028–3033; and Mond and Brunswick, Assays for B cell function: in vitro antibody production, in *Current Protocols in Immunology* Coligan et al. eds. Vol 1 pp. 3.8.1–3.8.16, John Wiley and Sons, Toronto (1994).

Mixed lymphocyte reaction (MLR) assays (which will identify, among others, polypeptides that generate predominantly Th1 and CTL responses) include, without limitation, those described in: *Current Protocols in Immunology*, Coligan et al. eds, Greene Publishing Associates and Wiley- Interscience (Chapter 3, In Vitro assays for Mouse Lymphocyte Function 3.1–3.19; Chapter 7, Immunologic studies in Humans); Takai et al. (1986); J. Immunol. 137:3494–3500; Takai et al. (1988), J. Immunol. 140: 508–512; Bertagnolli et al. (1992), J. Immunol. 149: 3778–3783.

Dendritic cell-dependent assays (which will identify, among others, polypeptides expressed by dendritic cells that activate naive T-cells) include, without limitation, those described in: Guery and Adorini (1995), J. Immunol 154: 536–544; Inaba et al. (1991), J Exp Med 173: 549–559; Macatonia et al. (1995), J Immunol 154: 5071–5079; Porgador and Gilboa (1995), J Exp Med 182: 255–260; Nair et al. (1993), J. Virology 67:4062–4069; Huang et al. (1994), Science 264:961–965; Macatonia et al. (1989), J Exp Med 169:1255–1264; Bhardwaj et al. (1994), J. Clin. Invest. 94:797–807; and Inaba et al. (1990), J. Exp. Med. 172: 631–640.

Assays for polypeptides that influence early steps of T-cell commitment and development include, without limitation, those described in: Antica et al. (1994), Blood 84: 111–117; Fine et al. (1994), Cell Immunol 155: 111–122; Galy et al. (1995), Blood 85: 2770–2778; Toki et al. (1991), Proc Natl Acad Sci. USA 88: 7548–7551.

Assays for receptor-ligand activity include without limitation those described in: *Current Protocols in Immunology* Coligan et al. eds, Greene Publishing Associates and Wiley-Interscience (Chapter 7.28, Measurement of cellular adhesion under static conditions 7.28.1–7.28.22); Takai et al. (1987), Proc. Natl. Acad. Sci. USA 84: 6864–6868; Bierer et al. (1988), J. Exp. Med. 168:1145–1156; Rosenstein et al. (1989), J. Exp. Med. 169: 149–160; Stoltenborg et al. (1994), J. Immunol. Methods 175: 59–68; Stitt et al. (1995), Cell 80: 661–670.

Genetic Assay For Function Utilizing Transgenic Animals

Transgenic animals, preferably mice, that have multiple copies of the gene(s) corresponding to the BTL-II nucleic acids disclosed herein, preferably produced by transformation of cells with genetic constructs that are stably maintained within the transformed cells and their progeny, are provided. Transgenic animals that have modified genetic control regions that increase or reduce gene expression levels, or that change temporal or spatial patterns of gene expression, are also provided (see European Patent No. 0 649 464 B1). In addition, organisms are provided in which the BTL-II gene has been partially or completely inactivated, through insertion of extraneous sequences into the corresponding gene or through deletion of all or part of the corresponding gene. Partial or complete gene inactivation can be accomplished through insertion, preferably followed by imprecise excision, of transposable elements (Plasterk (1992), Bioessays 14 (9): 629–633; Zwaal et al. (1993), Proc. Natl. Acad. Sci. USA 90 (16): 7431–7435; Clark et al., (1994), Proc. Natl. Acad. Sci. USA 91 (2): 719–722), or through homologous recombination, preferably detected by positive/negative genetic selection strategies (Mansour et al. (1988), Nature 336: 348–352; U.S. Pat. Nos. 5,464,764; 5,487,992; 5,627,059; 5,631,153; 5,614,396; 5,616,491; and 5,679,523). As an alternative, expression of the BTL-II gene can be inhibited in a transgenic or non-transgenic animal by introduction of an interfering RNA, antisense RNA, or a ribozyme, which may be encoded by DNA introduced into a transgenic animal. The phenotypes of such organisms can elucidate the in vivo function(s) of the BTL-II gene. For example, an increased propensity (compared to wild type animals) in a transgenic animal that does not express BTL-II protein to exhibit symptoms of inflammatory bowel disease in response to feeding of dextran sulfate sodium can indicate that BTL-II normally dampens inflammation in the gut. Alternatively, transgenic animals can overexpress BTL-II. Phenotypes of such transgenic animals can also give clues as to the in vivo function of BTL-II proteins.

Uses of the Proteins, Antibodies, Antagonists, and Agonists of the Invention

The mucosal immune system operates within a set of specialized anatomical structures, the mucus membranes, and the immune response it generates has properties that distinguish it from an immune response generated in other anatomical compartments of the body. The mucus membranes are just one of several distinct anatomical compartments, also including the peripheral lymph nodes and spleen, the body cavities, i.e. the peritoneum and the pleura, and the skin, in which the immune system is active. Mucosal surfaces are found in the lungs, the gut, the eyes, the nose, the mouth, the throat, the uterus, and the vagina. A mucosal surface is a thin sheet or layer of pliable tissue serving as the covering or envelope of a bodily structure, such as the lining of a body cavity, a partition or septum, or a connection between two structures. Since mucosal surfaces are the route of entry for the vast majority of infectious agents, an adjuvant that can promote a mucosal immune response is particularly desirable. Janeway et al., Immunobiology: The Immune System in Health and Disease, 5$^{th}$ Edition, Part IV, Ch. 10, Garland Publishing, New York and London (2001). Infectious diseases that typically enter through mucosal surfaces, such as, for example, *Neisseria gonorrhoeae*, often generate only a weak mucosal immune response. Russell et al. (1999), 42 (1): 58–63.

The gut is unique in several ways. Lining the gut are a number of specialized forms of lymphoid tissue collectively known as gut-associated lymphoid tissue (GALT) including: tonsils and adenoids, which together form Waldyer's ring at the back of the mouth; Peyer's patches in the small intestine; the appendix; and solitary lymphoid follicles in the large intestine and rectum. Activation of a lymphocyte by an encounter with a foreign antigen in the gut can lead to the spread of an adaptive immune response to the antigen throughout the mucosal immune system. The activated lymphocyte can enter the lymphatic system and, from there, the bloodstream. The bloodstream can deliver activated lymphocytes to mucosal sites throughout the body, which can be recognized by the lymphocytes by means of molecules such as the mucosal adressin MAdCAM-1, which is expressed in mucosal tissue. Janeway et al., supra. The dominant antibody type produced by the gut is IgA, which, upon expression, is found primarily in the mucus layer overlying the gut epithelium. In addition, a number of distinct kinds of T cells are found in the gut. Janeway et al., supra.

Introduction of a foreign antigen into the gut usually leads to immunological tolerance but may lead to a specific immune response. The gut normally receives and tolerates (in an immunological sense) a vast array of foreign antigens, that is, food and the commensal microorganisms residing in the gut. The feeding of a specific foreign protein can lead to a state of specific unresponsiveness to that protein known as oral tolerance, such that later injection of the protein, even in the presence of an adjuvant, yields no antibody response. This phenomenon may involve the spleen and lymph nodes as well as the mucosal immune system. See Gutgemann et al. (1998), Immunity 8: 667–73. However, enteric pathogens, such as, for example, *Salmonella, Yersinia*, or *Entamoeba histolytica*, can elicit a local, or even a systemic, immune response. The factors controlling whether the introduction of a foreign antigen into the gut elicits an immune response are incompletely understood. Janeway et al., supra at Part V, Ch. 14.

Many vaccines employ adjuvants to enhance the immune response to the antigen. An adjuvant strengthens or broadens the specificity of an immune response to an antigen. The immune response may include an increase in antibody titer or an increase in the number of antigen-reactive T cells. Methods for measuring such parameters exist in the art. See e.g. Zigterman et al. (1988), J. Immunol. Methods 106 (1): 101–07. The mechanism(s) by which adjuvants enhance an immune response are incompletely understood, but their use can be essential. Few existing vaccines can elicit a robust mucosal immune response to the selected antigen.

The invention encompasses a method for promoting a systemic or mucosal immune response against an antigen comprising administering a therapeutically effective amount of an antagonist of BTL-II and the antigen. The antagonists of BTL-II that can be used to practice the invention include, antagonistic antibodies or in vitro-selected binding proteins that bind specifically to the extracellular region of BTL-II, and small molecules that can inhibit the biological activity of BTL-II. Optionally, the antagonist of BTL-II protein and the antigen can be administered directly to a mucosal surface, such as orally, nasally, vaginally, gastrically, or rectally or by inhalation. For example, nasal administration has been reported to be more effective than vaginal administration in inducing a durable immune response in at least one case. Russell (2002), Am. J. Reprod. Immunol. 47 (5): 265–68. Alternatively, the BTL-II antagonist and/or the antigen can be injected, for example, subcutaneously, intravenously, intramuscularly, intraarterially, or intraperitoneally. In some embodiments, a BTL-II antagonist, such as an antibody, can be injected and an antigen can be administered directly to a mucosal surface.

Appropriate antigens for practicing the invention include all or part of any infectious agent or agent that is similar to an infectious agent. Infectious agents can include live or killed viruses, bacteria, and infectious eukaryotes such as amoeba, flagellates, or helminths. An agent that is similar to such an infectious agent may, for example, be a virus that is analogous to a virus that can infect the mammal being vaccinated, but cannot, itself, infect the mammal being vaccinated. An example of this is the vaccinia virus (which can produce disease in cows but not people) used by Jenner to produce a vaccine against smallpox, a similar virus that produces disease in humans. Janeway et al., supra, Part V, Ch. 14. Table 4 indicates specific examples of antigens that could be used to practice the invention.

TABLE 4

| Antigen Category | Some Specific Examples of Representative Antigens |
|---|---|
| Viruses | Rotavirus; foot and mouth disease; influenza, including influenza A and B; parainfluenza; Herpes species (Herpes simplex, Epstein-Barr virus, chicken pox, pseudorabies, cytomegalovirus); rabies; polio; hepatitis A; hepatitis B; hepatitis C; hepatitis E; measles; distemper; Venezuelan equine encephalomyelitis; feline leukemia virus; reovirus; respiratory syncytial virus; bovine respiratory syncytial virus; Lassa fever virus; polyoma tumor virus; parvovirus; canine parvovirus; papilloma virus; tick-borne encephalitis; rinderpest; human rhinovirus species; enterovirus species; Mengo virus; paramyxovirus; avian infectious bronchitis virus; HTLV 1; HIV-1; HIV-2; LCMV (lymphocytic choriomeningitis virus); adenovirus; togavirus (rubella, yellow fever, dengue fever); corona virus |
| Bacteria | *Bordetella pertussis*; *Brucella abortis*; *Escherichia coli*; Salmonella species including *Salmonella typhi*; streptococci; Vibrio species (*V. cholera*, *V. parahaemolyticus*); Shigella species; Pseudomonas species; Brucella species; Mycobacteria species (tuberculosis, avium, BCG, leprosy); pneumococci; staphlylococci; Enterobacter species; *Rochalimaia henselae*; Pasterurella species (*P. haemolytica*, *P. multocida*); Chlamydia species (*C. trachomatis*, *C. psittaci*, Lymphogranuloma venereum); Syphilis (Treponema pallidum); Haemophilus species; Mycoplasma species; Lyme disease (*Borrelia burgdorferi*); Legionnaires' disease; Botulism (*Colstridium botulinum*); *Corynebacterium diphtheriae*; *Yersinia entercolitica* |
| Ricketsial Infections | Rocky mountain spotted fever; thyphus; Ehrlichia species |
| Parasites and Protozoa | Malaria (*Plasmodium falciparum*, *P. vivax*, *P. malariae*); schistosomes; trypanosomes; Leishmania species; filarial nematodes; trichomoniasis; sarcosporidiasis; Taenia species (*T. saginata*, *T. solium*); Toxoplasma gondii; trichinelosis (Trichinella spiralis); coccidiosis (*Eimeria* species) ; helminths including Ascarus species |
| Fungi | *Cryptococcus neoformans*; *Candida albicans*; *Apergillus fumigatus*; coccidioidomycosis |
| Recombinant Proteins | Herpes simplex; Epstein-Barr virus; hepatitis B; pseudorabies; flavivirus (dengue, yellow fever); *Neisseria gonorrhoeae*; malaria: circumsporozoite protein, merozoite protein; trypanosome surface antigen protein; pertussis; alphaviruses; adenovirus |
| Proteins | Diphtheria toxoid; tetanus toxoid; meningococcal outer membrane protein (OMP); streptococcal M protein; hepatitis B; influenza hemagglutinin; cancer antigen; tumor antigens; toxins; exotoxins; neurotoxins; cytokines and cytokine receptors; monokines and monokine receptors |

TABLE 4-continued

| Antigen Category | Some Specific Examples of Representative Antigens |
|---|---|
| Synthetic Peptides | Malaria; influenza; foot and mouth disease virus; hepatitis B; hepatitis C |
| Polysaccharides | Pneumococcal polysaccharide; Haemophilis influenza polyribosyl-ribitolphosphate (PRP); *Neisseria meningitides*; *Pseudomonas aeruginosa*; *Klebsiella pneumoniae* |
| Oligosaccharide | Pneumococcal |

Alternatively, soluble BTL-II proteins can be used to promote tolerance to an antigen that is implicated in an autoimmune or inflammatory disease. For example, experimental autoimmune encephalomyelitis (EAE), a condition similar in many respects to multiple sclerosis, can be induced in rodents by injection of, for example, various epitopes of myelin basic protein or myelin oligodendrocyte glycoprotein (MOG). MOG-induced EAE can, in some cases, be ameliorated by prior feeding of small portions of MOG or butyrophilin. Stefferl et al. (2000), J. Immunol. 165: 2859–65. Soluble BTL-II proteins can be co-administered with an antigen known to be targeted in an autoimmune disease to promote tolerance to the antigen and thereby ameliorate the symptoms of the autoimmune disease. Optionally, the antigen can be administered directly to a mucosal surface, for example, nasally.

Inflammatory bowel diseases, including Crohn's disease and ulcerative colitis, include chronic inflammation of the gastrointestinal tract, possibly because of an abnormally enhanced immune response to antigens of normal gut flora. Both diseases likely have at least some genetic basis since occurrences tend to cluster in families and can be associated with some genetic markers. For example, mice that do not express the multiple drug resistance gene (mdr1a) spontaneously develop colitis. Panwala et al. (1998), J. Immunol. 161: 5733–44. The occurrence of both Crohn's disease and ulcerative colitis is likely also influenced by environmental factors because increased occurrence is observed among urbanized populations. Also, such diseases do not occur in the absence of normal gut flora.

Crohn's disease is involves an abnormal inflammation of any portion of the alimentary tract from the mouth to the anus, although in most patients abnormal inflammation is confined to the ileocolic, small-intestinal, and colonic-anorectal regions. Typically, the inflammation is discontinuous. Common symptoms include abdominal pain, anorexia, weight loss, fever, diarrhea, fullness and/or tenderness in the right lower quadrant of the abdomen, constipation, vomiting, and perianal discomfort and discharge. Other possible symptoms include peripheral arthritis, growth retardation, episcleritis, aphthous stomatitis, erythema nodosum, pyoderma gangrenosum, kidney stones, impaired urinary dilution and alkalinization, malabsorption, and gallstones, among others. See e.g. Strober et al., Medical Immunology, 10$^{th}$ Edition, Section III, Ch. 35 (2001); Merck Manual of Diagnosis and Therapy, 17$^{th}$ Edition, Section 3, Ch. 31 (1999). Macrophages isolated from patients with Crohn's disease produce increased amounts of IL-12, IFNγ, TNFα, and other inflammatory cytokines.

Ulcerative colitis, though it is sometimes hard to distinguish from Crohn's disease, is distinct from Crohn's disease in several respects. First, it is generally limited to the colon while Crohn's disease may occur throughout the alimentary tract. Second, ulcerative colitis mainly involves inflammation only of the superficial layers of the bowel, unlike Crohn's disease in which the inflammation can penetrate all way through the wall of the bowel or other location in the alimentary tract. Finally, ulcerative colitis typically involves a continuous area of inflammation, rather than the discontinuous sites of inflammation typical of Crohn's disease. Like Crohn's disease, ulcerative colitis is found primarily in urban areas. Also, genetic factors likely play a role in ulcerative colitis since there is a familial aggregation of cases. Autoantibodies are observed in ulcerative colitis patients more often than Crohn's disease patients. The autoantibodies are often directed to colonic epithelial cell components. Among the most common are antineutrophil cytoplasmic antibodies with specificities for catalase, α-enolase, and lactoferrin. In some cases such antibodies cross react with colonic microorganisms.

Symptoms of ulcerative colitis are variable. They may include diarrhea, tenesmus, abdominal cramps, blood and mucus in the stool, fever, and rectal bleeding. Toxic megacolon, a potentially life-threatening condition in which the colon is dilated beyond about 6 centimeters and may lose its muscular tone and/or perforate, may also occur. Other symptoms that may accompany ulcerative colitis include peripheral arthritis, ankylosing spondylitis, sacroiliitis, anterior uveitis, erythema nodosum, pyoderma gangrenosum, episcleritis, autoimmune hepatitis, primary sclerosing cholangitis, cirrhosis, and retarded growth and development in children.

Antibodies or in vitro-selected binding proteins that bind specifically to BTL-II proteins can be used to diagnose or predict the onset of inflammatory bowel disease. As illustrated in Example 4 below, BTL-II is overexpressed in the gut prior to the onset of symptoms and during the symptomatic phase in a mouse model of inflammatory bowel disease. Thus, overexpression of BTL-II can indicate the existence of inflammatory bowel disease and can predict the its onset. Anti-BTL-II antibodies can be used to detect overexpression of BTL-II by assaying a tissue sample from the bowel of a patient using an ELISA assay or other immune-based assays known in the art. See e.g. Reen (1994), Enzyme-Linked Immunosorbent Assay (ELISA), in *Basic Protein and Peptide Protocols*, Methods Mol. Biol. 32: 461–466. Overexpression can also be detected by nucleic acid-based methods for measuring BTL-II mRNA expression such as, for example, reverse transcription plus PCR (RT-PCR), among other mRNA expression assays known in the art. See e.g. Murphy et al. (1990), Biochemistry 29 (45): 10351–56.

In another embodiment, soluble BTL-II proteins of the invention can be used to treat an inflammatory bowel disease. A soluble BTL-II protein can bind to a specific receptor expressed on a B cell or a T cell, thereby enabling the downregulation of an immune response. Such a downregulation can, for example, prevent the activation of a macrophage or a B cell by a CD4$^+$ T cell or prevent activation of a T cell by an antigen. Alternatively, such a downregulation can cause a T cell to become anergic when it encounters an antigen to which its T cell receptor can specifically bind.

Antibodies or in vitro-selected binding proteins that bind specifically to BTL-II also find use as diagnostic reagents to identify patients with inflammatory bowel disease or at risk of developing inflammatory bowel disease. Since BTL-II is overexpressed prior to the onset of and during inflammatory bowel disease symptoms in a mouse model system (Example 4), an abnormally high level of BTL-II expression can indicate the presence of an inflammatory disease in the gut or a high risk of developing an inflammatory disease in the gut.

In addition, soluble BTL-II proteins can be useful in situations where down-modulation of an immune response is desired, such as transplantation (Manilay et al., 1998, *Curr. Opin. Immunol.* 10:532–538), graft versus host disease, graft rejection, autoimmune or inflammatory disease, gene therapy (Hackett et al., 2000, *Curr. Opin. Mol. Therap.* 2: 376–382), and the like. For example, a soluble BTL-II protein can be administered prior to, at approximately the same time (or either shortly before or shortly after), or concurrently with administration of a gene therapy vector to a mammal, transplantation, or as otherwise appropriate for the desired immuno-suppression. Also appropriate for such a treatment is an anti-idiotypic antibody that mimics the function of BTL-II.

An agonistic BTL-II antibody, a soluble BTL-II protein, or an anti-idiotypic antibody can be administered to a patient suffering from an autoimmune or inflammatory disease in order to decrease the number of detectable autoantibodies, to decrease the activation of immune effector cells, and/or to decrease or eliminate the symptoms of the disease. Autoimmune and inflammatory diseases include all conditions in which the patient's own tissues are subject to deleterious effects caused by the patient's immune system. Such effects can be mediated by autoantibodies and/or by the activation of immune effector cells, among other possibilities. Although the causes of autoimmune and inflammatory diseases are usually unclear, a correlation between the existence of various kinds of infections and various autoimmune diseases has been established in some cases and is a recurring subject of discussion in the scientific literature. See e.g. Corapcioglu et al. (2002), Thyroid 12: 613–17;Sewell et al. (2002), Immunol. Lett. 82: 101–10; Rose (1998), Semin. Immunol. 10 (1): 5–13; Matsiota-Bernard (1996), Clin. Exp. Immunol. 104: 228–35; and McMurray and Elbourne (1997), Semin. Arthritis Rheum. 26: 690–701.

One of skill in the art will appreciate that symptoms of autoimmune and inflammatory diseases are extremely diverse and can depend on what tissues are targeted by the patient's immune system. Autoimmune and inflammatory diseases can be organ-specific or systemic. Autoimmune and inflammatory diseases include, for example, arthritis, Addison's disease, insulin-dependent diabetes mellitus (type I diabetes mellitus), asthma, polyglandular endocrinopathy syndromes, systemic lupus erythematosus, chronic active hepatitis, various forms of thyroiditis (including Hashimoto's thyroiditis, transient thyroiditis syndromes, and Grave's disease), lymphocytic adenohypophysitis, premature ovarian failure, idiopathic phyoparathyroidism, pernicious anemia, glomerulonephritis, autoimmune neutropenia, Goodpasture's syndrome, multiple sclerosis, vitiligo, myasthenia gravis, rheumatoid arthritis, scleroderma, primary Sjogren's syndrome, polymyositis, autoimmune hemolytic anemia, inflammatory bowel disease (including Crohn's disease and ulcerative colitis), psoriasis, psoriatic arthritis, dermatitis, autoimmune thrombocytopenic purpura, pemphigus vulgaris, acute rheumatic fever, mixed essential cryoglobulinemia, and warm autoimmune hemolytic anemia, among many others.

Vectors and Host Cells

The present invention also provides vectors containing the nucliec acids of the invention, as well as host cells transformed with such vectors. Any of the nucleic acids of the invention may be contained in a vector, which generally includes a selectable marker and an origin of replication, for propagation in a host. The vectors further include suitable transcriptional or translational regulatory sequences, such as those derived from a mammalian, microbial, viral, or insect genes, operably linked to the BTL-II nucleic acid. Examples of such regulatory sequences include transcriptional promoters, operators, or enhancers, mRNA ribosomal binding sites, and appropriate sequences that control transcription and translation. Nucleotide sequences are operably linked when the regulatory sequence functionally relates to the DNA encoding the target protein. Thus, a promoter nucleotide sequence is operably linked to a BTL-II nucleic sequence if the promoter nucleotide sequence directs the transcription of the BTL-II sequence.

Selection of suitable vectors for the cloning of BTL-II nucleic acids encoding the target BTL-II proteins of this invention will depend upon the host cell in which the vector will be transformed, and, where applicable, the host cell from which the target polypeptide is to be expressed. Suitable host cells for expression of BTL-II proteins include prokaryotes, yeast, insect, and higher eukaryotic cells, each of which is discussed below.

The BTL-II proteins to be expressed in such host cells may also be fusion proteins that include regions from heterologous proteins. As discussed above, such regions may be included to allow, for example, secretion, improved stability, facilitated purification, targeting, or oligomerization of the BTL-II protein. For example, a nucleic acid sequence encoding an appropriate signal sequence can be incorporated into an expression vector. A nucleic acid sequence encoding a signal sequence (secretory leader) may be fused in-frame to a BTL-II sequence so that BTL-II is translated as a fusion protein comprising the signal peptide. A signal peptide can be functional in the intended host cell can promote extracellular secretion of the BTL-II protein. A heterologous signal peptide can replace the native signal sequence. Examples of signal peptides that are functional in mammalian host cells include the signal sequence for interleukin-7 (IL-7) described in U.S. Pat. No. 4,965,195, the signal sequence for interleukin-2 receptor described in Cosman et al. ((1984), *Nature* 312: 768); the interleukin-4 receptor signal peptide described in EP Patent No. 0 367 566; the type I interleukin-1 receptor signal peptide described in U.S. Pat. No. 4,968,607; the type II interleukin-1 receptor signal peptide described in EP Patent No. 0 460 846; the signal sequence of human IgK (which is METDTLLLWVLLLWVPGSTG); SEQ ID NO:29); and the signal sequence of human growth hormone (which is MATGSRTSLLLAFGLLCLPWLQEGSA); SEQ ID NO:30). Preferably, the signal sequence will be cleaved from the BTL-II protein upon secretion of the BTL-II protein from the cell. Other signal sequences that can be used in practicing the invention include the yeast α-factor and the honeybee melatin leader in Sf9 insect cells. Brake (1989), Biotechnology 13: 269–280; Homa et al. (1995), Protein Exp. Purif. 6141–148; Reavy et zal. (2000), Protein Exp. Purif. 6: 221–228.

Suitable host cells for expression of the proteins of the invention include prokaryotes, yeast, and higher eukaryotic cells. Suitable prokaryotic hosts to be used for the expression of these polypeptides include bacteria of the genera *Escherichia, Bacillus*, and *Salmonella*, as well as members of the genera *Pseudomonas, Streptomyces*, and *Staphylococcus*. For expression in prokaryotic cells, for example, in *E. coli*, the polynucleotide molecule encoding BTL-II protein preferably includes an N-terminal methionine residue to facilitate expression of the recombinant polypeptide. The N-terminal Met may optionally be cleaved from the expressed polypeptide.

Expression vectors for use in cellular hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pGEM vectors (Promega), pSPORT vectors, and pPROEX vectors (InVitrogen, Life Technologies, Carlsbad, Calif.), Bluescript vectors (Stratagene), and pQE vectors (Qiagen).

BTL-II can also be expressed in yeast host cells from genera including *Saccharomyces, Pichia*, and *Kluveromyces*. Preferred yeast hosts are *S. cerevisiae* and *P. pastoris*. Yeast vectors will often contain an origin of replication sequence from a 2μ yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of the target polypeptides expressed in yeast hosts may be accomplished by the inclusion of nucleotide sequence encoding the yeast α-factor leader sequence at the 5' end of the BTL-II-encoding nucleotide sequence. Brake (1989), Biotechnology 13: 269–280.

Insect host cell culture systems can also be used for the expression of BTL-II proteins. The proteins of the invention are preferably expressed using a baculovirus expression system, as described, for example, in the review by Luckow and Summers ((1988), BioTechnology 6: 47).

BTL-II proteins of the invention can be expressed in mammalian host cells. Non-limiting examples of suitable mammalian host cell lines include the COS-7 line of monkey kidney cells (Gluzman et al. (1981), Cell 23: 175–182), Chinese hamster ovary (CHO) cells (Puck et al. (1958), PNAS USA 60: 1275–1281), CV-1 (Fischer et al. (1970), Int. J. Cancer 5: 21–27) and human cervical carcinoma cells (HELA) (ATCC CCL 2).

The choice of a suitable expression vector for expression of BTL-II proteins of the invention will depend upon the specific mammalian host cell to be used. Examples of suitable expression vectors include pcDNA3.1/Hygro$^+$ (Invitrogen), pDC409 (McMahan et al. (1991), EMBO J. 10: 2821–2832), and pSVL (Pharmacia Biotech). Expression vectors for use in mammalian host cells can include transcriptional and translational control sequences derived from viral genomes. Commonly used promoter sequences and enhancer sequences that can be used to express BTL-II include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg ((1982) *Mol. Cell. Biol.* 2:161–170), Cosman et al. ((1986) Mol. Immunol. 23:935–941), Cosman et al. ((1984) Nature 312: 768–771), EP-A-0367566, and WO 91/18982.

Modification of a BTL-II nucleic acid molecule to facilitate insertion into a particular vector (for example, by modifiying restriction sites), ease of use in a particular expression system or host (for example, using preferred host codons), and the like, are known and are contemplated for use in the invention. Genetic engineering methods for the production of BTL-II proteins include the expression of the polynucleotide molecules in cell free expression systems, in cellular hosts, in tissues, and in animal models, according to known methods.

Therapeutic Methods

"Treatment" of any disease mentioned herein encompasses an alleviation of at least one symptom of the disease, a reduction in the severity of the disease, or the delay or prevention of disease progression to more serious symptoms that may, in some cases, accompany the disease or to at least one other disease. Treatment need not mean that the disease is totally cured. A useful therapeutic agent needs only to reduce the severity of a disease, reduce the severity of symptom(s) associated with the disease or its treatment, or delay the onset of more serious symptoms or a more serious disease that can occur with some frequency following the treated condition. For example, if the disease is an inflammatory bowel disease, a therapeutic agent may reduce the number of distinct sites of inflammation in the gut, the total extent of the gut affected, reduce pain and/or swelling, reduce symptoms such as diarrhea, constipation, or vomiting, and/or prevent perforation of the gut. A patient's condition can be assessed by standard techniques such as an x-ray performed following a barium enema or enteroclysis, endoscopy, colonoscopy, and/or a biopsy. Suitable procedures vary according to the patient's condition and symptoms.

The invention encompasses a method of treating inflammatory diseases, including autoimmune diseases, graft versus host disease, and inflammatory bowel diseases, using an amount of a BTL-II protein or antibody for a time sufficient to induce a sustained improvement over baseline of an indicator that reflects the severity of a particular disorder or the severity of symptoms caused by the disorder or to delay or prevent the onset of a more serious disease that follows the treated condition in some or all cases. The treatments of the invention may be used before, after, or during other treatments for the disorder in question that are commonly used, or they may be used without other treatments. For example, Crohn's disease and ulcerative colitis are commonly treated with sulfasalazine, 5-aminosalicylic acid, or cortico-steroids. These treatments may be used before, during, or after the treatments of the invention.

Any of the above-described therapeutic agents can be administered in the form of a composition, that is, with one or more additional components such as a physiologically acceptable carrier, excipient, or diluent. For example, a composition may comprise a soluble BTL-II protein as described herein plus a buffer, an antioxidant such as ascorbic acid, a low molecular weight polypeptide (such as those having less than 10 amino acids), a protein, amino acids, carbohydrates such as glucose, sucrose, or dextrins, chelating agent such as EDTA, glutathione, and/or other stabilizers, excipients, and/or preservatives. The composition may be formulated as a liquid or a lyophilizate. Further examples of components that may be employed in pharmaceutical formulations are presented in Remington's Pharmaceutical Sciences, 16$^{th}$ Ed., Mack Publishing Company, Easton, Pa., (1980).

Compositions comprising therapeutic molecules described above can be administered by any appropriate means including, but not limited to, parenteral, topical, oral, nasal, vaginal, rectal, or pulmonary (by inhalation) administration. If injected, the composition(s) can be administered intra-articularly, intravenously, intraarterially, intramuscularly, intraperitoneally, or subcutaneously by bolus injection or continuous infusion. Localized administration, that is, at the site of disease, is contemplated, as are transdermal delivery and sustained release from implants, skin patches, or suppositories. Delivery by inhalation includes, for example, nasal or oral inhalation, use of a nebulizer, inhalation in aerosol form, and the like. Administration via a suppository inserted into a body cavity can be accomplished, for example, by inserting a solid form of the composition in a chosen body cavity and allowing it to dissolve. In the case of soluble BTL-II proteins or agonists to treat an inflammatory bowel disease, administration via a rectal suppository may be particularly appropriate since it localizes the therapeutic appropriately. Other alternatives include eyedrops, oral preparations such as pills, lozenges, syrups, and chewing gum, and topical preparations such as lotions, gels, sprays, and ointments. In most cases, therapeutic molecules that are polypeptides can be administered topically or by injection or inhalation.

The therapeutic molecules described above can be administered at any dosage, frequency, and duration that can be effective to treat the condition being treated. The dosage depends on the molecular nature of the therapeutic molecule and the nature of the disorder being treated. Treatment may be continued as long as necessary to achieve the desired results. Therapeutic molecules of the invention can be administered as a single dosage or as a series of dosages given periodically, including multiple times per day, daily, every other day, twice a week, three times per week, weekly, every other week, and monthly dosages, among other possible dosage regimens. The periodicity of treatment may or may not be constant throughout the duration of the treatment. For example, treatment may initially occur at weekly intervals and later occur every other week. Treatments having durations of days, weeks, months, or years are encompassed by the invention. Treatment may be discontinued and then restarted. Maintenance doses may be administered after an initial treatment.

Dosage may be measured as milligrams per kilogram of body weight (mg/kg) or as milligrams per square meter of skin surface (mg/m$^2$) or as a fixed dose, irrespective of height or weight. All of these are standard dosage units in the art. A person's skin surface area is calculated from her height and weight using a standard formula.

The invention has been described with reference to specific examples. These examples are not meant to limit the invention in any way. It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

This specification contains numerous citations to patents, patent applications, and publications. Each is hereby incorporated by reference for all purposes.

EXAMPLE 1

Isolation of Human BTL-II cDNAs

RNA was isolated from several sources, human colon tissue samples from patients with Crohn's disease or ulcerative colitis, the human colon cancer cell line Caco-2 (American Type Culture Collection (ATCC) No. HTB-37), and a colon epithelial cell line called T84 (ATCC No. CCL-248). The RNA was reverse transcribed and amplified by PCR using primers that were designed on the basis of the nucleic acid sequence disclosed in NCBI accession no. NM_019602. This yielded an upstream portion of the sequences of full length BTL-II (SEQ ID NO:3) and the splice variant sequences disclosed in SEQ ID NO:7, SEQ ID NO:9, SEQ ID NO:11, SEQ ID NO:13, and SEQ ID NO:15. Isolation of a cDNA containing the 3' end of the BTL-II mRNA was accomplished using 3' RACE (Rapid Amplification of cDNA Ends), i.e., essentially the protocols of Frohman et al. ((1988), Proc. Natl. Acad. Sci. USA 85 (23): 8998–9002). From the analysis of many variants of the BTL-II cDNA by 3' RACE revealed no variants that encoded soluble proteins lacking a transmembrane domain. As shown in FIGS. 5a, 6a, and 7a, many of the variants contained sequence polymorphisms (or allelic variations) at a number of sites in the BTL-II sequence.

EXAMPLE 2

Isolation of Murine BTL-II cDNAs

Figure 8:
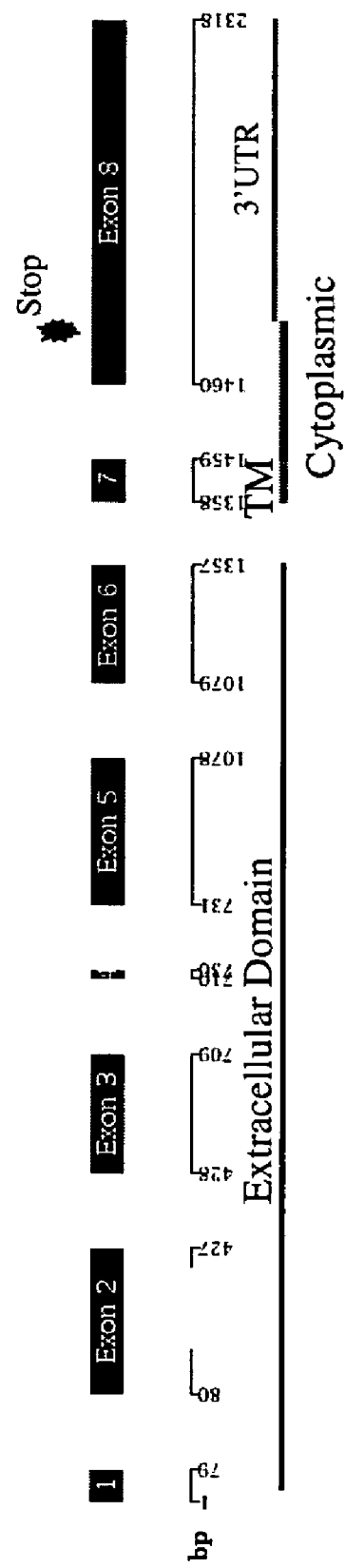
FIG. 8 is a diagram of the structure of the murine BTL-II gene and MRNA. Symbols are as in FIG. 5 except that the number refer to positions in SEQ ID NO:5.

Murine BTL-II cDNAs were isolated as follows. RNA was isolated from murine colon and small intestine using a kit the isolation and purification of RNA (the RNEASY® kit; Qiagen) and treated with DNAse I (Ambion), according to recommendations of the manufacturer, to eliminate residual chromosomal DNA. Purified RNA was transcribed into cDNA, using a reaction mixture containing isolated RNA in 10 mM Tris-HCl, pH 8.3, 50 mM KCL, 5 mM MgCl$_2$, 1 mM of each dNTP, 2.5 µM random hexamer primers, 1 U/µl RNAse inhibitor, and 2.5 U/☐1 MuLV Reverse Transcriptase (PE Biosystems). The reaction mixture was incubated for 10 minutes at 25° C., followed by 30 minutes at 48° C., followed by 5 minutes at 95° C. PCR amplification reactions for the BTL-II gene were performed in a final volume of 100 µl containing 10 mM Tris-HCl, pH 8.3, 50 mM KCl, 1.5 mM MgCl$_2$, 200 µM of each dNTP, and 2.5U ampliTaq DNA polymerase (Perkin Elmer) and 25 pmol of both the upstream (5'-TTACTGAGAGAGG-GAAACGGGCTGTTTTCTCC; SEQ ID NO:31) and downstream (5'-GGACTTCATTGGTGACTGATGCCATC-CAC; SEQ ID NO:32) primers. The amplification reactions were carried out for 35 cycles of 40 seconds at 94° C., 40 seconds at 55° C., and 40 seconds at 72° C. The amplification products were analyzed on a 2% agarose gel, visualized by ethidium bromide, and sequenced. By visual estimation, splice variants lacking exon 3 (FIG. 9a) were more abundant than variants containing exons 1 to 8 (FIG. 8).

EXAMPLE 3

Expression of BTL-II in Cells and Tissues from Various Sources

Expression of BTL-II MRNA was measured using real time PCR essentially according to the protocols of Heid et al. ((1996), Genome Res. 6 (10): 986–94) and using standard reverse transcription followed by PCR (RT-PCR; see e.g. Fuqua et al. (1990), Biotechniques 9 (2): 206–11). All cells types tested were of human origin except the CD11c⁺ CD8⁺ B220⁺ (or plasmacytoid) dendritic cells from Peyer's patches which were from mouse. Cells in which BTL-II expression was detected were the following: human B cells, unstimulated or stimulated with killed *Staphylococcus aureus*, CD40 ligand, and interleukin 4; normal human bronchial epithelial cells (NHBE cells; see Lechner et al. (1983), Cancer Res. 43 (12 pt. 1): 5915–21) stimulated with interferon γ; Calu-3 cells, a lung epithelial cell line (ATCC No. HTB-55), unstimulated; T84 cells, a human colon epithelial cell line, unstimulated or stimulated with interferon γ; Caco-2 cells, a human colon cancer cell line, unstimulated; CD11c⁺ (low expressing) CD8⁺ B220⁺ cells from murine Peyer's patches, which are predominantly dendritic cells; and murine peripheral blood leukocytes. Expression, on an absolute scale, was low in most cells tested. Expression of BTL-II mRNA was not detected in dendritic cells resulting from in vitro treatment of human peripheral blood monocytes to induce differentiation into a dendritic cell type. However, BTL-II expression was detected in CD123⁺ plasmacytoid dendritic cells purified from human blood purified from human peripheral blood. BTL-II MRNA was highly enriched in the CD11c⁺ (low expressing) CD8⁺ B220⁺ subset of murine dendritic cells from Peyer's patches. Expression of BTL-II mRNA was detected in a number of murine tissue types by similar methods including spleen, lymph node, stomach, mesenteric lymph nodes, bone marrow, small intestine, cecum, lung, large intestine, Peyer's patch, and thymus. The highest levels of expression were detected in small intestine, Peyer's patch, and cecum tissue.

EXAMPLE 4

Expression of BTL-II in a Murine Model for Inflammatory Bowel Disease

Mdr1a –/– mice can be a model system for the study of chronic inflammatory bowel disease. Panwala et al. (1998), J. Immunol. 161: 5733–44. The murine multiple drug resistance gene, mdr1a, encodes a 170 kDa transmembrane protein that is expressed in many tissues including intestinal epithelial cells and lymphoid cells. Mice deficient in mdr1a are susceptible to developing severe spontaneous intestinal inflammation characterized by dysregulated epithelial cell growth and massive leukocyte infiltration into the lamina propria of the large intestine. Treating mdr1a –/– mice with oral antibiotics prevents both the development of disease and resolves active inflammation. Lymphoid cells isolated from mice with active colitis demonstrate enhanced reactivity to intestinal bacterial antigens. Although mdr1a is expressed by both epithelial cells and leukocytes, the development of colitis correlates with lack of mdr1a expression on epithelial cells.

The mdr1a –/– mice used were in an FVB genetic background. Typically, approximately 20% of a group of mdr1a –/– mice spontaneously develop colitis at 18 to 20 weeks of age, while the remaining mice in the mdr1a –/– colony remain healthy and do not develop colitis. The percentage of animals that develop disease is dependent on the cleanliness of the animal facility.

Figure 10:
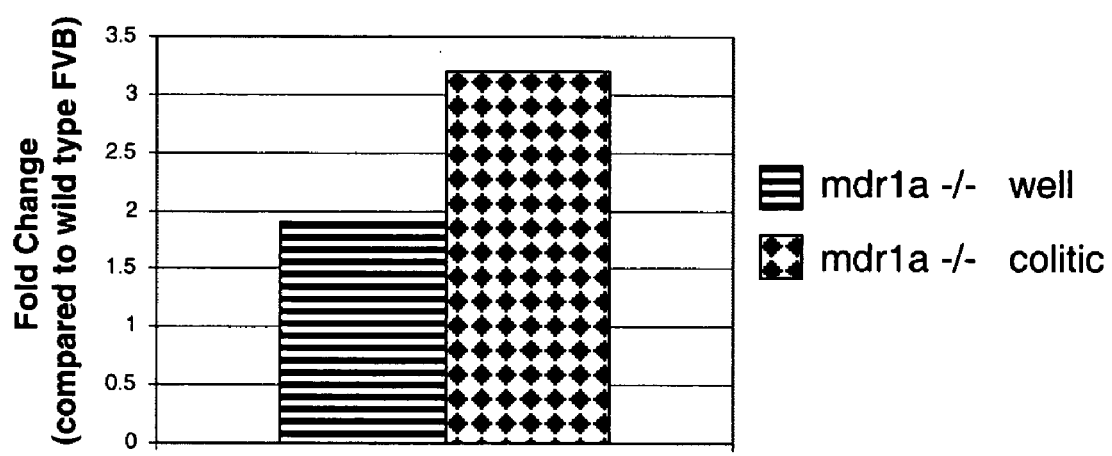
FIG. 10 represents expression of BTL-II MRNA in colonic tissue of mdr1a −/− mice (which carry the mdr1a null mutation in an FVB background) when exhibiting no symptoms of inflammatory bowel disease (horizontal stripes) or when exhibiting symptoms of inflammatory bowel disease (checkerboard pattern) relative to expression of BTL-II MRNA in colonic tissue of non-symptomatic, wild type FVB mice. Measurements were done by hybridizing fluorescently-labeled cDNA to an Affymetrix chip containing an oligonucleotide complementary to BTL-II MRNA.

Initially, RNA was prepared from gut tissue and, after reverse transcription incorporating a fluorescent label into the resulting cDNA, used to hybridize to an array of probes on a custom-prepared Affymetrix chip containing an oligonucleotide designed to detect BTL-II mRNA based on the sequence published by Stammers et al. ((2000), Immunogenetics 51: 373–82). Overexpression of BTL-II mRNA was detected in mdr1a –/– mice (relative to wild type individuals of the FVB strain) both before the onset of inflammatory bowel disease symptoms and during the symptoms. A sample of such data is shown in FIG. 10. These data show that BTL-II MRNA is expressed to a greater extent in mdr1a –/– mice than in wild type FVB mice. Moreover, even higher expression of BTL-II MRNA accompanies the onset of symptoms of inflammatory bowel disease.

Figure 11:
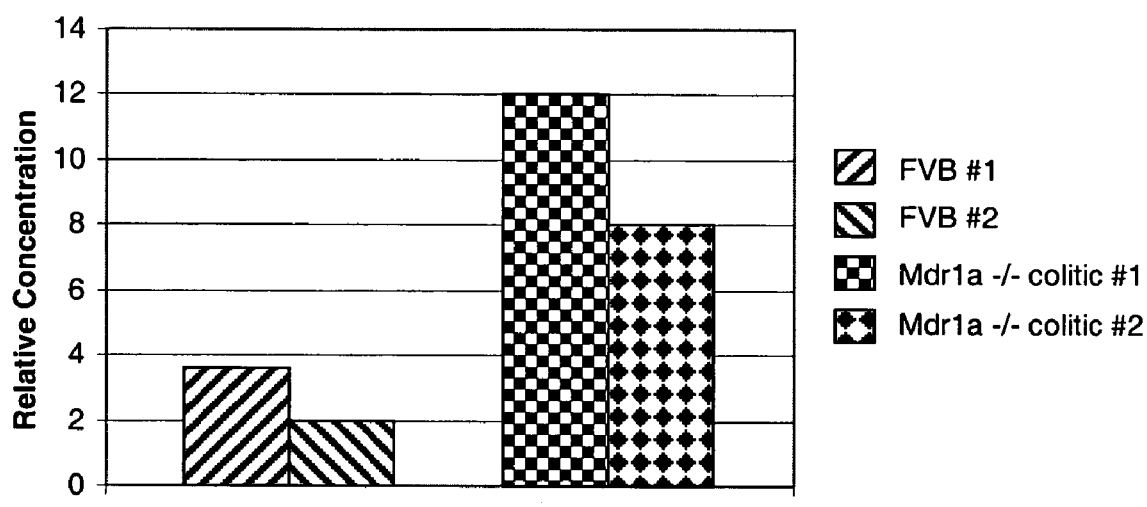
FIG. 11 is a graph showing the relative concentrations of BTL-II mRNA detected by a real time PCR assay of colon tissue from two different wild type mice of the FVB strain (FVB #1 and #2; diagonal lines) and from two mdr1a −/− mice showing symptoms of inflammatory bowel disease (Mdr1a −/− #1 and #2; checkerboard patterns).

These results were confirmed by analysis of the same RNA using a real time PCR technique (Heid et al. (1996), Genome Res. 6 (10): 986–94). This analysis showed overexpression of BTL-II MRNA by two symptomatic mdr1a –/– mice relative to two healthy wild type FVB mice. This data is diagrammed in FIG. 11. The two parental mice are represented by the two bars marked with diagonal stripes towards the left of FIG. 11, and the two symptomatic mdr1a –/– are represented by the two bars marked with checkered patterns towards the right of FIG. 11. These data indicate that there is approximately a 2 to 5 fold difference in expression between the wild type mice and the symptomatic mdr1a –/– mice. Thus, higher levels of BTL-II mRNA are expressed in mice with symptoms of inflammatory bowel disease than in wild type mice with no symptoms.

EXAMPLE 5

Construction of a BTL-II:Fc Fusion Protein

A soluble BTL-II protein consisting of the extracellular region of murine BTL-II fused to a human Fc region (BTL-II:Fc) was produced in the following way. A fusion cDNA construct encoding BTL-II:Fc was prepared by fusing nucleic acids encoding the extracellular region of murine BTL-II to nucleic acids encoding a human IgG1 (in-frame). To produce the BTL-II:Fc protein, mammalian cells were transfected with the fusion cDNA construct using the LIPOFECTAMINE™ 2000 transfection method (Invitrogen, Carlsbad, Calif., USA). BTL-II:Fc protein-containing supernatants were harvested 6–7 days post transfection, and the BTL-II:Fc protein was purified by Protein A column chromatography. The nucleic acid sequence encoding the BTL-II:Fc protein and the BTL-II:Fc amino acid sequence are found in SEQ ID NO:19 and SEQ ID NO:20, respectively.

EXAMPLE 6

Suppression of Human T Cell Proliferation by BTL-II:Fc

The following experiment tests whether a soluble form of BTL-II can suppress T cell proliferation in vitro in response to a monoclonal anti-CD3ε antibody with or without other costimulatory molecules.

Figure 12A:
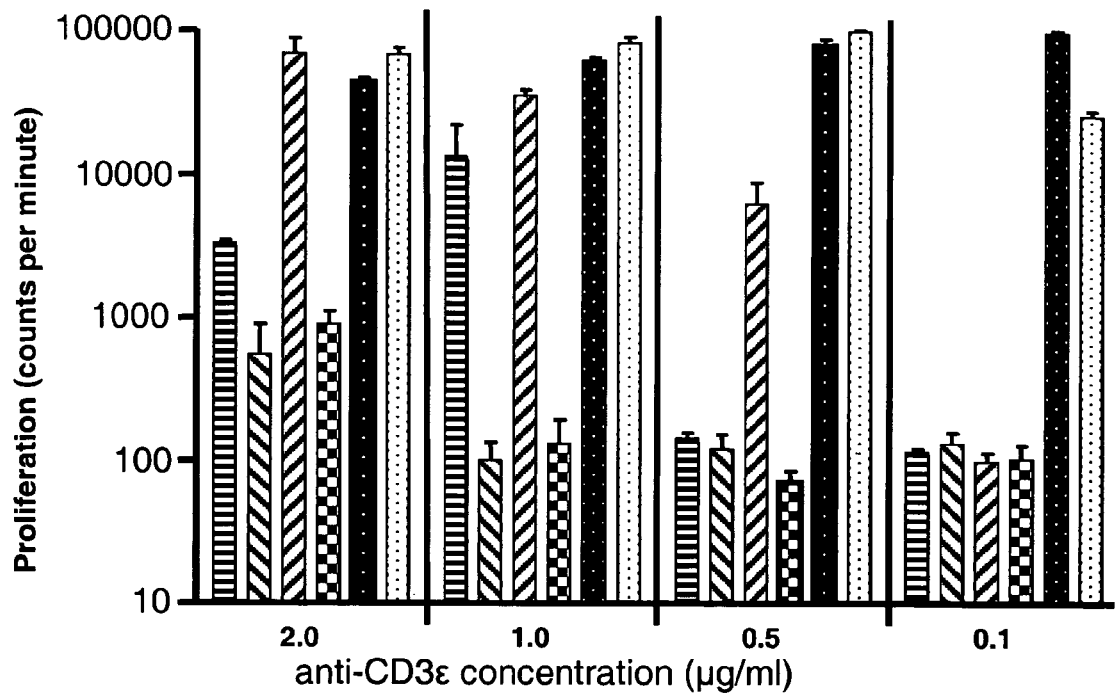
FIG. 12a is a bar graph showing proliferation (as evidenced by uptake of $^3$H-thymidine) of purified human T cells cultured with the following proteins: anti-CD3ε antibody alone, ▬; anti-CD3ε antibody and BTL-II:Fc, ▧; anti-CD3ε antibody and B7RP-1:Fc, ▨; anti-CD3ε antibody, B7RP-1:Fc, and BTL-II:Fc, ▦; anti-CD3ε antibody and B7-2:Fc, ▪; and anti-CD3ε antibody, B7-2:Fc, and BTL-II:Fc, ▦.
Figure 12B:
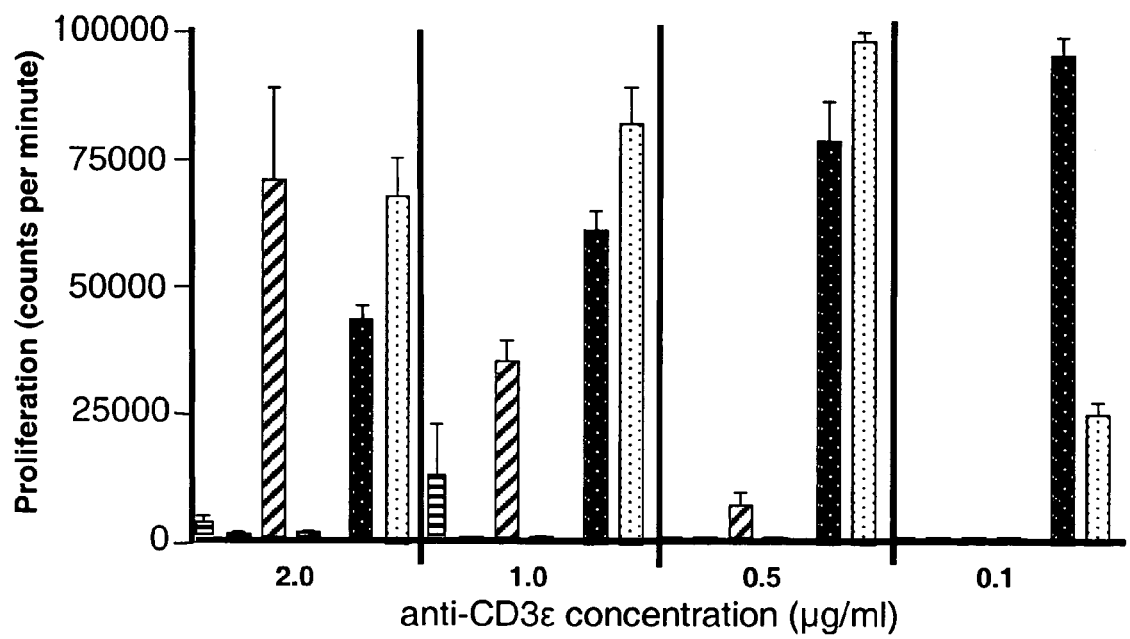
FIG. 12b is identical to FIG. 12a, except that a linear, rather than a logarithmic scale is used.

BTL-II:Fc was made as described in Example 5. A 96 well, U bottom microtiter plate was coated with varying concentrations of anti-CD3ε antibody with or without one or more other proteins. FIG. 12 indicates what proteins were used in each sample as follows: anti-CD3ε antibody alone, ▤; anti-CD3ε antibody and BTL-II:Fc, ▨; anti-CD3ε antibody and B7RP-1:Fc, ▨; anti-CD3ε antibody, B7RP-1:Fc, and BTL-II:Fc, ▨; anti-CD3ε antibody and B7-2:Fc, ▨; anti-CD3ε antibody, B7-2:Fc, and BTL-II:Fc, ▨. B7RP-1:Fc consists of the extracellular region of B7RP-1 (also known as B7h) fused to an Fc region of an antibody, and B7-2:Fc consists of the extracellular region of B7-2 fused to an Fc region of an antibody. Both of these proteins are members of the B7 family of proteins known to modulate T cell response to antigens. These fusion proteins can be purchased from commercial vendors such as, for example, R & D Systems (Minneapolis, Minn., USA), or can be isolated as described in Example 5 for the essentially as described in Example 5, although it also is available from R & D Systems under the name B7-H2/Fc. The microtiter plate wells were coated by adding 100 μl of phosphate buffered saline (PBS)

containing the concentration of anti-CD3ε antibody indicated in FIG. 12 with or without one or more other proteins, that is BTL-II:Fc (10 µg/ml), B7RP1 :Fc (10 µg/ml), and/or B7-2:Fc (2 µg/ml). Plates were incubated at 4° C. overnight and then washed twice with PBS. Human T cells were purified from human peripheral blood mononuclear cells using a CD4+ T cell isolation kit from Miltenyi Biotec (Bergisch Gladbach, Germany), which functions by magnetically labeling and depleting peripheral blood cells other than CD4+ T cells, resulting in relatively pure population of untouched CD4+ T cells. About $1\times10^5$ purified T cells were added to each well in a volume of 200 µl of culture medium (RPMI with 10% fetal bovine serum). The cells were incubated for a total of 72 hours. At 64 hours, 1 µCi of $^3$H-thymidine was added to each well. At the end of the 72 hours, unincorporated thymidine was removed by using an automatic cell harvester (obtained from Tomtec, Hamden, Conn., USA), which deposits the cells onto a filter and washes away the culture medium. The filters with the cells on them were then counted in a scintillation counter to determine how much radioactivity the cells had incorporated. The results are shown in FIGS. 12a and 12b, which differ only in that FIG. 12a has a logarithmic scale and FIG. 12b has a linear scale.

Figure 13:
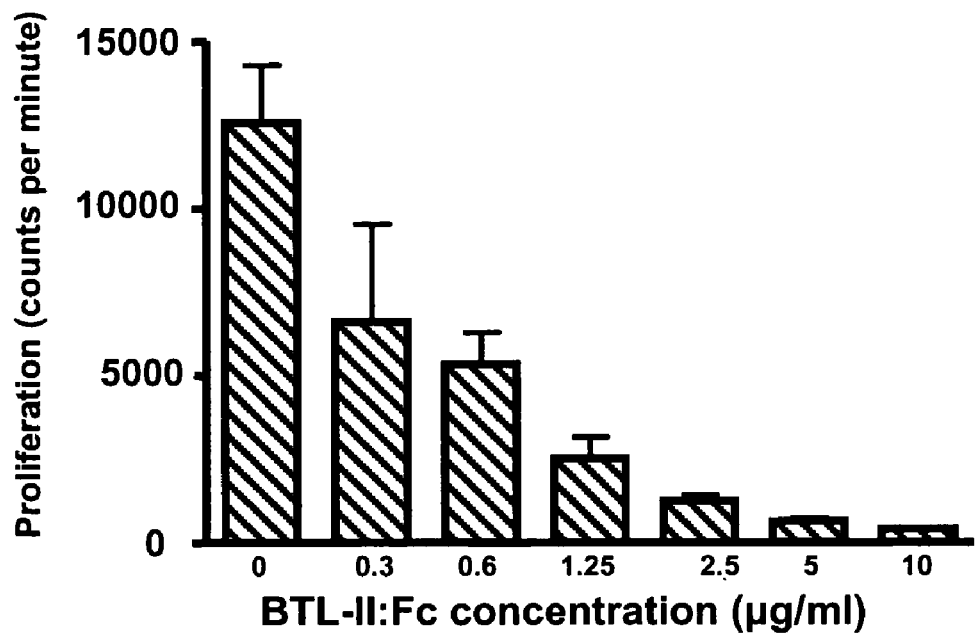
FIG. 13 is a bar graph showing proliferation of purified human T cells in response to a constant amount of anti-CD3ε antibody and a varying amount of BTL-II:Fc, as indicated.

The results indicate that BTL-II:Fc can suppress the T cell proliferation induced by anti-CD3ε antibody. FIG. 12a and 12b. In FIG. 12a, samples containing BTL-II plus anti-CD3ε antibody (▨) proliferate less than samples containing only anti-CD3ε antibody (▬) at the higher antibody concentrations tested. Moreover, it is clear that both B7-2 (▦) and B7RP-1 (▨) stimulate anti-CD3ε antibody-induced T cell proliferation. The concentration of anti-CD3ε antibody required to see an effect on T cell proliferation by adding B7-2:Fc is lower than that required to see a similar effect by adding B7RP-1:Fc. Further, BTL-II can also suppress this increased T cell proliferation in response to the addition of B7-2:Fc (▦) and B7RP-1 :Fc (▨). The effect of BTL-II:Fc on proliferation induced by B7-2:Fc plus anti-CD3ε antibody is evident only at the lowest concentration of anti-CD3ε antibody tested, whereas the effects of BTL-II:Fc on proliferation induced by B7RP-1 :Fc are more apparent at the three higher concentrations of anti-CD3ε antibody tested. Thus, the observed effects depend on the concentration of anti-CD3ε antibody FIG. 13 shows that the suppression of human T cell proliferation by BTL-II:Fc is also dependent on BTL-II:Fc concentration. The experiment was performed as described above except that the anti-CD3ε antibody concentration remained constant at 0.5 µg/ml. The BTL-II:Fc concentration varied from 0 to 10 µg/ml, as indicated in FIG. 13. The results shown in FIG. 13 indicate that suppression of anti-CD3ε-induced T cell proliferation is dependent on the concentration of BTL-II:Fc.

EXAMPLE 7

BTL-II:Fc Suppresses Murine T Cell Proliferation

Figure 14:
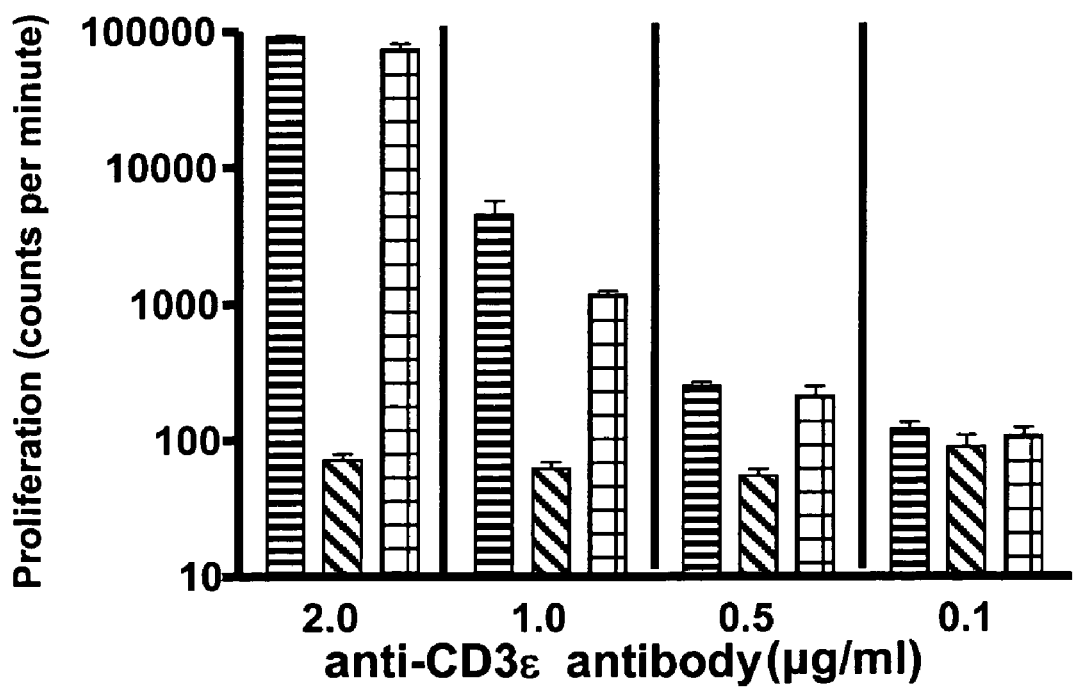
FIG. 14 is a bar graph showing proliferation of murine T cells in response to ariti-CD3ε antibody alone, ▬, anti-CD3ε antibody plus BTL-II:Fc, ▧, or anti-CD3ε antibody plus a control protein consisting of a human Fc region, ▭.

This experiment was done to determine whether BTL-II:Fc can suppress the proliferation of murine, as well as human, T cells. A T cell proliferation assay was performed as essentially described in Example 6 except that murine T cells purified using magnetic microbeads purchased from Miltneyi Biotec GmbH (Bergisch Gladbach, Germany) were used instead of human T cells. A protein consisting of a human Fc region, which was made in transfected CHO cells, served as a control. The wells were coated with either anti-CD3ε antibody alone (▬) at the concentration indicated in FIG. 14 or with anti-CD3ε antibody plus either BTL-II:Fc (▨) at 10 µg/ml or the protein consisting of a human Fc region (▨) at 10 µg/ml. The results indicate that BTL-II:Fc, but not a protein consisting of a human Fc region alone, can suppress murine T cell proliferation in response to anti-CD3ε antibody. FIG. 14.

EXAMPLE 8

BTL-II:Fc Does Not Supress Murine B Cell Proliferation

Figure 15:
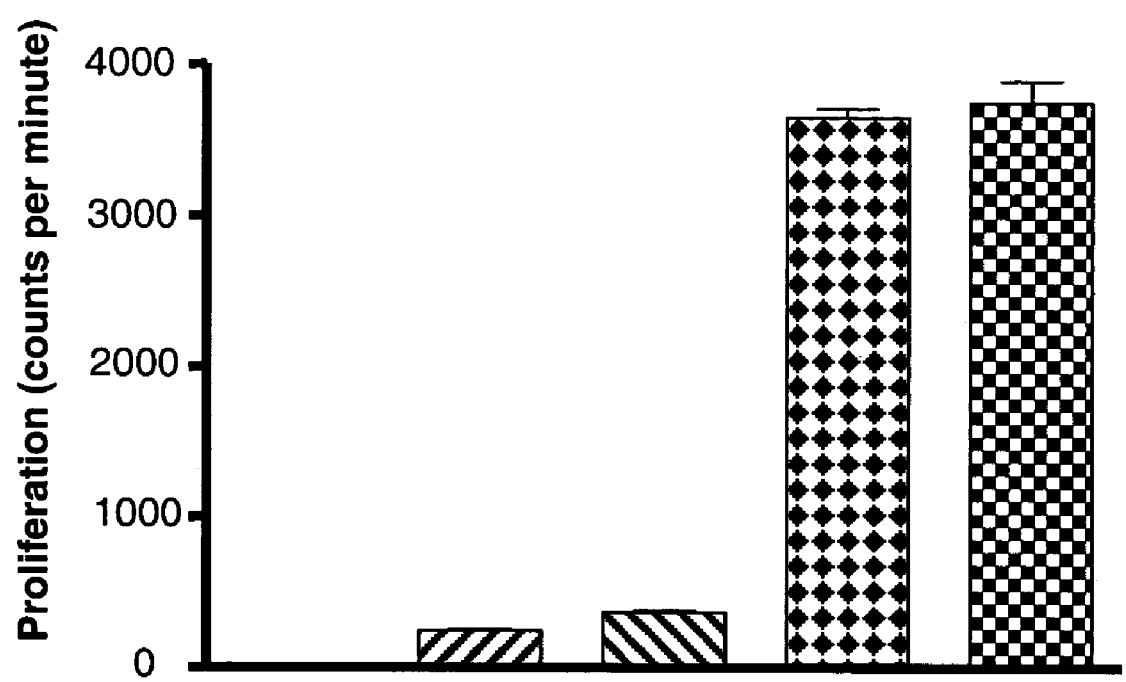
FIG. 15i is a bar graph showing proliferation of murine B cells in response to no added protein, ▭, TALL-1 protein alone, ▨, an anti-IgM antibody alone, ▧, TALL-1 plus and anti-IgM antibody, ▦, and TALL-1, anti-IgM antibody, and BTL-II:Fc, ▦.

The following experiment was designed to determine whether human BTL-II:Fc can inhibit proliferation of murine B cells induced by TALL-1 and an IgM antibody. The experiment was performed essentially as described by Khare et al. ((2000), Proc. Natl. Acad. Sci. 97 (7): 3370–75). Briefly, murine B cells were purified from spleens by first purifying lymphocytes by density gradient centrifugation and then passing the lymphocytes over a B cell column, which removes monocytes/macrophages and CD4+ and CD8+ cells (Cedarlane, Westbury, N.Y.). About $1\times10^5$ purified B cells in MEM plus 10% heat inactivated fetal calf serum were incubated for 4 days at 37° C. in a 96 well microtiter plate with or without goat F(ab')$_2$ anti-mouse IgM (2 µg/ml), human TALL-1 (10 µg/ml), and/or BTL-II:Fc (10 µg/ml). $^3$H-thymidine (1 µCi) was added during the last 8 hours of incubation. Cells were harvested as described in Example 6 at the end of 4 days and counted in a scintillation counter. The markings in FIG. 15 indicate the following combinations of cells and proteins: B cells alone, ☐ (This is the leftmost bar on the graph shown in FIG. 15, but there is no detectable signal); B cells plus TALL-1, ▨; B cells plus anti-IgM antibody, ▨; B cells plus TALL-1 and anti-IgM antibody, ▦; and B cells plus TALL-1, anti-IgM antibody, and BTL-II: Fc, ▦. The results indicate that BTL-II:Fc has no effect on the proliferation of B cells induced by TALL-I and anti-IgM antibody. FIG. 15. Therefore, BTL-II appears to inhibit proliferation of T cells, but not of B cells.

EXAMPLE 9

Effects of BTL-II:Fc on Cytokine Production by T Cells

The following experiment was aimed at determining whether BTL-II:Fc has effects on cytokine production by T cells. T cells were purified and microtiter plate wells were coated with proteins as described in Example 6. About $1\times10^5$ cells were added to each well in a volume of 200 µl of medium (RPMI with 10% fetal bovine serum). Cells were incubated for 64 hours at 37° C. Then 150 µl was removed to determine cytokine concentration, and 1 µi of $^3$H-thymidine was added to the remaining 50 µl in each well. The microtiter plate was then allowed to incubate for an additional 8 hours at 37° C. and then washed and counted as described in Example 6 to ascertain differences in proliferation (shown in FIG. 16a). Markings to indicate what proteins were used to coat the well are as in FIGS. 12a and 12b (explained in Example 6). Concentrations of interferon gamma (IFNγ), interleukin 2 (IL2), and interleukin 5 (IL5) were determined using an electrochemical-based immunoassay system for simultaneous detection of multiple cytokines sold by Meso Scale Discovery (MSD, Gaithersburg, Md., USA, which affiliated with IGEN International, Inc.). The principles and operation of this kind of cytokine detection system are explained, in e.g., Sennikov et al. (2003), J. Immunol. Methods 275: 81–88. The units for the amounts of cytokines are taken from the readings generated by the MSD machine. The actual concentrations of cytokines in the medium cannot be determined from this data without comparison to a standard curve generated with a protein of known concentration, which did not accompany this particular experiment. However, comparisons between readings within a single experiment can provide relative amounts of cytokines present in control versus experimental samples.

Figure 16A:
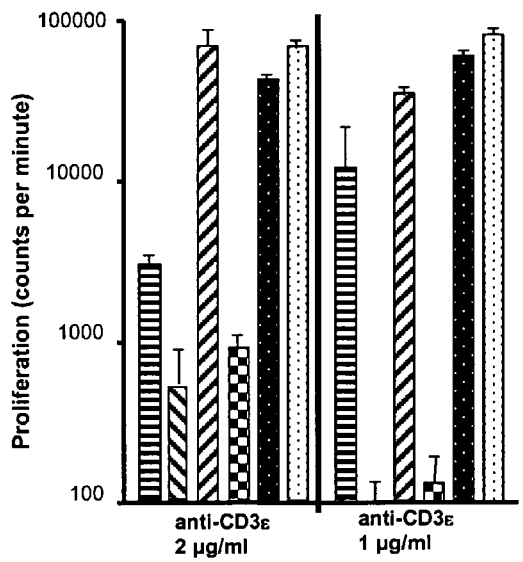
Figure 16B:
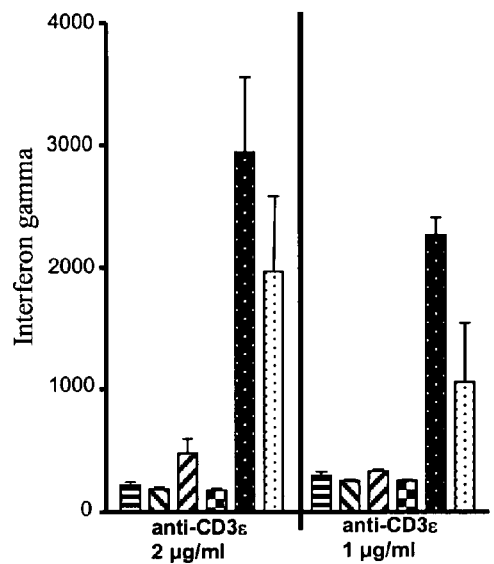
Figure 16C:
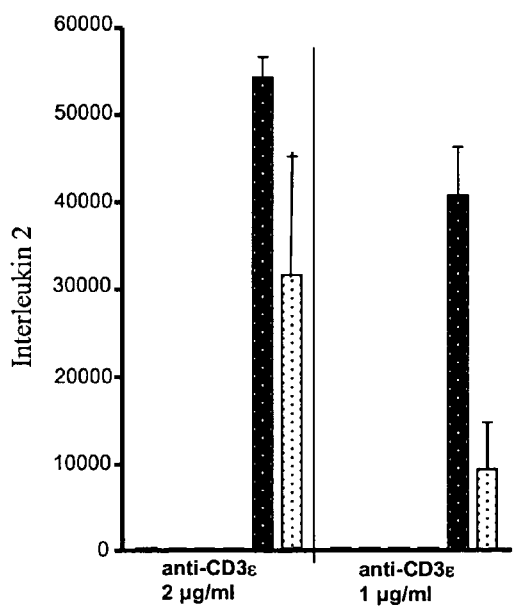
Figure 16D:
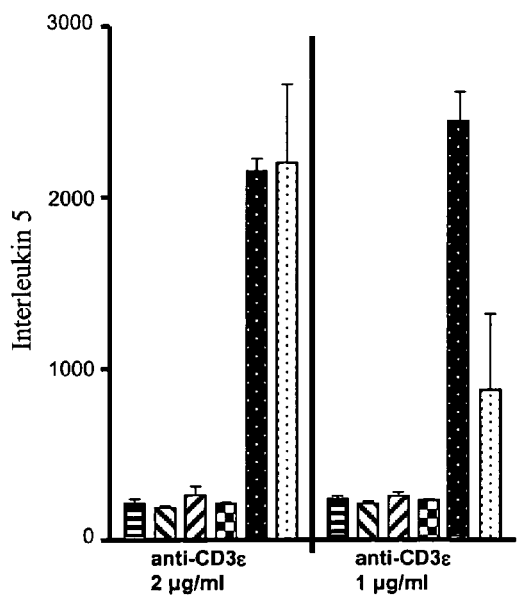

The results are shown in FIGS. 16a–16d. FIG. 16a indicates that BTL-II:Fc inhibited proliferation in response to anti-CD3ε antibody or anti-CD3ε antibody plus B7RP-1:Fc, but not in response to anti-CD3ε antibody plus B7-2:Fc at the concentrations of anti-CD3ε antibody used. However, as noted in Example 6 (FIGS. 12a and 12b), at lower anti-CD3ε antibody concentrations, i.e., 0.1 μg/ml, cell proliferation in response to anti-CD3ε antibody plus B7-2:Fc is inhibited by BTL-II:Fc. Production of IFNγ, IL2, and IL5 was low in wells coated with anti-CD3ε antibody alone, and addition of BTL-II:Fc did not decrease it significantly further. FIGS. 16b–16d. Increased IFNγ production in response to the addition of either B7RP-1:Fc or B7-2:Fc to anti-CD3ε antibody was inhibited by BTL-II:Fc. FIG. 16b. In addition, increased IL2 and IL5 production in response to the addition of B7-2:Fc to anti-CD3ε antibody was inhibited by BTL-II:Fc. FIGS. 16c and 16d. At the concentrations tested, the addition of B7RP-1:Fc to anti-CD3ε antibody did not appreciably increase IL2 or IL5 production. FIGS. 16c and 16d. These results indicate that BTL-II:Fc can inhibit production of at least some cytokines in response to a combination of anti-CD3ε antibody plus either B7-2:Fc or B7RP-1:Fc.

EXAMPLE 10

Treatment of T Cells With BTL-II:Fc Does Not Result in Massive Cell Death

Figure 17:
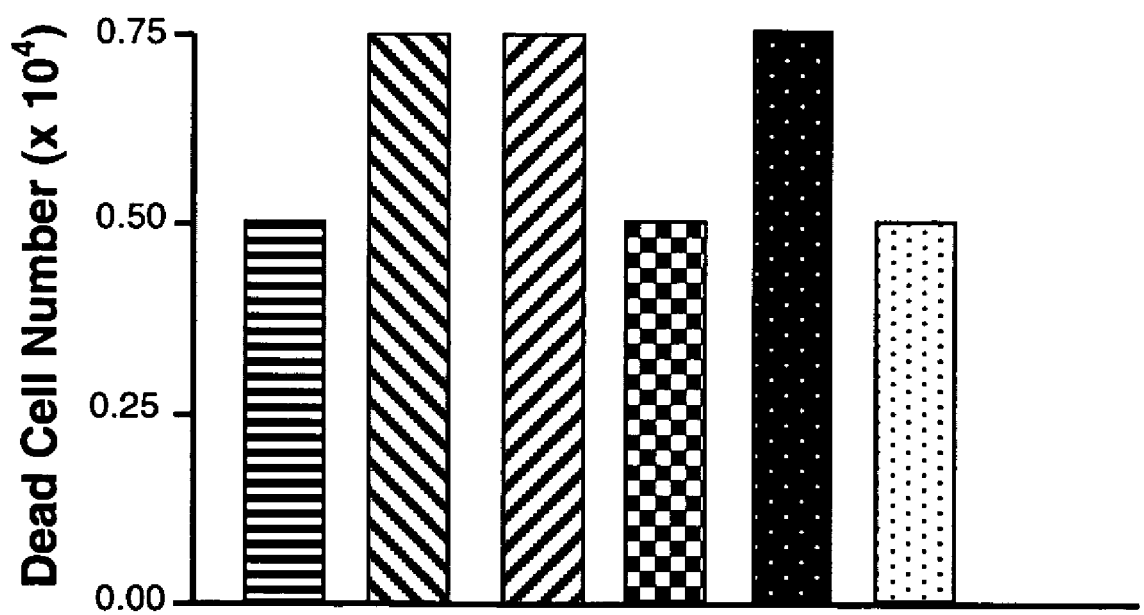

The following experiment was done to determine whether inhibition of T cell proliferation by BTL-II:Fc involved massive cell death. A T cell proliferation assay was performed essentially as described in Example 6, except that the cells were not labeled with $^3$H-thymidine. Cells were counted in a hemocytometer after 72 hours of culture, and cell viability was determined by trypan blue staining. Proteins used to coat the microtiter plate wells are indicated in FIG. 17 as explained in Example 6 and shown in FIGS. 12a and 12b. The anti-CD3ε antibody was used at a concentration of 2 μg/ml. The results indicate that the number of dead cells in each well falls within a range between about $0.5 \times 10^4$ and $0.75 \times 10^4$ cells, regardless of the proteins used to coat the wells. FIG. 17. Therefore, the differences in cell proliferation observed in the presence of BTL-II:Fc do not reflect a substantial toxic effect of BTL-II:Fc.

EXAMPLE 11

Murine BTL-II Does Not Bind to Murine CTLA4, CD28, ICOS, or PD-1

The following set of experiments addresses the question of whether BTL-II binds to one of several known binding partners of other B7 proteins. For example, B7RP-1 is known to bind to ICOS (Yoshinaga et al. (1999), Nature 402: 827–32), CD80 (also called B7-1) is known to bind to CTLA4 and CD28, as does CD86 (also called B7-2; see e.g. Sharpe and Freeman (2002), Nature Reviews Immunology 2: 116–26), and PD-L1 and PD-L2 are known to bind to PD-1 (Latchman et al. (2001), Nature Immunology 2 (3): 261–68).

The experiment was done as follows. First, fusion proteins comprising the extracellular region of a protein known to bind a B7 protein plus the Fc region of a human IgG antibody were obtained or isolated. Fusion proteins comprising an Fc region of a human antibody plus the extracellular region of either murine CD28 (mCD28-huFC) or murine PD-1 (PD1-huFC) were purchased from R & D Systems (Minneapolis, Minn., USA). The other two B7 binding proteins (CTLA4-huFC and ICOS-huFC) are also available from R & D Systems, but were made as follows. A cDNA encoding the extracellular region of murine CTLA4 and another encoding the extracellular region of murine ICOS were each fused to cDNA encoding the Fc region of a human IgG antibody in a vector appropriate for expression in mammalian cells. Each of these constructs was used to transfect cells, and the fusion proteins were purified from the culture medium of the transfected cells by Protein A chromatography.

Figure 18:
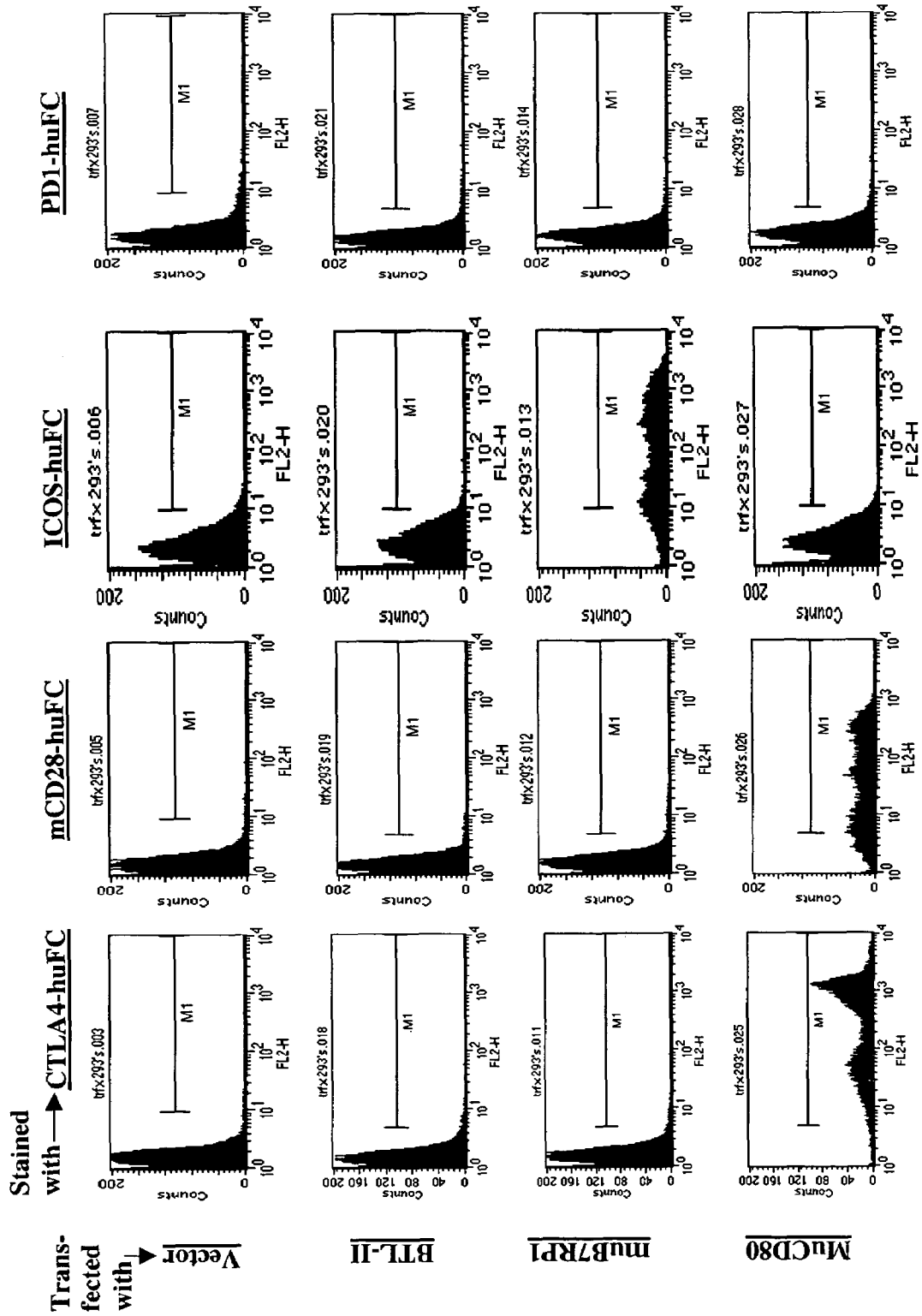
FIG. 18 shows FACS scans of cells transfected with either an empty vector (top line), or a vector containing cDNA encoding murine BTL-II (second line), murine B7RP-1 (third line), or murine CD80 (bottom line). The cells were stained with the following proteins: (1) the extracellular region of murine CTLA4 fused to a human Fc region of an IgG1 antibody (first column); (2) the extracellular region of murine CD28 fused to a human Fc region from an IgG1 antibody (second column); (3) the extracellular region of murine ICOS fused to a human Fc region from an IgG1 antibody (third column); and (4) the extracellular region of PD1 fused to a human Fc region of an IgG1 antibody (fourth column). The vertical axis of each scan (labeled "counts") represents cell number and the horizontal axis (labeled "FL2-H") represents fluorescence. The horizontal line labeled "M1" shows where the "gate" was set on the FACS machine. Cells encompassed in this gate are considered positive; all others are considered negative. The small lettering above each FACS scan indicates an individual sample number.

Full length versions of each of three murine cDNAs (encoding BTL-II, B7RP-1, CD80) were inserted into a vector appropriate for expression. About 10 μg of each of these constructs, along with an empty vector, were used separately to transfect 293 cells. Two days post transfection, about one million cells from each of the four transfections were stained with each of the fusion proteins described above. Bound protein was detected using a fluorescently labeled antibody against the human IgG Fc region. The stained cells were analyzed by FACS. The results are shown in FIG. 18.

As expected, cells transfected with the empty vector (top line of FIG. 18) did not stain with any of the four fusion proteins. Cells transfected with murine BTL-II (second line of FIG. 18) behaved similarly, indicating that none of the fusion proteins bind to BTL-II. As expected, cells transfected with murine B7RP-1 stained with ICOS-huFC, but not with any of the other fusion proteins. Also as expected, cells transfected with murine CD80 stained with CTLA4-huFC or mCD28-huFC, but not with ICOS-huFC or PD1-huFC. These results indicate that BTL-II fails to bind to four proteins, CTLA-4, PD-1, ICOS, and CD28, each of which is known to bind to at least one protein in the B7 family.

What is claimed is:

1. An isolated BTL-II protein comprising an amino acid sequence consisting of amino acids 29 to 457 of SEQ ID NO:4.

2. The protein of claim 1 comprising amino acids 29 to 482 of SEQ ID NO:4.

3. An isolated protein comprising a polypeptide consisting of an amino acid sequence at least 85% identical to amino acids 30 to 358 of SEQ ID NO:10, wherein the identity region of the amino acid sequence aligned with amino acids 30 to 358 of SEQ ID NO:10, is at least 150 amino acids,
   wherein the amino acid sequence is at least 85% identical to amino acids 127 to 157 of SEQ ID NO:10, wherein the identity region of the amino acid sequence aligned with amino acids 127 to 157 of SEQ ID NO:10, is at least 20 amino acids long, and
   wherein the protein can inhibit the proliferation of T cells induced by an anti-CD3 antibody.

4. The protein of claim 3, wherein the amino acid sequence is at least 90% identical to amino acids 30 to 358 of SEQ ID NO:10.

5. The protein of claim 3, wherein the amino acid sequence is at least 90% identical to amino acids 127 to 157 of SEQ ID NO:10.

6. An isolated protein comprising a polypeptide consisting of an amino acid sequence at least 85% identical to amino acids 32 to 358 of SEQ ID NO:10,
   wherein the identity region of the amino acid sequence aligned with amino acids 32 to 358 of SEQ ID NO:10 is at least 275 amino acids, and wherein the protein can inhibit the proliferation of T cells induced by an anti-CD3 antibody.

7. The protein of claim 6, wherein the amino acid sequence is at least 90% identical to amino acids 32 to 358 of SEQ ID NO:10.

8. An isolated protein comprising a first polypeptide consisting of a first amino acid sequence at least 85% identical to amino acids 32 to 358 of SEQ ID NO:10, wherein the identity region of the first amino acid sequence aligned to SEQ ID NO:10 is at least about 175 amino acids long,
  wherein the first amino acid sequence is not more than 390 amino acids in length,
  wherein the protein can inhibit the proliferation of T cells induced by an anti-CD3 antibody,
  wherein the first amino acid sequence is not at least 85% identical to amino acids 148 to 232 of SEQ ID NO:4 with an identity region of the first amino acid sequence aligned to amino acids 148 to 232 of SEQ ID NO:4 of at least about 40 amino acids, and
  wherein the protein does not comprise a second amino acid sequence that is at least 85% identical to amino acids 148 to 232 of SEQ ID NO:4 with an identity region of the second amino acid sequence aligned to amino acids 148 to 232 of SEQ ID NO:4 of at least about 40 amino acids.

9. The protein of claim 8, wherein the first amino acid sequence is not more than about 270 amino acids in length.

10. The protein of claim 8, wherein the first amino acid sequence is at least 90% identical to SEQ ID NO:10.

11. The protein of claim 1 further comprising another polypeptide.

12. The protein of claim 11, wherein the other polypeptide is an Fc region of an antibody.

13. The protein of claim 3 further comprising another polypeptide.

14. The protein of claim 13, wherein the other polypeptide is an Fc region of an antibody.

15. The protein of claim 8 further comprising another polypeptide.

16. The protein of claim 15, wherein the other polypeptide is an Fc region of an antibody.

17. An immunogenic fragment of SEQ ID NO:10,
  wherein the immunogenic fragment is capable of eliciting antibodies that bind specifically to a protein consisting of amino acids 30–358 of SEQ ID NO:10,
  wherein the immunogenic fragment is at least 10 amino acids long, and
  wherein the immunogenic fragment spans a portion of SEQ ID NO:10 encode by the splice junction between nucleotides 427 and 428 of SEQ ID NO:9.

18. An immunogenic fragment of SEQ ID NO:10, wherein the immunogenic fragment spans positions 141 to 143 of SEQ ID NO:10,
  wherein the immunogenic fragment is capable of eliciting antibodies that bind specifically to a protein consisting of amino acids 30 to 358 of SEQ ID NO:10, and
  wherein the immunogenic fragment is at least 10 amino acids long.

19. An isolated protein comprising an amino acid sequence identical to amino acids 32 to 358 of SEQ ID NO:10.

20. The protein of claim 19 comprising amino acids 30 to 358 of SEQ ID NO:10.

21. The protein of claim 4, wherein the amino acid sequence is at least 94% identical to amino acids 30 to 358 of SEQ ID N:10.

22. The protein of claim 5, wherein the amino acid sequence is at least 94% identical to amino acids 127 to 157 of SEQ ID NO:10.

23. The protein of claim 7, wherein the amino acid sequence is at least about 96% identical to amino acids 32–358 of SEQ ID NO:10.

24. The protein of claim 10, wherein the first amino acid sequence is at least 94% identical to SEQ ID NO:10.

25. The protein of claim 6 further comprising another polypeptide.

26. The protein of claim 25, wherein the other polypeptide is an Fc region of an antibody.

* * * * *